(12) United States Patent
Shiraiwa et al.

(10) Patent No.: US 9,556,264 B2
(45) Date of Patent: Jan. 31, 2017

(54) HUMANIZED ANTI-EPIREGULIN ANTIBODY, AND CANCER THERAPEUTIC AGENT COMPRISING SAID ANTIBODY AS ACTIVE INGREDIENT

(71) Applicant: Chugai Seiyaku Kabushiki Kaisha, Tokyo (JP)

(72) Inventors: Hirotake Shiraiwa, Shizuoka (JP); Keiko Esaki, Shizuoka (JP); Tomoyuki Igawa, Shizuoka (JP); Taichi Kuramochi, Shizuoka (JP); Atsuhiko Maeda, Shizuoka (JP); Shigero Tamba, Shizuoka (JP); Hiroyuki Tsunoda, Shizuoka (JP); Tatsuhiko Tachibana, Shizuoka (JP); Yasuko Kinoshita, Kanagawa (JP); Masami Suzuki, Shizuoka (JP); Atsuhiko Kato, Shizuoka (JP); Etsuko Takeiri, Shizuoka (JP); Eri Hashimoto, Kanagawa (JP); Yoshinori Watanabe, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/369,539

(22) PCT Filed: Dec. 28, 2012

(86) PCT No.: PCT/JP2012/084042
§ 371 (c)(1),
(2) Date: Jun. 27, 2014

(87) PCT Pub. No.: WO2013/100120
PCT Pub. Date: Jul. 4, 2013

(65) Prior Publication Data
US 2015/0110793 A1  Apr. 23, 2015

(30) Foreign Application Priority Data

Dec. 28, 2011 (JP) .................................. 2011-287654
Jun. 13, 2012 (JP) .................................. 2012-133394

(51) Int. Cl.
*C07K 16/22* (2006.01)
*A61K 39/00* (2006.01)

(52) U.S. Cl.
CPC ......... *C07K 16/22* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/77* (2013.01); *C07K 2317/92* (2013.01); *C07K 2317/94* (2013.01)

(58) Field of Classification Search
CPC ............ C07K 2317/24; C07K 2317/56; C07K 2317/734; C07K 2317/732; C07K 2317/565
USPC ............................................ 424/133.1, 178.1
See application file for complete search history.

(56) References Cited

U.S. PATENT DOCUMENTS

| 5,190,858 | A | 3/1993 | Sorvillo et al. |
|---|---|---|---|
| 5,783,417 | A | 7/1998 | Komurasaki et al. |
| 5,994,511 | A | 11/1999 | Lowman et al. |
| 6,172,213 | B1 | 1/2001 | Lowman et al. |
| 6,949,245 | B1 | 9/2005 | Sliwkowski |
| 7,435,590 | B2 | 10/2008 | Komurasaki |
| 8,084,584 | B2 | 12/2011 | Sugo et al. |
| 2002/0160014 | A1 | 10/2002 | Rodriguez et al. |
| 2004/0044187 | A1 | 3/2004 | Sato et al. |
| 2004/0236078 | A1 | 11/2004 | Carter et al. |
| 2005/0171339 | A1 | 8/2005 | Sugo et al. |
| 2006/0154333 | A1 | 7/2006 | Pienkos et al. |
| 2006/0188497 | A1 | 8/2006 | Rodriguez et al. |
| 2008/0166756 | A1 | 7/2008 | Tsuchiya et al. |
| 2009/0061485 | A1 | 3/2009 | Tsuchiya et al. |
| 2009/0324491 | A1 | 12/2009 | Aburatani et al. |
| 2010/0092490 | A1 | 4/2010 | Uenaka et al. |
| 2010/0310463 | A1 | 12/2010 | Cicortas Gunnarsson et al. |
| 2010/0310464 | A1 | 12/2010 | Cicortas Gunnarsson et al. |

(Continued)

FOREIGN PATENT DOCUMENTS

| CA | 2 665 528 A1 | 4/2008 |
|---|---|---|
| CN | 1761682 A | 4/2006 |

(Continued)

OTHER PUBLICATIONS

Asano, R., et al., "The advance on the antibody therapy—the expectation to the clinical application," *Igaku no Ayumi* 211:723-727, Maruzen Co Ltd., Tokyo, Japan (2004).

(Continued)

*Primary Examiner* — Lynn Bristol
(74) *Attorney, Agent, or Firm* — Sterne, Kessler, Goldstein & Fox P.L.L.C.

(57) ABSTRACT

The inventors successfully produced anti-Epiregulin antibodies showing cross-species reactivity between cynomolgus monkey (non-human animals) and human, anti-Epiregulin antibodies with suppressed chemical degradation, anti-Epiregulin antibodies with lowered isoelectric point, anti-Epiregulin antibodies with increased thermal denaturation midpoint temperature, and anti-Epiregulin antibodies with reduced amount of aggregate by performing appropriate amino acid residue substitutions in the variable-region sequences of the humanized EP27 antibody which inhibits growth of cancer cells by exhibiting cytotoxic activity and neutralizing activity against human Epiregulin-expressing cancer cells.

25 Claims, 21 Drawing Sheets

(56) References Cited

U.S. PATENT DOCUMENTS

| | | | |
|---|---|---|---|
| 2012/0141501 | A1 | 6/2012 | Yoshida et al. |
| 2014/0073005 | A1 | 3/2014 | Umaña et al. |

FOREIGN PATENT DOCUMENTS

| | | | |
|---|---|---|---|
| EP | 1 069 185 A1 | 1/2001 | |
| EP | 1 331 266 A1 | 7/2003 | |
| EP | 1 350 521 A1 | 10/2003 | |
| EP | 1 607 404 A1 | 12/2005 | |
| EP | 1 829 962 A1 | 9/2007 | |
| EP | 2 070 548 A1 | 6/2009 | |
| EP | 2 436 397 A1 | 4/2012 | |
| EP | 2 728 002 A1 | 5/2014 | |
| JP | 2003-503366 | 1/2003 | |
| JP | 2005-519023 A | 6/2005 | |
| JP | 2006-516893 A | 7/2006 | |
| JP | 2008-527978 A | 7/2008 | |
| KR | 10-2005-0108389 A | 11/2005 | |
| RU | 2270029 C2 | 9/2003 | |
| WO | WO 94/29340 A1 | 12/1994 | |
| WO | WO 99/51743 | 10/1999 | |
| WO | WO 01/00245 A2 | 1/2001 | |
| WO | WO 02/31140 A1 | 4/2002 | |
| WO | WO 02/45747 A1 | 6/2002 | |
| WO | WO 03/057881 A1 | 7/2003 | |
| WO | WO 2004/003019 A2 | 1/2004 | |
| WO | WO 2004/065540 A2 | 8/2004 | |
| WO | WO 2004/081047 A1 | 9/2004 | |
| WO | WO 2005/068503 A2 | 7/2005 | |
| WO | WO 2005/076979 A2 | 8/2005 | |
| WO | WO 2006/029497 A1 | 3/2006 | |
| WO | WO 2006/067913 A1 | 6/2006 | |
| WO | WO 2007/015578 A1 | 2/2007 | |
| WO | WO 2007/092932 A2 | 8/2007 | |
| WO | WO 2008/047723 A1 | 4/2008 | |
| WO | WO 2010/137654 | 12/2010 | |
| WO | WO 2010/142952 A2 | 12/2010 | |
| WO | WO 2010/142990 A1 | 12/2010 | |
| WO | WO 2013/100120 A1 | 7/2013 | |
| WO | WO 2014/208482 A1 | 12/2014 | |

OTHER PUBLICATIONS

Baba, I., et al., "Involvement of Deregulated Epiregulin Expression in Tumorigenesis in Vivo through Activated Ki-Ras Signaling Pathway in Human Colon Cancer Cells," *Cancer Res.* 60:6886-6889, American Association for Cancer Research, Philadelphia, PA (2000).

Hanai, Nobuo, "Antibody Modification and Transgenic Mice," *Biotherapy* 17:415-421, Kluwer Academic Publishers, Dordrecht, Netherlands (2003).

Minn, A.J., et al., "Genes that mediate breast cancer metastasis to lung," *Nature* 436:518-524, Nature Publishing Group, London, England (Jul. 2005).

R&D Systems, Inc., "Monoclonal Anti-human Epiregulin Antibody," *R&D Systems Catalog*, Catalog No. MAB1425, 1 page, Minneapolis, MN (2003).

R&D Systems, Inc., "Anti-human Epiregulin Antibody," *R&D Systems Catalog*, Catalog No. AF1195, 2 pages, Minneapolis, MN (2003).

Shirakata, Y., et al., "Epiregulin, a Novel Member of the Epidermal Growth Factor Family, Is an Autocrine Growth Factor in Normal Human Keratinocytes," *J. Biol. Chem.* 275:5748-5753, American Society for Biochemistry and Molecular Biology, Bethesda, MD (2000).

Shirasawa, S., et al., "Dermatitis due to epiregulin deficiency and a critical role of epiregulin in immune-related responses of keratinocyte and macrophage," *Proc. Natl. Acad. Sci. U.S.A.* 101:13921-13926, National Academy of Sciences, Washington, DC (2004).

Sunanaga, N., et al., "Haigan ni okeru Epiregulin Idenshi no Hatsugen ni tsuite no Kento," *The Journal of the Japanese Respiratory Society* 45:167, The Japanese Respiratory Society (2007).

Takahashi, M., et al., "Epiregulin as a Major Autocrine/Paracrine Factor Released From ERK- and p38MAPK-Activated Vascular Smooth Muscle Cells," *Circulation* 108:2524-2529, American Heart Association, Inc. (2003).

Toyoda, H., et al., "Distribution of mRNA for human epiregulin, a differentially expressed member of the epidermal growth factor family," *Biochem. J.* 326:69-75, Portland Press, London, England (1997).

Toyoda, H., et al., "Epiregulin. A Novel Epidermal Growth Factor With Mitogenic Activity for Rat Primary Hepatocytes," *J. Biol. Chem.* 270:7495-7500, American Society for Biochemistry and Molecular Biology, Bethesda, MD (1995).

Zhu, Z., et al., "Epiregulin Is Up-Regulated in Pancreatic Cancer and Stimulates Pancreatic Cancer Cell Growth," *Biochem. Biophys. Res. Commun.* 273:1019-1024, Academic Press, Burlington, MA (2000).

International Search Report for International Patent Application No. PCT/JP2007/069988, filed Oct. 12, 2007, mailed on Nov. 20, 2007, Japanese Patent Office, Tokyo, Japan (Not a Counterpart Application).

Koo, B.-H. and Kim, D.-S., "Factor Xa Induces Mitogenesis of Vascular Smooth Muscle Cells via Autocrine Production of Epiregulin," *J. Biol. Chem.* 278(52):52578-52586, The American Society for Biochemistry and Molecular Biology, Inc., United States (2003).

Friedberg, J.W., "Unique Toxicities and Resistance Mechanisms Associated with Monoclonal Antibody Therapy," *Hematology 2005*:329-334, American Society of Hematology (2005).

Dean. C., et al., "Immunotherapy With Antibodies to the EGF Receptor," *Int. J. Cancer Supplement* 8:103-107, Wiley-Liss, Inc., United States (1994).

Force, T., et al., "Molecular mechanisms of cardiotoxicity of tyrosine kinase inhibition," *Nature Reviews Cancer* 7:332-334, Nature Publishing Group, England (2007).

Higashiyama, S., et al., "Membrane-anchored growth factors, the epidermal growth factor family: Beyond receptor ligands," *Cancer Sci.* 99(2):214-220, Japanese Cancer Association, Japan (2008).

Ito, M., et al., "Expression of several growth factors and their receptor genes in human colon carcinomas," *Virchows Archiv B Cell Pathol.* 59:173-178, Springer-Verlag, Germany (1990).

Johnson, G.R., et al., "Autocrine Action of Amphiregulin in a Colon Carcinoma Cell Line and Immunocytochemical Localization of Amphiregulin in Human Colon," *J. Cell Biol.* 118(3):741-751, The Rockefeller University Press, United States (1992).

Lacouture, M.E., "Mechanisms of cutaneous toxicities to EGFR inhibitors," *Nature Reviews Cancer* 6:803-812, Nature Publishing Group, England (2006).

Lu, Y., et al., "Immunogene Therapy of Tumors with Vaccine Based on Xenogenic Epidermal Growth Factor Receptor," *J. Immunol.* 170:3162-3170, The American Association of Immunologists, Inc., United States (2003).

Modjtahedi, H., et al., "Anti-EGFR Monoclonal Antibodies Which Act As EGF, TGFα, HB-EGF and BTC Antagonists Block the Binding of Epiregulin to EGFR-Expressing Tumors," *Int. J. Cancer* 75:310-316, Wiley-Liss, Inc., United States (1998).

Qian, J.F., et al., "Human transforming growth factor alpha: sequence analysis of the 4.5-kb and 1.6-kb mRNA species," *Gene* 132:291-296, Elsevier Science Publishhers B.V., Netherlands (1993).

Schneider, M.R. and Wolf, E., "The Epidermal Growth Factor Receptor Ligands at a Glance," *J. Cell Physiol.* 218:460-466, Wiley-Liss, Inc., United States (2008).

Seth, D., et al., "Complex post-transcriptional regulation of EGF-receptor expression by EGF and TGF-α in human prostate cancer cells," *Br. J. Cancer* 80(5/6):657-669, Cancer Research Campaign, England (1999).

Tejpar, S., et al., "Magnesium wasting associated with epidermal-growth-factor receptor-targeting antibodies in colorectal cancer: a prospective study," *Lancet Oncol.* 8:387-394, Lancet Publishing Group, England (2007).

(56) References Cited

OTHER PUBLICATIONS

Tiel Groenestege, W.M., et al., "Impaired basolateral sorting of pro-EGF causes isolated recessive renal hypomagnesemia," *J. Clin. Invest.* 117(8):2260-2267, American Society for Clinical Investigation, United States (2007).

Willmarth, N.E., and Ethier, S.P., "Autocrine and Juxtacrine Effects of Amphiregulin on the Proliferative, Invasive, and Migratory Properties of Normal and Neoplastic Human Mammary Epithelial Cells," *J. Biol. Chem.* 281(49):37728-37737, The American Society for Biochemistry and Molecular Biology, Inc., United States (2006).

Wilson, K.J., et al., "Functional selectivity of EGF family peptide growth factors: Implications for cancer," *Pharmacol. Ther.* 122(1):1-8, Elsevier B.V., Netherlands (2009).

Unverified English language translation of WO 2008/047723 A1, published Jun. 24, 2008.

Nicholson, B.E. et al., "Profiling the Evolution of Human Metastatic Bladder Cancer," *Cancer Res.* 64:7813-7821, American Association for Cancer Research, United States (2004).

Kurachi, H. et al., "Importance of Transforming Growth Factor α/Epidermal Growth Factor Receptor Autocrine Growth Mechanism in an Ovarian Cancer Cell Line in Vivo," *Cancer Res.* 51:5956-5959, American Association for Cancer Research, United States (1991).

Zhang, J. et al., "Intratumoral Epiregulin Is a Marker of Advanced Disease in Non-Small Lung Cancer Patients and Confers Invasive Properties on EGFR-Mutant Cells," *Cancer Prev. Res.* 1(3):201-207, American Association for Cancer Research, United States (2008).

Normanno, N. et al., "Target-based agents against ErbB receptors and their ligands: a novel approach to cancer treatment," *Endocrine-Related Cancer* 10:1-21, Society for Endocrinology, United Kingdom (2003).

Tamura, M. et al., "Structural Correlates of an Anticarcinoma Antibody: Identification of Specificity-Determining Residues (SDRs) and Development of a Minimally Immunogenic Antibody Variant by Retention of SDRs Only," *J. Immunol.* 164:1432-1441, The American Association of Immunologists (2000).

Sato, K., et al., "Solution structure of epiregulin and the effect of its C-terminal domain for receptor binding affinity," *FEBS Letters* 553:232-238, Elsevier Science B.V., Netherlands (2003).

Kairemo, K.J.A., "Positron Emission Tomography of Monoclonal Antibodies," *Acta Oncol.* 32:825-830, Informa Healthcare, London (1993).

NCBI GenBank Accession No. AAX36706, Hines, L., et al., Entry Date Mar. 16, 2005.

NCBI GenBank Accession No. AAF61510, Cassady-Cain, R.L. and Kaushik, A.K., Entry Date May 2, 2006.

NCBI GenBank Accession No. AAR90995, Liang, Z., et al., Entry Date Mar. 15, 2004.

Unverified English language translation of Asano, R., et al., "The Advance on the Antibody Therapy—the Expectation to the Clinical Application," *Igaku no Ayumi* 211:723-727, Maruzen Co Ltd., Tokyo, Japan (2004).

Unverified English language translation of Sunanaga, N., et al., "Haigan ni okeru Epiregulin Idenshi no Hatsugen ni tsuite no Kento," *The Journal of the Japanese Respiratory Society* 45:167, The Japanese Respiratory Society, Japan (2007).

Bugelski, P.J., et al., "Preclinical development of keliximab, a Primatized anti-CD4 monoclonal antibody, in human CD4 transgenic mice: characterization of the model and safety studies," *Human & Experiemental Toxicology*, 19:230-243, Nature America, Inc., United States (2000).

Sandusky, G.E., et al., "Use of Monoclonal Antibodies to Human Lymphocytes to Identify Lymphocyte Subsets in Lymph Nodes of the Rhesus Monkey and the Dog," *J. Med. Primatol* 15:441-451, Alan R. Liss, Inc., United States (1986).

Schlereth, B., et al., "T-cell activation and B-cell depletion in chimpanzees treated with a bispecific anti-CD19/anti CD3 single-chain antibody construct," *Cancer Immunol Immunother* 55:503-514, Springer-Verlag, Germany (2006).

Uda, A., et al., "CD3 polymorphism in cynomolgus monkeys (*Macaca fascicularis*)," *J. Med. Primatol*, 30:141-147, Munksgaard, Copenhagen, Denmark (2001).

International Search Report for International Patent No. PCT/JP2012/084042, filed Dec. 28, 2012, mailed on Feb. 5, 2013, Japanese Patent Office, Tokyo, Japan.

Beckman, R. A., et al., "Antibody Constructs in Cancer Therapy," *Cancer* 109(2):170-179, American Cancer Society, United States (2007).

Bischoff, R. and Kolbe, H.V., "Deamidation of asparagine and glutamine residues in proteins and peptides: structural determinants and analytical methodology," *Journal of Chromatography B* 662:261-278, Elsevier Science B.V., Netherlands (1994).

Blanche, F., et al,, "Stabilization of Recombinant Adenovirus: Site-Directed Mutagenesis of Key Aspargine Residues in the Hexon Protein," *Analytical Biochemistry* 297(1):1-9, Academic Press, United States (2001).

Brorson, K., et al., "Mutational Analysis of Avidity and Fine Specificity of Anti-Levan Antibodies," *The Journal of Immunology* 163(12):6694-6701, The American Association of Immunologists (1999).

Brummell, D.A., et al., "Probing the combining site of an anti-carbohydrate antibody by saturation-mutagenesis: role of the heavy-chain CDR3 residues," *Biochemistry* 32(4):1180-1187, American Chemical Society, United States (1993) (Abstract).

Burks, E.A., et al., "In vitro scanning saturation mutagenesis of an antibody binding pocket," *Proc Natl Acad Sci USA* 94:412-417, The National Academy of Sciences of the USA (1997).

Cacia, J., et al., "Isomerization of an Aspartic Acid Residue in the Complementarity-Determining Regions of a Recombinant Antibody to Human IgE: Identification and Effect on Binding Affinity," *Biochemistry* 35:1897-1903, American Chemical Society (1996).

Casset, F., et al., "A peptide mimetic of an anti-CD4 monoclonal antibody by rational design," *Biochemical and Biophysical Research Communications* 307:198-205, Elsevier Science, United States (2003).

Céspedes, M.V., et al., "Mouse models in oncogenesis and cancer therapy," *Clin Transl Oncol* 8(5):318-329, Springer Italia, Italy (2006).

Chen, Y., et al., "Selection and Analysis of an Optimized Anti-VEGF Antibody: Crystal Structure of an Affinity-matured Fab in Complex with Antigen," *J Mol Biol* 293:865-881, Academic Press, United States (1999).

Chothia, C. and Lesk, A.M., "Canonical Structures for the Hypervariable Regions of Immunoglobulins,"*J Mol Biol* 196:901-917, Academic Press, United States (1987).

Chothia, C., et al., "Structural Repertoire of the Human $V_H$ Segments," *J Mol Biol* 227(3):799-817, Academic Press, United States (1992).

Colman, P.M., "Effects of amino acid sequence changes on antibody-antigen interactions," *Research in Immunology* 145:33-36, Elsevier Science, United States (1994).

Dennis, C., "Cancer: Off by a whisker," *Nature* 442:739-741, Nature Publishing Group, England (2006).

De Pascalis, R., et al., "Grating of 'Abbreviated' Complementarity-Determining Regions Containing Specificity-Determining Residues Essential for Ligand Contact to Engineer a Less Immunogenic Humanized Monoclonal Antibody," *The Journal of Immunology* 169:3076-3084, The American Association of Immunologists, United States (2002).

Flessner, M.F., et al., "Resistance of Tumor Interstitial Pressure to the Penetration of Intraperitoneally Delivered Antibiodies into Metastatic Ovarian Tumors," *Clin Cancer Res* 11:3117-3125, American Association for Cancer Research (2005).

Fujimori, K., et al., "A Modeling Analysis of Monoclonal Antibody Percolation Through Tumors: A Binding-Site Barrier," *J Nucl Med* 31:1191-1198, Society of Nuclear Medicine, United States (1990).

Geiger, T. and Clarke, S., "Deamidation, Isomerization, and Racemization at Asparaginyl and Aspartyl Residues in Peptides," *The Journal of Biological Chemistry* 262(2):785-794, The American Society of Biological Chemists, Inc., United States (1987).

Goolcharran, C., et al., "The Effects of a Histidine Residue on the C-Terminal Side of Asparaginyl Residue on the Rate of Deamida-

(56) References Cited

OTHER PUBLICATIONS tion Using Model Pentapeptides," *Journal of Pharmaceuitical Sciences* 89(6):818-825, Wiley-Liss, United States (2000).

Harris, R.J., et al., "Identification of multiple sources of charge heterogeneity in a recombinant antibody," *Journal of Chromatography B* 752:233-245, Elsevier Science B.V., Netherlands (2001).

Holm, P., et al., "Functional mapping and single chain construction of the anti-cytokeratin 8 monoclonal antibody TS1," *Molecular Immunology* 44:1075-1084, Elsevier Ltd., England (2007).

Jain, R.K., "Physiological Barriers to Delivery of Monoclonal Antibodies and Other Macromolecules in Tumors," *Cancer Res* 50:814s-819s, American Association for Cancer Research (1990).

Jang, J.-Y., et al., "The structural basis for DNA binding by an anti-DNA autoantibody," *Molecular Immunology* 35:1207-1217, Pergamon, England (1998).

Kobayaski, H., et al., "Tryptophan H33 plays an important role in pyrimidine (6-4) pyrimidone photoproduct binding by a high-affinity antibody," *Protein Engineering* 12(10):879-884, Oxford University Press, England (1999).

Kumar, S., et al., "Molecular Cloning and Expression of the Fabs of Human Autoantibodies in *Escherichia coli,*" *The Journal of Biological Chemistry* 275(45):35129-35136, The American Society for Biochemistry and Molecular Biology, Inc., United States (2000).

Kuntz, E., et al., "Effect of epiregulin on pancreatic beta cell growth and insulin secretion," *Growth Factors* 23(4):285-293, Harwood Academic Publishers, England (2005) (Abstract).

MacCallum, R.M., et al., "Anitbody-antigen Interactions: Contact Analysis and Binding Site Topography," *J Mol Biol* 262:732-745, Academic Press Limited, United States (1998).

Manning, M.C., et al., "Stability of Protein Pharmaceuticals," *Pharmaceutical Research* 6(11):903-918, Kluwer Academic/Plenum Publishers, United States (1989).

NCBI Reference Sequence, Accession No. NP_001423, "epiregulin", Entry Date Apr. 2005.

Robinson, N.E. and Robinson, A.B., "Molecular clocks," *PNAS* 98(3):944-949, National Academy of Sciences, United States (2001).

Robinson, N.E. and Robinson, A.B., "Deamidation of human proteins," *PNAS* 98(22):12409-12413, National Academy of Sciences, United States (2001).

Rudikoff, S., et al., "Single amino acid substitution altering antigen-binding speficity," *PNAS* 79:1979-1983, National Academy of Sciences, United States (1982).

Rudnick, S.I. and Adams, G.P., "Affinity and Avidity in Antibody-Based Tumor Targeting," *Cancer Biotherapy and Radiopharmaceuticals* 24(2):155-161, Mary Ann Liebert, Inc, United States (2009).

Scotchler, J.W. and Robinson, A.B., "Deamidation of Glutaminyl Residues: Dependence on pH, Temperature, and Ionic Strength," *Analytical Biochemistry* 59:319-322, Academic Press, Inc., United States (1974).

Smith-Gill, S.J., et al., "Contributions of Immunoglobulin Heavy and Light Chains to Antibody Specificity for Lysozyme and Two Haptens," *The Journal of Immunology* 139:4135-4144, The American Association of Immunologists (1987).

Song, M-K., et al., "Light Chain of Natural Antibody Plays a Dominant Role in Protein Antigen Binding," *Biochemical and Biophysical Research Communications* 268:390-394, Academic Press, United States (2000).

Spinelli, G.P., et al., "Long-Term Survival in Metastatic Pancreatic Cancer. A Case Report and Review of the Literature," *J Pancreas (Online)* 7(5):486-491, E.S. Burioni Ricerche Bibliografiche, Italy (2006).

Sugo, I., et al., "Study on structural properties of antibody pharmaceuticals (3)—Activity Reduction Cause by Deamidation of Asn Residues and Molecular Design for Preventing the Reduction," Proc. 124th Ann. Meeting Pharmacol. Soc. Japan (Nihon Yakugakukai Dai124nenki Osaka 2004 youshishyu), 30[p. 2]III-389, p. 103 (Mar. 5, 2004) (Translation Included).

Talmadge, J.E., et al., "Murine Models to Evaluate Novel and Conventional Therapeutic Strategies for Cancer," *The American Journal of Pathology* 170(3):793-804, The American Society for Investigative Pathology, United States (2007).

Thurber, G.M., et al., "Antibody tumor penetration: Transport opposed by systemic and antigen-mediated clearance," *Advanced Drug Delivery Reviews* 60:1421-1434, Elsevier B.V., Netherlands (2008).

Tomizawa, H., et al., "Stabilization of lysozyme against irreversible inactivation by alterations of the Asp-Gly sequences," *Protein Engineering* 8(10):1023-1028, Oxford University Press, England (1995).

Tyler-Cross, R. and Schirch, V. "Effects of Amino Acid Sequence, Buffers, and Ionic Strength on the Rate and Mechanism of Deamidation of Asparagine Residues in Small Peptides," *The Journal of Biological Chemistry* 266(33):22349-22556, The American Society for Biochemistry and Molecular Biology, Inc., United States (1991).

Vajdos, F.F., et al., "Comprehensive Functional Maps of the Antigen-binding Site of an Anti-ErbB2 Antibody Obtained with Shotgun Scanning Mutagenesis," *J Mol Biol* 320:415-428, Elsevier Science Ltd., England (2002).

Voskoglou-Nomikos, T., et al., "Clinical Predictive Value of the in Vitro Cell Line, Human Xenograft, and Mouse Allograft Preclinical Cancer Models," *Clinical Cancer Research* 9:4227-4239, The American Association for Cancer Research, United States (2003).

Ward, E.S., et al., "Binding activities of a repertoire of single immunoglobulin variable domains secreted from *Escherichia coli,*" *Nature* 341:544-546, Nature Publishing Group, England (1989).

Wu, H. et al., "Humanization of a Murine Monoclonal Antibody by Simultaneous Optimization of Framework and CDR Residues," *J Mol Biol* 294:151-162, Academic Press, United States (1999).

Nautiyal, J. et al., "Targeting EGFRs and Src signaling with a modified ectodomain of human EGFR (EBIP) and dasatinib in breast cancer," *Cancer Research* 69(2) Suppl 1:3069, American Association for Cancer Research, United States (2008) (Abstract #3069).

Perkins, M. et al., "Determination of the Origin of Charge Heterogeneity in a Murine Monoclonal Antibody," *Pharmaceutical Research* 17(9):1110-1117, Plenum Publishing Corporation, United States (2000).

International Preliminary Report on Patentability of the International Searching Authority for International Application No. PCT/JP2007/069988, mailed on Apr. 28, 2009, The International Bureau of WIPO, Switzerland (Not a Corresponding Application).

International Preliminary Report on Patentability of the International Searching Authority for International Application No. PCT/JP2010/059008, mailed on Jul. 6, 2010, The International Bureau of WIPO, Switzerland (Not a Corresponding Application).

International Search Report for International Application No. PCT/JP2010/059008, mailed on Jul. 6, 2010, Japanese Patent Office, Tokyo Japan (Not a Corresponding Application).

Supplementary European Search Report in European Patent Application No. 07 82 9724, mailed on Jul. 29, 2010, European Patent Office, Munich, Germany (Not a Corresponding Application).

Co-pending Application, U.S. Appl. No. 14/873,861 inventors Yoshida et al., filed Oct. 2, 2015 (Not Yet Published).

An, S.-J., et al., "Identification of Enriched Driver Gene Alterations in Subgroups of Non-Small Cell Lung Cancer Patients Based on Histology and Smoking Status," *PLoS One* 7(6):e40109, 13 pages, Open Access Article (2012).

International Search Report for International Application No. PCT/JP2014/066512, Japanese Patent Office, Japan, mailed on Aug. 12, 2014, 2 pages (Not a Corresponding Application).

Gold, K.A., "New Strategies in Squamous Cell Carcinoma of the Lung: Identification of Tumor Drivers to Personalize Therapy," *Clinical Cancer Research* 18(11):3002-3007, American Association for Cancer, United States (2012).

Langer, C.J., et al., "The Evolving Role of Histology in the Management of Advanced Non-Small-Cell Lung Cancer," *Journal of Clinical Oncology* 28(36):5311-5320, American Society of Clinical Oncology, United States (2010).

(56) References Cited

OTHER PUBLICATIONS

Pennell, N.A., "Selection of chemotherapy for patients with advanced non-small cell lung cancer," *Cleveland Clinic Journal of Medicine* 79:e-S46-e-S50, Cleveland Clinic Educational Foundation, United States (2012).

Sandler, A., et al., "Treatment Outcomes by Tumor Histology in Eastern Cooperative Group Study E4599 of Bevacizumab with Paclitaxel/Carboplatin for Advanced Non-small Cell Lung Cancer," *Journal of Thoracic Oncology* 5(9):1416-1423, International Association for the Study of Lung Cancer, United States (2010).

Co-Pending U.S. Appl. No. 14/900,928, inventors Suzuki, Masami, et al., Int'l filing date of Jun. 23, 2014 (Not Yet Published).

Beidler, C.B., et al., "Generation and Activity of a Humanized Monoclonal Antibody That Selectively Neutralizes the Epidermal Growth Factor Receptor Ligands Transforming Growth Factor-α and Epiregulin," *The Journal of Pharmacology and Experimental Therapeutics* 349:330-343, The American Society for Pharmacology and Experimental Therapeutics, United States (2014).

Imanishi, K.-I., et al., "Inhibition of Growth of Human Lung Adenocarcinoma Cell Lines by Anti-Transforming Growth Factor-α Monoclonal Antibody," *Journal of National Cancer Institute* 81:220-223, Oxford University Press, United States (1989).

Jonker, D.J., et al., "Cetuximab for the Treatment of Colorectal Cancer," *The New England Journal of Medicine* 357:2040-2048, Massachusetts Medical Society, United States (2007).

Peggs, K.S., et al., "Cancer immunotherapy: co-stimulatory agonists and co-inhibitory antagonists," *Clinical and Experimental Immunology* 157:9-19, British Society for Immunology, England (2009).

Spano, J.P., et al., "Epidermal growth factor receptor signaling in colorectal cancer: preclinical data and therapeutic perspectives," *Annals of Oncology* 16:189-194, European Society for Medical Oncology, Switzerland (2005).

"Antibody Structure and Function," in *Immunology*, Fifth Edition, Roitt, et al., Eds., pp. 110-111, C.V. Mosby Co., United States (1998).

"Antibody Structure and Function," in *Immunology*, Fifth Edition, Roitt, et al., Eds., pp. 80-81, C.V. Mosby Co., United States (1998).

Imai-Nishiya, H., et al., "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnology 7:84, BioMed Central Ltd., United Kingdom (2007).

Schildbach, J.F., et al., "Modulation of antibody affinity by a non-contact residue," *Protein Science* 2:206-214, Cambridge University Press, United States (1993).

LANE 1: MOLECULAR MARKER
LANE 2: HUMAN MATURE EREG (ELUTION FRACTION 1)
LANE 3: HUMAN MATURE EREG (ELUTION FRACTION 2)
LANE 4: CYNOMOLGUS MATURE EREG (ELUTION FRACTION 1)
LANE 5: CYNOMOLGUS MATURE EREG (ELUTION FRACTION 2)

SEQUENCE LISTING

```
<160> NUMBER OF SEQ ID NOS: 171

<210> SEQ ID NO 1
<211> LENGTH: 30
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 2
<211> LENGTH: 14
<212> TYPE: PRT
<213> ORGANISM: Homo sapiens

<400> SEQUENCE: 2

Trp Val Arg Gln Ala Pro Gly Gln Gly Leu Glu Trp Met Gly
1               5                   10

<210> SEQ ID NO 3
<211> LENGTH: 32
<212> TYPE: PRT
<213> ORGANISM: Homo sapiens

<400> SEQUENCE: 3

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 4
<211> LENGTH: 11
<212> TYPE: PRT
<213> ORGANISM: Homo sapiens

<400> SEQUENCE: 4

Trp Gly Gln Gly Thr Leu Val Thr Val Ser Ser
1               5                   10

<210> SEQ ID NO 5
<211> LENGTH: 23
```

```
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 6
<211> LENGTH: 15
<212> TYPE: PRT
<213> ORGANISM: Homo sapiens

<400> SEQUENCE: 6

Trp Tyr Gln Gln Lys Pro Gly Gln Ala Pro Arg Leu Leu Ile Tyr
1               5                   10                  15

<210> SEQ ID NO 7
<211> LENGTH: 32
<212> TYPE: PRT
<213> ORGANISM: Homo sapiens

<400> SEQUENCE: 7

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 8
<211> LENGTH: 10
<212> TYPE: PRT
<213> ORGANISM: Homo sapiens

<400> SEQUENCE: 8

Phe Gly Gly Gly Thr Lys Val Glu Ile Lys
1               5                   10

<210> SEQ ID NO 9
<211> LENGTH: 5
<212> TYPE: PRT
<213> ORGANISM: Mus Musculus

<400> SEQUENCE: 9

Asp Thr Tyr Ile Gln
1               5

<210> SEQ ID NO 10
<211> LENGTH: 17
<212> TYPE: PRT
<213> ORGANISM: Mus Musculus

<400> SEQUENCE: 10

Arg Ile Asp Pro Leu Asn Gly Asn Thr Lys Tyr Val Pro Lys Phe Gln
1               5                   10                  15

Gly

<210> SEQ ID NO 11
<211> LENGTH: 7
<212> TYPE: PRT
<213> ORGANISM: Mus Musculus

<400> SEQUENCE: 11
```

```
Ser Gly Thr Leu Phe Asp Phe
1               5

<210> SEQ ID NO 12
<211> LENGTH: 11
<212> TYPE: PRT
<213> ORGANISM: Mus Musculus

<400> SEQUENCE: 12

Lys Ala Ser Gln Asp Ile His Lys Tyr Ile Ala
1               5                   10

<210> SEQ ID NO 13
<211> LENGTH: 7
<212> TYPE: PRT
<213> ORGANISM: Mus Musculus

<400> SEQUENCE: 13

Tyr Thr Ser Thr Leu Gln Pro
1               5

<210> SEQ ID NO 14
<211> LENGTH: 8
<212> TYPE: PRT
<213> ORGANISM: Mus Musculus

<400> SEQUENCE: 14

Leu Gln Tyr Asp Asn Leu Arg Thr
1               5

<210> SEQ ID NO 15
<211> LENGTH: 116
<212> TYPE: PRT
<213> ORGANISM: Artificial
<220> FEATURE:
<223> OTHER INFORMATION: An artificially synthesized peptide sequence

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Thr Leu Phe Asp Phe Trp Gly Gln Gly Thr Leu Val
            100                 105                 110

Thr Val Ser Ser
        115

<210> SEQ ID NO 16
<211> LENGTH: 106
<212> TYPE: PRT
<213> ORGANISM: Artificial
<220> FEATURE:
<223> OTHER INFORMATION: An artificially synthesized peptide sequence

<400> SEQUENCE: 16
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
            35                  40                  45

Tyr Tyr Thr Ser Thr Leu Gln Pro Gly Val Pro Ser Arg Phe Ser Gly
50                      55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys
            100                 105

<210> SEQ ID NO 17
<211> LENGTH: 30
<212> TYPE: PRT
<213> ORGANISM: Homo sapiens

<400> SEQUENCE: 17

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys
            20                  25                  30

<210> SEQ ID NO 18
<211> LENGTH: 32
<212> TYPE: PRT
<213> ORGANISM: Homo sapiens

<400> SEQUENCE: 18

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Val Arg
            20                  25                  30

<210> SEQ ID NO 19
<211> LENGTH: 116
<212> TYPE: PRT
<213> ORGANISM: Artificial
<220> FEATURE:
<223> OTHER INFORMATION: An artificially synthesized peptide sequence

<400> SEQUENCE: 19

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
            35                  40                  45

Gly Arg Ile Asp Pro Leu Asn Gly Asn Thr Lys Tyr Val Pro Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
```

```
                   100                 105                 110
Thr Val Ser Ser
        115

<210> SEQ ID NO 20
<211> LENGTH: 15
<212> TYPE: PRT
<213> ORGANISM: Homo sapiens

<400> SEQUENCE: 20

Trp Tyr Gln Gln Lys Pro Gly Gln Ala Pro Arg Leu Leu Ile Gln
1               5                   10                  15

<210> SEQ ID NO 21
<211> LENGTH: 32
<212> TYPE: PRT
<213> ORGANISM: Homo sapiens

<400> SEQUENCE: 21

Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Tyr Cys
            20                  25                  30

<210> SEQ ID NO 22
<211> LENGTH: 106
<212> TYPE: PRT
<213> ORGANISM: Artificial
<220> FEATURE:
<223> OTHER INFORMATION: An artificially synthesized peptide sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys
            100                 105

<210> SEQ ID NO 23
<211> LENGTH: 32
<212> TYPE: PRT
<213> ORGANISM: Homo sapiens

<400> SEQUENCE: 23

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 24
<211> LENGTH: 106
<212> TYPE: PRT
```

<213> ORGANISM: Artificial
<220> FEATURE:
<223> OTHER INFORMATION: An artificially synthesized peptide sequence

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Asn Leu Arg Thr
                85                  90                  95

Phe Gly Gly Gly Thr Lys Val Glu Ile Lys
            100                 105

<210> SEQ ID NO 25
<211> LENGTH: 330
<212> TYPE: PRT
<213> ORGANISM: Homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 328
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 27
<211> LENGTH: 107
<212> TYPE: PRT
<213> ORGANISM: Homo sapiens

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 28

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 29
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
            35                  40                  45

Gln Tyr Thr Ser Thr Leu Gln Pro Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

-continued

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 30
<211> LENGTH: 328
<212> TYPE: PRT
<213> ORGANISM: Homo sapiens

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu

```
                225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 31
<211> LENGTH: 328
<212> TYPE: PRT
<213> ORGANISM: Homo sapiens

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 32
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 32

Glu Asp Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile Gln Trp Val Lys Leu Arg Pro Glu Gln Gly Leu Glu Trp Ile
        35                  40                  45

Gly Arg Ile Asp Pro Leu Asn Gly Asn Thr Lys Tyr Val Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Ser Gly Thr Leu Phe Asp Phe Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 33
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 33

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile His Lys Tyr
            20                  25                  30

Ile Ala Trp Tyr Gln His Lys Pro Gly Lys Gly Pro Arg Leu Leu Ile
        35                  40                  45

Gln Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 34
<211> LENGTH: 46
<212> TYPE: PRT
<213> ORGANISM: Homo sapiens

<400> SEQUENCE: 34

Val Ser Ile Thr Lys Cys Ser Ser Asp Met Asn Gly Tyr Cys Leu His
1               5                   10                  15

Gly Gln Cys Ile Tyr Leu Val Asp Met Ser Gln Asn Tyr Cys Arg Cys
            20                  25                  30

Glu Val Gly Tyr Thr Gly Val Arg Cys Glu His Phe Phe Leu
        35                  40                  45

<210> SEQ ID NO 35
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 35

Arg Val Thr Ile Thr Ala Asp Thr Ser Ser Asn Thr Ala Tyr Met Glu
1               5                   10                  15

Leu Ser Ser Leu Arg Ser Glu Asp Thr Ala Val Tyr Tyr Cys Val Arg
            20                  25                  30

<210> SEQ ID NO 36
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 36

Arg Val Thr Ile Thr Ala Asp Thr Ser Thr Asn Thr Ala Tyr Met Glu
1               5                   10                  15

Leu Ser Ser Leu Arg Ser Glu Asp Thr Ala Val Tyr Tyr Cys Val Arg
            20                  25                  30

<210> SEQ ID NO 37
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 37

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Lys Phe
    50                  55                  60

Gln Gly Arg Val Thr Ile Thr Ala Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 38
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 38

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

-continued

```
Tyr Ile Gln Trp Val Arg Gln Ala Pro Gly Gln Gly Leu Glu Trp Met
         35                  40                  45

Gly Arg Ile Asp Pro Leu Asn Gly Asn Thr Lys Tyr Val Pro Lys Phe
 50                  55                  60

Gln Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Thr Leu Phe Asp Phe Trp Gly Gln Gly Thr Leu Val
             100                 105                 110

Thr Val Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
 130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
         195                 200                 205

Lys Val Asp Lys Lys Val Glu Pro Lys Ser Cys Asp Lys Thr His Thr
 210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser His Glu Asp Pro Glu Val
             260                 265                 270

Lys Phe Asn Trp Tyr Val Asp Gly Val Glu Val His Asn Ala Lys Thr
         275                 280                 285

Lys Pro Arg Glu Glu Gln Tyr Asn Ser Thr Tyr Arg Val Val Ser Val
 290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                 325                 330                 335

Lys Ala Lys Gly Gln Pro Arg Glu Pro Gln Val Tyr Thr Leu Pro Pro
             340                 345                 350

Ser Arg Asp Glu Leu Thr Lys Asn Gln Val Ser Leu Thr Cys Leu Val
         355                 360                 365

Lys Gly Phe Tyr Pro Ser Asp Ile Ala Val Glu Trp Glu Ser Asn Gly
 370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                 405                 410                 415

Gln Gln Gly Asn Val Phe Ser Cys Ser Val Met His Glu Ala Leu His
             420                 425                 430

Asn His Tyr Thr Gln Lys Ser Leu Ser Leu Ser Pro
         435                 440
```

```
<210> SEQ ID NO 39
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 39

Ala Thr Tyr Ile Gln
1               5

<210> SEQ ID NO 40
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 40

Arg Ile Asp Pro Leu Thr Gly Asn Thr Lys Tyr Val Pro Lys Phe Gln
1               5                   10                  15

Gly

<210> SEQ ID NO 41
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 41

Arg Ile Asp Pro Leu Lys Gly Asn Thr Lys Tyr Val Pro Lys Phe Gln
1               5                   10                  15

Gly

<210> SEQ ID NO 42
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 42

Arg Ile Asp Pro Leu Phe Gly Asn Thr Lys Tyr Val Pro Lys Phe Gln
1               5                   10                  15

Gly

<210> SEQ ID NO 43
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 43

Arg Ile Asp Pro Leu Val Gly Asn Thr Lys Tyr Val Pro Lys Phe Gln
1               5                   10                  15

Gly

<210> SEQ ID NO 44
<211> LENGTH: 17
<212> TYPE: PRT
<213> ORGANISM: Artificial
<220> FEATURE:
```

```
<223> OTHER INFORMATION: An artificially synthesized peptide sequence

<400> SEQUENCE: 44

Arg Ile Asp Pro Leu Leu Gly Asn Thr Lys Tyr Val Pro Lys Phe Gln
1               5                   10                  15

Gly

<210> SEQ ID NO 45
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 45

Arg Ile Asp Pro Leu Asn Gly Ser Thr Lys Tyr Val Pro Lys Phe Gln
1               5                   10                  15

Gly

<210> SEQ ID NO 46
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 46

Arg Ile Asp Pro Leu Asn Gly Gln Thr Lys Tyr Val Pro Lys Phe Gln
1               5                   10                  15

Gly

<210> SEQ ID NO 47
<211> LENGTH: 8
<212> TYPE: PRT
<213> ORGANISM: Artificial
<220> FEATURE:
<223> OTHER INFORMATION: An artificially synthesized peptide sequence

<400> SEQUENCE: 47

Leu Gln Tyr Glu Asn Leu Arg Thr
1               5

<210> SEQ ID NO 48
<211> LENGTH: 8
<212> TYPE: PRT
<213> ORGANISM: Artificial
<220> FEATURE:
<223> OTHER INFORMATION: An artificially synthesized peptide sequence

<400> SEQUENCE: 48

Leu Gln Tyr Glu Gln Leu Arg Thr
1               5

<210> SEQ ID NO 49
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 49

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Ala Thr
```

-continued

```
               20                  25                  30
    Tyr Ile Gln Trp Val Arg Gln Ala Pro Gly Gln Gly Leu Glu Trp Met
                35                  40                  45
    Gly Arg Ile Asp Pro Leu Asn Gly Asn Thr Lys Tyr Val Pro Lys Phe
     50                  55                  60
    Gln Gly Arg Val Thr Ile Thr Ala Asp Thr Ser Asn Thr Ala Tyr
     65                  70                  75                  80
    Met Glu Leu Ser Ser Leu Arg Ser Glu Asp Thr Ala Val Tyr Tyr Cys
                    85                  90                  95
    Val Arg Ser Gly Thr Leu Phe Asp Phe Trp Gly Gln Gly Thr Leu Val
                   100                 105                 110
    Thr Val Ser Ser Ala Ser Thr Lys Gly Pro Ser Val Phe Pro Leu Ala
                   115                 120                 125
    Pro Ser Ser Lys Ser Thr Ser Gly Gly Thr Ala Ala Leu Gly Cys Leu
                   130                 135                 140
    Val Lys Asp Tyr Phe Pro Glu Pro Val Thr Val Ser Trp Asn Ser Gly
    145                 150                 155                 160
    Ala Leu Thr Ser Gly Val His Thr Phe Pro Ala Val Leu Gln Ser Ser
                   165                 170                 175
    Gly Leu Tyr Ser Leu Ser Ser Val Val Thr Val Pro Ser Ser Ser Leu
                   180                 185                 190
    Gly Thr Gln Thr Tyr Ile Cys Asn Val Asn His Lys Pro Ser Asn Thr
                   195                 200                 205
    Lys Val Asp Lys Lys Val Glu Pro Lys Ser Cys Asp Lys Thr His Thr
                   210                 215                 220
    Cys Pro Pro Cys Pro Ala Pro Glu Leu Leu Gly Gly Pro Ser Val Phe
    225                 230                 235                 240
    Leu Phe Pro Pro Lys Pro Lys Asp Thr Leu Met Ile Ser Arg Thr Pro
                   245                 250                 255
    Glu Val Thr Cys Val Val Val Asp Val Ser His Glu Asp Pro Glu Val
                   260                 265                 270
    Lys Phe Asn Trp Tyr Val Asp Gly Val Glu Val His Asn Ala Lys Thr
                   275                 280                 285
    Lys Pro Arg Glu Glu Gln Tyr Asn Ser Thr Tyr Arg Val Val Ser Val
                   290                 295                 300
    Leu Thr Val Leu His Gln Asp Trp Leu Asn Gly Lys Glu Tyr Lys Cys
    305                 310                 315                 320
    Lys Val Ser Asn Lys Ala Leu Pro Ala Pro Ile Glu Lys Thr Ile Ser
                   325                 330                 335
    Lys Ala Lys Gly Gln Pro Arg Glu Pro Gln Val Tyr Thr Leu Pro Pro
                   340                 345                 350
    Ser Arg Asp Glu Leu Thr Lys Asn Gln Val Ser Leu Thr Cys Leu Val
                   355                 360                 365
    Lys Gly Phe Tyr Pro Ser Asp Ile Ala Val Glu Trp Glu Ser Asn Gly
                   370                 375                 380
    Gln Pro Glu Asn Asn Tyr Lys Thr Thr Pro Pro Val Leu Asp Ser Asp
    385                 390                 395                 400
    Gly Ser Phe Phe Leu Tyr Ser Lys Leu Thr Val Asp Lys Ser Arg Trp
                   405                 410                 415
    Gln Gln Gly Asn Val Phe Ser Cys Ser Val Met His Glu Ala Leu His
                   420                 425                 430
    Asn His Tyr Thr Gln Lys Ser Leu Ser Leu Ser Pro
                   435                 440
```

```
<210> SEQ ID NO 50
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 50

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Thr Gly Asn Thr Lys Tyr Val Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 51
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 51

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Lys Gly Asn Thr Lys Tyr Val Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 52
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 52

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Phe Gly Asn Thr Lys Tyr Val Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

```
Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
                435                 440

<210> SEQ ID NO 53
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 53

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Val Gly Asn Thr Lys Tyr Val Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125
```

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 54
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 54

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Leu Gly Asn Thr Lys Tyr Val Pro Lys Phe
 50                  55                  60

Gln Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Thr Leu Phe Asp Phe Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 55
<211> LENGTH: 444

```
<212> TYPE: PRT
<213> ORGANISM: Artificial
<220> FEATURE:
<223> OTHER INFORMATION: An artificially synthesized peptide sequence

<400> SEQUENCE: 55

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Ser Thr Lys Tyr Val Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro
        435                 440

<210> SEQ ID NO 56
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 56

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Gln Thr Lys Tyr Val Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
                435                 440

<210> SEQ ID NO 57
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Glu Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 58
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Glu Gln Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 59
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 59

Arg Ile Asp Pro Leu Asn Gly Asn Thr Lys Tyr Val Asp Lys Phe Gln
1               5                   10                  15

Gly

<210> SEQ ID NO 60
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 60

Arg Ile Asp Pro Leu Asn Gly Asn Thr Lys Tyr Val Pro Ser Phe Gln
1               5                   10                  15
```

<210> SEQ ID NO 61
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 61

Arg Ile Asp Pro Leu Asn Gly Asn Thr Lys Tyr Val Pro Gln Phe Gln
1               5                   10                  15
Gly

<210> SEQ ID NO 62
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 62

Arg Ile Asp Pro Leu Asn Gly Asn Thr Lys Tyr Val Pro Lys Phe Asp
1               5                   10                  15
Gly

<210> SEQ ID NO 63
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 63

Arg Ile Asp Pro Leu Asn Gly Asn Thr Lys Tyr Val Pro Lys Phe Glu
1               5                   10                  15
Gly

<210> SEQ ID NO 64
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 64

Arg Ile Asp Pro Leu Asn Gly Asn Thr Lys Tyr Val Pro Lys Phe Gln
1               5                   10                  15
Asp

<210> SEQ ID NO 65
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 65

Arg Ile Asp Pro Leu Asn Gly Asn Thr Lys Tyr Val Pro Lys Phe Gln
1               5                   10                  15
Glu

```
<210> SEQ ID NO 66
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 66

Arg Ile Asp Pro Leu Asn Gly Asn Thr Lys Tyr Val Glu Lys Phe Glu
1               5                   10                  15
Gly

<210> SEQ ID NO 67
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 67

Gln Ala Ser Gln Asp Ile His Lys Tyr Ile Ala
1               5                   10

<210> SEQ ID NO 68
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 68

Ser Ala Ser Gln Asp Ile His Lys Tyr Ile Ala
1               5                   10

<210> SEQ ID NO 69
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 69

Tyr Thr Ser Thr Leu Glu Pro
1               5

<210> SEQ ID NO 70
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 70

Phe Gly Gly Gly Thr Lys Val Glu Ile Glu
1               5                   10

<210> SEQ ID NO 71
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 71

Tyr Thr Ser Thr Leu Gln Glu
1               5
```

```
<210> SEQ ID NO 72
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 72

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Asp Lys Phe
50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
                435                 440
```

<210> SEQ ID NO 73
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 73

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Ser Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 74
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 74

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Gln Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 75
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 75

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Lys Phe
    50                  55                  60

Asp Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 76
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 76

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45
```

Gly Arg Ile Asp Pro Leu Asn Gly Asn Thr Lys Tyr Val Pro Lys Phe
50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
                435                 440

<210> SEQ ID NO 77
<211> LENGTH: 444
<212> TYPE: PRT

<213> ORGANISM: Artificial
<220> FEATURE:
<223> OTHER INFORMATION: An artificially synthesized peptide sequence

<400> SEQUENCE: 77

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Pro Lys Phe
50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
```

```
                385                 390                 395                 400
Gly Ser Phe Phe Leu Tyr Ser Lys Leu Thr Val Asp Lys Ser Arg Trp
                    405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro
                435                 440

<210> SEQ ID NO 78
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 78

Gln Asp Gln Leu Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
            20                  25                  30
Tyr Ile Gln Trp Val Arg Gln Ala Pro Gly Gln Gly Leu Glu Trp Met
        35                  40                  45
Gly Arg Ile Asp Pro Leu Asn Gly Asn Thr Lys Tyr Val Pro Lys Phe
    50                  55                  60
Gln Glu Arg Val Thr Ile Thr Ala Asp Thr Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Val Arg Ser Gly Thr Leu Phe Asp Phe Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
```

```
                305                 310                 315                 320
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
            435                 440

<210> SEQ ID NO 79
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 79

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Val Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
```

```
                225                 230                 235                 240
Leu Phe Pro Pro Lys Pro Lys Asp Thr Leu Met Ile Ser Arg Thr Pro
                    245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                    325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                    405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro
                435                 440

<210> SEQ ID NO 80
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 80

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile His Lys Tyr
                20                  25                  30
Ile Ala Trp Tyr Gln Gln Lys Pro Gly Gln Ala Pro Arg Leu Leu Ile
            35                  40                  45
Gln Tyr Thr Ser Thr Leu Gln Pro Gly Val Pro Ser Arg Phe Ser Gly
        50                  55                  60
Ser Gly Ser Gly Thr Asp Tyr Thr Phe Thr Ile Ser Ser Leu Gln Pro
65                  70                  75                  80
Glu Asp Ile Ala Thr Tyr Tyr Cys Leu Gln Tyr Asp Asn Leu Arg Thr
                85                  90                  95
Phe Gly Gly Gly Thr Lys Val Glu Ile Lys Arg Thr Val Ala Ala Pro
                100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
```

```
            145                 150                 155                 160

Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
                    180                 185                 190

Cys Glu Val Thr His Gln Gly Leu Ser Ser Pro Val Thr Lys Ser Phe
                    195                 200                 205

Asn Arg Gly Glu Cys
            210

<210> SEQ ID NO 81
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile His Lys Tyr
                20                  25                  30

Ile Ala Trp Tyr Gln Gln Lys Pro Gly Gln Ala Pro Arg Leu Leu Ile
            35                  40                  45

Gln Tyr Thr Ser Thr Leu Gln Pro Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
                    180                 185                 190

Cys Glu Val Thr His Gln Gly Leu Ser Ser Pro Val Thr Lys Ser Phe
                    195                 200                 205

Asn Arg Gly Glu Cys
            210

<210> SEQ ID NO 82
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 82

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
            35                  40                  45

Gln Tyr Thr Ser Thr Leu Glu Pro Gly Val Pro Ser Arg Phe Ser Gly
 50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 83
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile His Lys Tyr
            20                  25                  30

Ile Ala Trp Tyr Gln Gln Lys Pro Gly Gln Ala Pro Arg Leu Leu Ile
            35                  40                  45

Gln Tyr Thr Ser Thr Leu Glu Pro Gly Val Pro Ser Arg Phe Ser Gly
 50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 84
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Glu Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 85
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30
```

Ile Ala Trp Tyr Gln Gln Lys Pro Gly Gln Ala Pro Arg Leu Leu Ile
                35                  40                  45

Gln Tyr Thr Ser Thr Leu Gln Glu Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 86
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 86

Ser Gly Thr Ser Phe Asp Phe
1               5

<210> SEQ ID NO 87
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 87

Arg Ile Asp Pro Leu Asn Gly Asn Thr Lys Tyr His Pro Lys Phe Gln
1               5                   10                  15

Gly

<210> SEQ ID NO 88
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 88

Arg Ile Asp Pro Leu Asn Gly Asn Thr Lys Tyr Lys Pro Lys Phe Gln
1               5                   10                  15

Gly

```
<210> SEQ ID NO 89
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 89

Arg Ile Asp Pro Leu Asn Gly Asn Thr Lys Tyr Arg Pro Lys Phe Gln
1               5                   10                  15

Gly

<210> SEQ ID NO 90
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 90

Arg Ile Asp Pro Leu Asn Gly Asn Thr Lys Tyr Ser Pro Lys Phe Gln
1               5                   10                  15

Gly

<210> SEQ ID NO 91
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 91

Arg Ile Asp Pro Leu Asn Gly Asn Thr Lys Tyr Thr Pro Lys Phe Gln
1               5                   10                  15

Gly

<210> SEQ ID NO 92
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 92

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Gln Trp Val Arg Gln Ala Pro Gly Gln Gly Leu Glu Trp Met
            35                  40                  45

Gly Arg Ile Asp Pro Leu Asn Gly Asn Thr Lys Tyr Val Pro Lys Phe
        50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Ser Phe Asp Phe Trp Gly Gln Gly Thr Leu Val
                100                 105                 110

Thr Val Ser Ser Ala Ser Thr Lys Gly Pro Ser Val Phe Pro Leu Ala
            115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 93
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 93

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45
```

Gly Arg Ile Asp Pro Leu Asn Gly Asn Thr Lys Tyr His Pro Lys Phe
 50                  55                  60

Gln Gly Arg Val Thr Ile Thr Ala Asp Thr Ser Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Thr Leu Phe Asp Phe Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 94
<211> LENGTH: 444

```
<212> TYPE: PRT
<213> ORGANISM: Artificial
<220> FEATURE:
<223> OTHER INFORMATION: An artificially synthesized peptide sequence

<400> SEQUENCE: 94

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Lys Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 95
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 95

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Gln Trp Val Arg Gln Ala Pro Gly Gln Gly Leu Glu Trp Met
            35                  40                  45

Gly Arg Ile Asp Pro Leu Asn Gly Asn Thr Lys Tyr Arg Pro Lys Phe
50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro
    435                 440

<210> SEQ ID NO 96
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 96

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Ser Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

-continued

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 97
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 97

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Asn Gly Asn Thr Lys Tyr Thr Pro Lys Phe
50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 98
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 98

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Gln Trp Val Arg Gln Ala Pro Gly Gln Gly Leu Glu Trp Met
            35                  40                  45

Gly Arg Ile Asp Pro Leu Thr Gly Gln Thr Lys Tyr Gln Glu Lys Phe
        50                  55                  60

```
Glu Gly Arg Val Thr Ile Thr Ala Asp Thr Ser Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Thr Ser Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 99
<211> LENGTH: 213
<212> TYPE: PRT
<213> ORGANISM: Artificial
<220> FEATURE:
<223> OTHER INFORMATION: An artificially synthesized peptide sequence
```

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 100
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 100

Arg Ile Asp Pro Leu Arg Gly Asn Thr Lys Tyr Arg Glu Lys Phe Glu
1               5                   10                  15

Gly

<210> SEQ ID NO 101
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 101

Arg Arg Asp Pro Leu Arg Gly Asn Thr Lys Tyr Arg Glu Lys Phe Glu
1               5                   10                  15

Gly

<210> SEQ ID NO 102
<211> LENGTH: 17
<212> TYPE: PRT

```
<213> ORGANISM: Artificial
<220> FEATURE:
<223> OTHER INFORMATION: An artificially synthesized peptide sequence

<400> SEQUENCE: 102

Arg Ile Asp Pro Leu Arg Arg Asn Thr Lys Tyr Arg Glu Lys Phe Glu
1               5                   10                  15
Gly

<210> SEQ ID NO 103
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 103

Arg Ile Asp Pro Leu Arg Gly Arg Thr Lys Tyr Arg Glu Lys Phe Glu
1               5                   10                  15
Gly

<210> SEQ ID NO 104
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 104

Arg Ile Asp Pro Leu Arg Gly Asn Arg Lys Tyr Arg Glu Lys Phe Glu
1               5                   10                  15
Gly

<210> SEQ ID NO 105
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 105

Arg Ile Asp Pro Leu Arg Gly Asn Thr Arg Tyr Arg Glu Lys Phe Glu
1               5                   10                  15
Gly

<210> SEQ ID NO 106
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 106

Arg Ile Asp Pro Leu Arg Gly Asn Thr Lys Arg Arg Glu Lys Phe Glu
1               5                   10                  15
Gly

<210> SEQ ID NO 107
<211> LENGTH: 17
<212> TYPE: PRT
<213> ORGANISM: Artificial
<220> FEATURE:
<223> OTHER INFORMATION: An artificially synthesized peptide sequence
```

```
<400> SEQUENCE: 107

Arg Ile Asp Pro Leu Arg Gly Asn Thr Lys Tyr Arg Glu Arg Phe Glu
1               5                   10                  15

Gly

<210> SEQ ID NO 108
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 108

Arg Ile Asp Pro Leu Arg Gly Asn Thr Lys Tyr Arg Glu Lys Phe Glu
1               5                   10                  15

Arg

<210> SEQ ID NO 109
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 109

Asp Thr Arg Ile Gln
1               5

<210> SEQ ID NO 110
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 110

Ser Arg Thr Leu Phe Asp Phe
1               5

<210> SEQ ID NO 111
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 111

Ser Gly Arg Leu Phe Asp Phe
1               5

<210> SEQ ID NO 112
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 112

Ser Gly Thr Arg Phe Asp Phe
1               5

<210> SEQ ID NO 113
<211> LENGTH: 8
<212> TYPE: PRT
<213> ORGANISM: Artificial
```

```
<220> FEATURE:
<223> OTHER INFORMATION: An artificially synthesized peptide sequence

<400> SEQUENCE: 113

Leu Gln Tyr Asp Arg Leu Arg Thr
1               5

<210> SEQ ID NO 114
<211> LENGTH: 8
<212> TYPE: PRT
<213> ORGANISM: Artificial
<220> FEATURE:
<223> OTHER INFORMATION: An artificially synthesized peptide sequence

<400> SEQUENCE: 114

Leu Gln Tyr Asp Asn Arg Arg Thr
1               5

<210> SEQ ID NO 115
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 115

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Gly Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

-continued

Glu Val Thr Cys Val Val Asp Val Ser His Glu Asp Pro Glu Val
            260             265             270

Lys Phe Asn Trp Tyr Val Asp Gly Val Glu Val His Asn Ala Lys Thr
        275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
        340             345             350

Ser Arg Asp Glu Leu Thr Lys Asn Gln Val Ser Leu Thr Cys Leu Val
    355             360             365

Lys Gly Phe Tyr Pro Ser Asp Ile Ala Val Glu Trp Glu Ser Asn Gly
370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
        420             425             430

Asn His Tyr Thr Gln Lys Ser Leu Ser Leu Ser Pro
    435             440

<210> SEQ ID NO 116
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 116

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Arg Asp Pro Leu Arg Gly Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 117
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 117

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

```
Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 118
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 118

Gln Asp Gln Leu Val Gln Ser Gly Ala Glu Val Lys Lys Pro Gly Ala
1               5                   10                  15
```

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
            35                  40                  45

Gly Arg Ile Asp Pro Leu Arg Gly Arg Thr Lys Tyr Arg Glu Lys Phe
 50                  55                  60

Glu Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro

```
                435               440

<210> SEQ ID NO 119
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 119

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Gly Asn Arg Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
```

```
                355                 360                 365
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
                435                 440

<210> SEQ ID NO 120
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 120

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Gln Trp Val Arg Gln Ala Pro Gly Gln Gly Leu Glu Trp Met
            35                  40                  45

Gly Arg Ile Asp Pro Leu Arg Gly Asn Thr Arg Tyr Arg Glu Lys Phe
        50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
```

```
                    275                 280                 285
Lys Pro Arg Glu Glu Gln Tyr Asn Ser Thr Tyr Arg Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro
        435                 440

<210> SEQ ID NO 121
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 121

Gln Asp Gln Leu Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
            20                  25                  30
Tyr Ile Gln Trp Val Arg Gln Ala Pro Gly Gln Gly Leu Glu Trp Met
        35                  40                  45
Gly Arg Ile Asp Pro Leu Arg Gly Asn Thr Lys Arg Arg Glu Lys Phe
    50                  55                  60
Glu Gly Arg Val Thr Ile Thr Ala Asp Thr Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Val Arg Ser Gly Thr Leu Phe Asp Phe Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
```

-continued

```
            195                 200                 205
Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440
```

<210> SEQ ID NO 122
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 122

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Gly Asn Thr Lys Tyr Arg Glu Arg Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
```

115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 123
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 123

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met

```
             35                  40                  45
Gly Arg Ile Asp Pro Leu Arg Gly Asn Thr Lys Tyr Arg Glu Lys Phe
 50                  55                  60

Glu Arg Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Thr Leu Phe Asp Phe Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 124
```

<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 124

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Arg Ile Gln Trp Val Arg Gln Ala Pro Gly Gln Gly Leu Glu Trp Met
        35                  40                  45

Gly Arg Ile Asp Pro Leu Arg Gly Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

-continued

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro
        435                 440

<210> SEQ ID NO 125
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 125

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Arg Thr Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 126
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 126

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Leu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 127
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 127

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Arg Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 128
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60
```

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Arg Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 129
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Arg Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 130
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 130

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 131
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 131

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Asn Thr Lys Tyr Arg Glu Lys Phe
    50                  55                  60

Glu Gly Arg Val Thr Ile Thr Ala Asp Thr Ser Thr Asn Thr Ala Tyr

```
            65                  70                  75                  80
        Met Glu Leu Ser Ser Leu Arg Ser Glu Asp Thr Ala Val Tyr Tyr Cys
                        85                  90                  95

Val Arg Ser Gly Arg Ser Phe Asp Phe Trp Gly Gln Gly Thr Leu Val
                        100                 105                 110

Thr Val Ser Ser Ala Ser Thr Lys Gly Pro Ser Val Phe Pro Leu Ala
                        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
        145                 150                 155                 160

Ala Leu Thr Ser Gly Val His Thr Phe Pro Ala Val Leu Gln Ser Ser
                        165                 170                 175

Gly Leu Tyr Ser Leu Ser Ser Val Val Thr Val Pro Ser Ser Ser Leu
                        180                 185                 190

Gly Thr Gln Thr Tyr Ile Cys Asn Val Asn His Lys Pro Ser Asn Thr
                        195                 200                 205

Lys Val Asp Lys Lys Val Glu Pro Lys Ser Cys Asp Lys Thr His Thr
                        210                 215                 220

Cys Pro Pro Cys Pro Ala Pro Glu Leu Leu Gly Gly Pro Ser Val Phe
        225                 230                 235                 240

Leu Phe Pro Pro Lys Pro Lys Asp Thr Leu Met Ile Ser Arg Thr Pro
                        245                 250                 255

Glu Val Thr Cys Val Val Val Asp Val Ser His Glu Asp Pro Glu Val
                        260                 265                 270

Lys Phe Asn Trp Tyr Val Asp Gly Val Glu Val His Asn Ala Lys Thr
                        275                 280                 285

Lys Pro Arg Glu Glu Gln Tyr Asn Ser Thr Tyr Arg Val Val Ser Val
                        290                 295                 300

Leu Thr Val Leu His Gln Asp Trp Leu Asn Gly Lys Glu Tyr Lys Cys
        305                 310                 315                 320

Lys Val Ser Asn Lys Ala Leu Pro Ala Pro Ile Glu Lys Thr Ile Ser
                        325                 330                 335

Lys Ala Lys Gly Gln Pro Arg Glu Pro Gln Val Tyr Thr Leu Pro Pro
                        340                 345                 350

Ser Arg Asp Glu Leu Thr Lys Asn Gln Val Ser Leu Thr Cys Leu Val
                        355                 360                 365

Lys Gly Phe Tyr Pro Ser Asp Ile Ala Val Glu Trp Glu Ser Asn Gly
                        370                 375                 380

Gln Pro Glu Asn Asn Tyr Lys Thr Thr Pro Pro Val Leu Asp Ser Asp
        385                 390                 395                 400

Gly Ser Phe Phe Leu Tyr Ser Lys Leu Thr Val Asp Lys Ser Arg Trp
                        405                 410                 415

Gln Gln Gly Asn Val Phe Ser Cys Ser Val Met His Glu Ala Leu His
                        420                 425                 430

Asn His Tyr Thr Gln Lys Ser Leu Ser Leu Ser Pro
                        435                 440

<210> SEQ ID NO 132
<211> LENGTH: 444
<212> TYPE: PRT
<213> ORGANISM: Artificial
<220> FEATURE:
<223> OTHER INFORMATION: An artificially synthesized peptide sequence
```

-continued

```
<400> SEQUENCE: 132

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Asn Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

```
Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 133
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 133

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr Arg Glu Lys Phe
50                  55                  60

Glu Gly Arg Val Thr Ile Thr Ala Asp Thr Ser Asn Thr Ala Tyr
65                  70                  75                  80

Met Glu Leu Ser Ser Leu Arg Ser Glu Asp Thr Ala Val Tyr Tyr Cys
            85                  90                  95

Val Arg Ser Gly Thr Ser Phe Asp Phe Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335
```

```
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440
```

<210> SEQ ID NO 134
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 134

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Ser Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Thr Ser Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

-continued

```
Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 135
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 135

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Gln Trp Val Arg Gln Ala Pro Gly Gln Gly Leu Glu Trp Met
            35                  40                  45

Gly Arg Ile Asp Pro Leu Arg Arg Gln Thr Lys Tyr Arg Glu Lys Phe
        50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 136
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Arg Thr
                85                  90                  95

```
Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 137
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 137

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Glu Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Ser Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 138
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 138

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr His Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Ser Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

-continued

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 139
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 139

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80
```

```
Met Glu Leu Ser Ser Leu Arg Ala Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 140
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 140
```

-continued

```
Gln Asp Gln Leu Val Gln Ser Gly Ala Glu Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
            35                  40                  45

Gly Arg Ile Asp Pro Leu Arg Arg Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 141
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Lys Tyr
            20                  25                  30

Ile Ala Trp Tyr Gln Gln Lys Pro Gly Gln Ala Pro Arg Leu Leu Ile
            35                  40                  45

Gln Tyr Thr Ser Thr Leu Gln Pro Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Glu Gln Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 142
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 142

Gln Asp Gln Leu Val Gln Ser Gly Ala Glu Val Lys Asn Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
            35                  40                  45

Gly Arg Ile Asp Pro Leu Arg Arg Gln Thr Lys Tyr Arg Glu Lys Phe
        50                  55                  60

```
Glu Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 143
<211> LENGTH: 444
<212> TYPE: PRT
<213> ORGANISM: Artificial
<220> FEATURE:
```

-continued

<223> OTHER INFORMATION: An artificially synthesized peptide sequence

<400> SEQUENCE: 143

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr Arg Glu Lys Phe
    50                  55                  60

Glu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro
            435                 440

<210> SEQ ID NO 144
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 144

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr Lys Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
                435                 440

<210> SEQ ID NO 145
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 145

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr His Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 146
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 146

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 147
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 147

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
            35                  40                  45

Gly Arg Ile Asp Pro Leu Arg His Gln Thr Lys Tyr Arg Glu Lys Phe
            50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                 85                  90                  95

Val Arg Ser Gly Arg Glu Phe Asp Phe Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 148
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 148

-continued

```
Gln Asp Gln Leu Val Gln Ser Gly Ala Glu Val Lys Asn Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr Arg Glu Lys Phe
50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
```

```
                     420                 425                 430
Asn His Tyr Thr Gln Lys Ser Leu Ser Leu Ser Pro
        435                 440

<210> SEQ ID NO 149
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 149

Gln Asp Gln Leu Val Gln Ser Gly Ala Glu Val Lys Asn Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Arg Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
```

```
            340                 345                 350
Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 150
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 150

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Gln Trp Val Arg Gln Ala Pro Gly Gln Gly Leu Glu Trp Met
            35                  40                  45

Gly Arg Ile Asp Pro Leu Arg Lys Gln Thr Lys Tyr Arg Glu Lys Phe
        50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
                260                 265                 270
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 151
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 151

Ser Gly Arg Ser Phe Asp Phe
1               5

<210> SEQ ID NO 152
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 152

Ser Gly Arg Glu Phe Asp Phe
1               5

<210> SEQ ID NO 153
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 153

Arg Ile Asp Pro Leu Arg Arg Gln Thr Lys Tyr Arg Glu Lys Phe Glu
1               5                   10                  15

Gly

<210> SEQ ID NO 154
<211> LENGTH: 7
```

```
<212> TYPE: PRT
<213> ORGANISM: Artificial
<220> FEATURE:
<223> OTHER INFORMATION: An artificially synthesized peptide sequence

<400> SEQUENCE: 154

Ser Gly Thr Ser Phe Asp Phe
1               5

<210> SEQ ID NO 155
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 155

Arg Ile Asp Pro Leu Arg Arg Ser Thr Lys Tyr Arg Glu Lys Phe Glu
1               5                   10                  15

Gly

<210> SEQ ID NO 156
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 156

Arg Ile Asp Pro Leu Arg Glu Gln Thr Lys Tyr Arg Glu Lys Phe Glu
1               5                   10                  15

Gly

<210> SEQ ID NO 157
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 157

Arg Ile Asp Pro Leu Arg Arg Gln Thr Lys Tyr His Glu Lys Phe Glu
1               5                   10                  15

Gly

<210> SEQ ID NO 158
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 158

Ser Gly Arg Glu Phe Asp Tyr
1               5

<210> SEQ ID NO 159
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 159

Arg Ile Asp Pro Leu Arg Arg Gln Thr Lys Tyr Lys Glu Lys Phe Glu
```

```
                 1               5                  10                  15

Gly

<210> SEQ ID NO 160
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 160

Arg Ile Asp Pro Leu Arg Lys Gln Thr Lys Tyr Arg Glu Lys Phe Glu
 1               5                  10                  15

Gly

<210> SEQ ID NO 161
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 161

Arg Ile Asp Pro Leu Arg His Gln Thr Lys Tyr Arg Glu Lys Phe Glu
 1               5                  10                  15

Gly

<210> SEQ ID NO 162
<211> LENGTH: 23
<212> TYPE: PRT
<213> ORGANISM: Artificial
<220> FEATURE:
<223> OTHER INFORMATION: An artificially synthesized peptide sequence

<400> SEQUENCE: 162

Arg Ile Gln Met Thr Gln Ser Pro Ser Ser Leu Ser Ala Ser Val Gly
 1               5                  10                  15

Asp Arg Val Thr Ile Thr Cys
             20

<210> SEQ ID NO 163
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 163

Arg Ala Ser Gln Asp Ile His Lys Tyr Ile Ala
 1               5                  10

<210> SEQ ID NO 164
<211> LENGTH: 8
<212> TYPE: PRT
<213> ORGANISM: Artificial
<220> FEATURE:
<223> OTHER INFORMATION: An artificially synthesized peptide sequence

<400> SEQUENCE: 164

Leu Gln Tyr Glu Gln Leu Arg Thr
 1               5

<210> SEQ ID NO 165
<211> LENGTH: 169
```

```
<212> TYPE: PRT
<213> ORGANISM: Macaca mulatta

<400> SEQUENCE: 165

Met Pro Ala Gly Arg Arg Met Glu Met Leu Ser Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
        35                  40                  45

Thr Ala Leu Val Gln Thr Glu Asp Asn Pro Arg Val Ala Gln Val Ser
    50                  55                  60

Ile Thr Lys Cys Asn Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
                85                  90                  95

Gly Tyr Thr Gly Val Arg Cys Glu His Phe Tyr Leu Thr Val His Gln
            100                 105                 110

Pro Leu Ser Lys Glu Tyr Val Ala Leu Thr Val Ile Leu Ile Ile Leu
        115                 120                 125

Phe Leu Ile Ile Val Val Gly Ser Thr Tyr Tyr Phe Cys Arg Trp Tyr
    130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
                165

<210> SEQ ID NO 166
<211> LENGTH: 1210
<212> TYPE: PRT
<213> ORGANISM: Homo sapiens

<400> SEQUENCE: 166

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175
```

-continued

```
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Asn Cys Gln
        195                 200                 205
Lys Leu Thr Lys Ile Ile Cys Ala Gln Gln Cys Ser Gly Arg Cys Arg
        210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
        290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
```

-continued

```
            595                 600                 605
Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                    645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                    725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                    805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                    885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                    965                 970                 975

Arg Tyr Leu Val Ile Gln Gly Asp Glu Arg Met His Leu Pro Ser Pro
                980                 985                 990

Thr Asp Ser Asn Phe Tyr Arg Ala  Leu Met Asp Glu Glu  Asp Met Asp
            995                 1000                1005

Asp Val  Val Asp Ala Asp Glu  Tyr Leu Ile Pro Gln  Gln Gly Phe
    1010                1015                1020
```

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 167
<211> LENGTH: 169
<212> TYPE: PRT
<213> ORGANISM: Homo sapiens

<400> SEQUENCE: 167

Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
                20                  25                  30

Thr Thr Val Ile Pro Ser Cys Ile Pro Gly Glu Ser Ser Asp Asn Cys
            35                  40                  45

Thr Ala Leu Val Gln Thr Glu Asp Asn Pro Arg Val Ala Gln Val Ser
        50                  55                  60

Ile Thr Lys Cys Ser Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
                85                  90                  95

Gly Tyr Thr Gly Val Arg Cys Glu His Phe Phe Leu Thr Val His Gln
            100                 105                 110

Pro Leu Ser Lys Glu Tyr Val Ala Leu Thr Val Ile Leu Ile Ile Leu
        115                 120                 125

Phe Leu Ile Thr Val Val Gly Ser Thr Tyr Tyr Phe Cys Arg Trp Tyr
    130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val

```
<210> SEQ ID NO 168
<211> LENGTH: 19
<212> TYPE: PRT
<213> ORGANISM: Artificial
<220> FEATURE:
<223> OTHER INFORMATION: An artificially synthesized peptide sequence

<400> SEQUENCE: 168

Met Gly Trp Ser Cys Ile Ile Leu Phe Leu Val Ala Thr Ala Thr Gly
1               5                   10                  15

Val His Ser

<210> SEQ ID NO 169
<211> LENGTH: 507
<212> TYPE: DNA
<213> ORGANISM: Homo sapiens

<400> SEQUENCE: 169
atgaccgcgg ggaggaggat ggagatgctc tgtgccggca gggtccctgc gctgctgctc    60
tgcctgggtt tccatcttct acaggcagtc ctcagtacaa ctgtgattcc atcatgtatc   120
ccaggagagt ccagtgataa ctgcacagct ttagttcaga cagaagacaa tccacgtgtg   180
gctcaagtgt caataacaaa gtgtagctct gacatgaatg gctattgttt gcatggacag   240
tgcatctatc tggtggacat gagtcaaaac tactgcaggt gtgaagtggg ttatactggt   300
gtccgatgtg aacacttctt tttaaccgtc caccaacctt taagcaaaga gtatgtggct   360
ttgaccgtga ttcttattat tttgtttctt atcacagtcg tcggttccac atattatttc   420
tgcagatggt acagaaatcg aaaaagtaaa gaaccaaaga aggaatatga gagagttacc   480 tcagggatc cagagttgcc gcaagtc                                         507

<210> SEQ ID NO 170
<211> LENGTH: 46
<212> TYPE: PRT
<213> ORGANISM: Macaca fascicularis

<400> SEQUENCE: 170

Val Ser Ile Thr Lys Cys Asn Ser Asp Met Asn Gly Tyr Cys Leu His
1               5                   10                  15

Gly Gln Cys Ile Tyr Leu Val Asp Met Ser Gln Asn Tyr Cys Arg Cys
            20                  25                  30

Glu Val Gly Tyr Thr Gly Val Arg Cys Glu His Phe Tyr Leu
        35                  40                  45

<210> SEQ ID NO 171
<211> LENGTH: 34
<212> TYPE: PRT
<213> ORGANISM: Homo sapiens

<400> SEQUENCE: 171

Met Val Leu Ser Thr Thr Val Ile Pro Ser Cys Ile Pro Gly Glu Ser
1               5                   10                  15

Ser Asp Asn Cys Thr Ala Leu Val Gln Thr Glu Asp Asn Pro Arg Val
            20                  25                  30

Ala Gln
```

HUMANIZED ANTI-EPIREGULIN ANTIBODY, AND CANCER THERAPEUTIC AGENT COMPRISING SAID ANTIBODY AS ACTIVE INGREDIENT

REFERENCE TO SEQUENCE LISTING SUBMITTED ELECTRONICALLY

The content of the electronically submitted sequence listing (Name 21440690002_sequencelisting.txt; Size: 304 kilobytes; and Date of Creation: Jun. 11, 2014) filed with the application is incorporated herein by reference in its entirety.

TECHNICAL FIELD

The present invention relates to methods for treating cancer, agents for inhibiting cancer cell proliferation, and anticancer agents.

BACKGROUND ART

Cancer is a leading cause of mortality in industrialized countries. Many chemotherapeutic agents have been developed over the past 50 years for the purpose of cancer treatment. Majority of the chemotherapeutic agents can be classified into alkylating agents, antimetabolites, anthracyclines, plant alkaloids, topoisomerase inhibitors, and antitumor agents. All of these pharmaceutical agents affect cell division or DNA synthesis and bring about therapeutic effects through a mechanism that functions in some way.

Effectiveness of a particular chemotherapeutic agent is different among cancers or patients, or is different depending on the time course in individual patients. Cancer cells exposed to chemotherapeutic agents develop resistance to these chemotherapeutic agents, and similarly often develop cross-resistance to a plurality of other anticancer agents. Furthermore, to control the side effects resulting from cell damage by these chemotherapeutic agents on normal cells through the above-mentioned mechanism of these agents, the dosage or usage of the agents is often restricted.

Instead of conventional chemotherapeutic agents, molecularly-targeted drugs which target molecules expressed specifically on cancer cells are being developed recently. With the appearance of these molecularly-targeted drugs, side effects intrinsic to conventional chemotherapeutic agents can be avoided, and cancer treatments that contribute to the QOL of cancer patients are becoming feasible. Such molecularly-targeted drugs include small-molecule pharmaceutical agents as well as high-molecular-weight pharmaceutical agents such as antibodies. Therapeutic antibodies are molecules that are inherently present in the body, and have the advantage of low toxicity on living organisms, as well as the advantage of exhibiting therapeutic effects by specifically damaging target cells by an action mechanism other than the mechanism of small-molecule pharmaceutical agents, such as cytotoxic activity mediated by effector functions. Accordingly, many therapeutic antibodies have been recently placed on the market Therapeutic antibodies targeting Epiregulin, which is highly expressed in colon cancer, lung adenocarcinoma, pancreatic cancer, stomach cancer, and kidney cancer, have been disclosed as antibodies that specifically damage target cells by an action mechanism other than the mechanism of small-molecule pharmaceutical agents, such as cytotoxic activity mediated by such effector functions (Patent Document 1). Specifically, measurement of complement-dependent cytotoxicity (CDC) activity and antibody-dependent cell-mediated cytotoxicity (ADCC) activity of anti-Epiregulin antibodies revealed that anti-Epiregulin antibodies have CDC activity and ADCC activity on Epiregulin-expressing cells. Furthermore, anti-Epiregulin antibodies were found to have proliferation inhibitory effects on cancer cell lines through neutralizing action. Furthermore, from the above-mentioned findings, anti-Epiregulin antibodies were revealed to be effective for diagnosis, prevention, and treatment of various primary and metastatic cancers.

Any novel candidate pharmaceutical agent including anticancer agents such as those described above must pass strict trials to become commercially available. For example, these trials are classified into preclinical trials and clinical trials. Generally, the latter is further categorized into phase I trial, phase II trial, and phase III trial, and is performed on human patients, whereas the former studies are performed using animals. Generally, an objective of preclinical studies is to demonstrate that the drug candidate is potent as well as effective and safe. Specifically, the objectives of these animal studies are to demonstrate that the pharmaceutical agent is not carcinogenic, mutagenic, or teratogenic, as well as to understand the pharmacokinetics of the pharmaceutical agent. Clinical studies on administration of a test pharmaceutical agent to humans are permitted only when the safety and efficacy of the test pharmaceutical agent towards animals are established in preclinical studies.

In many cases, the action of a small-molecule test pharmaceutical agent (for example, a novel anticancer agent derived from anthracycline) in animals may become an indicator for anticipated actions of the pharmaceutical agent when administered to humans. Therefore, generally data obtained from such preclinical studies may be highly predictable of actions that will take place when it is administered to humans. However, such predictability is not obtained in every type of test pharmaceutical agent; and predictability from results of preclinical studies, and the possibility that candidate pharmaceutical agents are approved in clinical studies drop considerably.

Generally, antibodies can function through highly specific recognition of target molecules which are typically proteinaceous. In most cases, test antibody pharmaceutical agents are monoclonal antibodies, and recognize only a single site or a single epitope on a target molecule. Since monoclonal antibodies conventionally have a high target-identifying function, antibodies have become candidates of great interest for development of pharmaceutical agents, but on the other hand, this identifying function makes preclinical studies difficult in some cases. This is because there are species-specific variations in the target molecule sequences bound by these antibodies. For example, a monoclonal antibody that specifically recognizes molecule Y via epitope X in humans and binds to this molecule will be tested for the corresponding epitope X' in a corresponding target molecule (ortholog) Y' in animal species used for preclinical studies, but X' may be different from X present in the corresponding target molecule in humans. Therefore, oftentimes, the monoclonal antibody cannot specifically recognize the ortholog and bind to the molecule. Even among groups of monoclonal antibodies that have reactivity to human and primate antigens, there are many examples of antibodies that only react with human and chimpanzee antigen homologs. For example, such cases have been observed for anti-CD3 monoclonal antibodies. One of the most widely used CD3 complexes-specific monoclonal antibodies that has the most properties determined is OKT-3. OKT-3 reacts with chimpanzee CD3 but does not react with CD3 homologs of other primates such as rhesus monkeys or canine CD3 (Non- Patent Document 2). On the other hand, there are examples of monoclonal antibodies that recognize rhesus antigens but not their human orthologs. An example in this group is FN-18, which is a monoclonal antibody against rhesus monkey-derived CD3 (Non-patent Document 2).

Several strategies have been adopted to counter problems with preclinical animal studies caused by the high specificity of such monoclonal antibodies.

The first known approach is to perform preclinical studies on test antibody pharmaceuticals using a chimpanzee model. Chimpanzees are the closest genetic relative of humans, and since their genome has 99% identity to the human genome, variations of the target molecule specifically bound by the test antibody pharmaceutical in chimpanzees are highly likely to be identical to the variations of this molecule in humans. In fact, Schlereth et al. have discovered that the variations in CD3 are common between humans and chimpanzees (Non-patent Document 3). Therefore, the risk that this molecule will not be recognized by the test antibody pharmaceutical in chimpanzees is considered to be low. However, studies using chimpanzees are very costly, and have ethical problems as well. Furthermore, since chimpanzees are animals in danger of extinction and the number of animals that can be used in experiments is severely limited, such preclinical studies on chimpanzees are excluded from the development of most test antibody pharmaceuticals.

The second approach is the approach of adapting the molecule used in preclinical studies to the animal used in the studies. In this approach, essential safety information is obtained in preclinical studies by constructing a so-called "surrogate" antibody for administration to test animals. Generally, such a surrogate antibody is an antibody that specifically recognizes a test-animal ortholog of the target molecule bound by the non-surrogate antibody (the actual test antibody pharmaceutical for humans), and is an antibody that has been modified to bind to the ortholog. Therefore, in the approach using such a "surrogate" antibody, one must individually develop two different molecules: the clinical test pharmaceutical agent, and a preclinical test pharmaceutical agent to be used in the preclinical studies on animal species, which has target specificity corresponding to the clinical pharmaceutical agent, and of which safety and such must be examined. The great disadvantage of such a surrogate approach is that the surrogate antibody for the preclinical studies is a modified product of the clinical test antibody pharmaceutical. Therefore, data obtained preclinical studies using a surrogate antibody may not often be directly applicable to humans. Therefore, the predictability of clinical stud results based on preclinical study results using these approaches may decrease.

The above-mentioned approach adapts the test pharmaceutical agent so that it is suitable for the animal used in preclinical studies. On the other hand, other known approaches adapt animals used in the preclinical studies to the candidate pharmaceutical agent to be administered to humans.

An example of adapting a test animal to a test antibody pharmaceutical intended for administration to humans is producing a transgenic animal that expresses the human molecule to which the test antibody pharmaceutical specifically binds instead of the non-human molecule intrinsic to the test animal species. In this method, the test antibody pharmaceutical administered in preclinical studies is expected to bind to a human antigen in the transgenic test animal. For example, in a study conducted by Bugelski et al., preclinical safety evaluation was performed on the monoclonal antibody keliximab using human CD4 transgenic mice to predict long-term treatment of rheumatoid arthritis in human patients. Keliximab is a monoclonal antibody that has specificity to CD4 of humans and chimpanzees. Bugelski et al. conclude that the use of a human protein-expressing transgenic mouse provides a useful alternative method to studies conducted in chimpanzees using biological pharmaceuticals that have limited cross-species specificity. However, production of transgenic animals for test purposes is time consuming and costly since it demands a to of work.

PRIOR ART DOCUMENTS

Patent Documents

[Patent Document 1] WO2008/047723

Non-patent Documents

[Non-patent Document 1] J. Med. Primatol. (1986) 15, 441-451
[Non-patent Document 2] J. Med. Primatol. (2001) 40, 141-147
[Non-patent Document 3] Cancer Immunol. Immunother. 2006 May; 55(5): 503-14
[Non-patent Document 4] Hum. Exp. Toxicol. (2000) 19, 230-243

SUMMARY OF THE INVENTION

Problems to be Solved by the Invention

The present invention relates to anti-Epiregulin antibodies showing cross-species reactivity between non-human animals and humans. The present invention further relates to anti-Epiregulin antibodies with suppressed chemical degradation. The present invention also relates to anti-Epiregulin antibodies with reduced isoelectric point. Furthermore, the present invention relates to anti-Epiregulin antibodies with reduced amount of aggregate. In addition, the present invention relates to pharmaceutical compositions or therapeutic agents for cancer comprising the above-mentioned anti-Epiregulin antibodies. The present invention also relates to methods for producing the aforementioned anti-Epiregulin antibodies.

Means for Solving the Problems

The present inventors discovered that the ratio of binding activity to Epiregulin isolated from cynomolgus monkey to binding activity to human Epiregulin increases by substituting an amino acid residue in the variable region sequence of a humanized EP27 antibody, which inhibits growth of cancer cells by exhibiting cytotoxic activity and neutralizing activity against cancer cells that express human Epiregulin, with an arginine residue. More specifically, the present inventors constructed anti-Epiregulin antibodies showing cross-species reactivity between humans and cynomolgus monkeys which are non-human animals. Furthermore, anti-Epiregulin antibodies with suppressed chemical degradation were constructed by appropriately substituting amino acid residues in the variable region sequence of a humanized EP27 antibody. In addition, anti-Epiregulin antibodies with reduced isoelectric point were constructed by appropriately substituting amino acid residues in the variable region sequence of a humanized EP27 antibody. Anti-Epiregulin antibodies with reduced amount of aggregate were constructed by appropriately substituting amino acid residues in the variable region sequence of a humanized EP27 antibody. The present inventors revealed that the anti-Epiregulin antibodies having these properties show growth inhibitory effects through neutralizing activity and cytotoxic activity on cancer cell lines. In addition, from the above-mentioned findings, the present inventors discovered that anti-Epiregulin antibodies are effective for treatment of various primary and metastatic cancers, and thereby completed the present invention.

More specifically, the present invention relates to the following:

[1] an anti-Epiregulin antibody which is an antibody that binds to an epitope bound by an anti-Epiregulin antibody comprising heavy-chain variable region CDRs of SEQ ID NOs: 9, 10, and 11 and light chain variable region CDRs of SEQ ID NO: 12, 13, and 14, wherein the antibody is characterized in having a smaller ratio of the KD value for monkey Epiregulin of SEQ ID NO: 170 (cEREG KD) to the KD value for human Epiregulin of SEQ ID NO: 34 (hEREG KD) (cEREG KD/hEREG KD) than the cEREG KD/hEREG KD ratio of the anti-Epiregulin antibody comprising heavy-chain variable region CDRs of SEQ ID NOs: 9, 10, and 11 and light-chain variable region CDRs of SEQ ID NO: 12, 13, and 14;

[2] the antibody of [1], wherein cEREG KD/hEREG KD is less than 40;

[3] the antibody of [1], wherein cEREG KD/hEREG KD is less than 10;

[4] the antibody of [1], wherein cEREG KD/hEREG KD is less than 6;

[5] the antibody of [1], wherein cEREG KD/hEREG KD is less than 4;

[6] the antibody of any one of [1] to [5], which comprises a heavy-chain variable region comprising a heavy-chain CDR1 of SEQ ID NO: 9, a heavy-chain CDR2 selected from the group consisting of SEQ ID NOs: 161, 160, 159, 157, 156, 155, 153, 108, 107, 106, 105, 104, 103, 102, 101, and 100, and a heavy-chain CDR3 selected from the group consisting of SEQ ID NOs: 158, 154, 152, 151, 112, 111, 110, and 11; and a light-chain variable region comprising a light-chain CDR1 selected from the group consisting of SEQ ID NOs: 163, 68, 67, and 12, a light-chain CDR2 selected from the group consisting of SEQ ID NOs: 71, 69, and 13, and a light-chain CDR3 selected from the group consisting of SEQ ID NOs: 164, 48, 47, and 14;

[7] the antibody of any one of [1] to [5], which comprises a heavy-chain variable region selected from the group consisting of SEQ ID NOs: 150, 149, 148, 147, 146, 145, 144, 143, 142, 140, 139, 138, 137, 135, 134, 133, 132, 131, 127, 126, 125, 124, 123, 122, 121, 120, 119, 118, 117, 116, and 115, and a light-chain variable region selected from the group consisting of SEQ ID NOs: 141, 136, 130, 129, 128, 99, 85, 84, 83, 82, 81, 80, 58, 57, and 29;

[8] an anti-Epiregulin antibody selected from any one below:
(1) an anti-Epiregulin antibody comprising a heavy-chain variable region selected from the group consisting of SEQ ID NOs: 150, 149, 148, 147, 146, 145, 144, 143, 142, 140, 139, 138, 137, 135, 134, 133, 132, 131, 127, 126, 125, 124, 123, 122, 121, 120, 119, 118, 117, 116, 115, 98, 97, 96, 95, 94, 93, 92, 79, 78, 77, 76, 75, 74, 73, 72, 56, 55, 54, 53, 52, 51, 50, 49, and 38;
(2) an anti-Epiregulin antibody comprising a light-chain variable region selected from the group consisting of SEQ ID NOs: 141, 136, 130, 129, 128, 99, 85, 84, 83, 82, 81, 80, 58, 57, and 29; and
(3) an anti-Epiregulin antibody comprising a heavy-chain variable region selected from the group consisting of SEQ ID NOs: 150, 149, 148, 147, 146, 145, 144, 143, 142, 140, 139, 138, 137, 135, 134, 133, 132, 131, 127, 126, 125, 124, 123, 122, 121, 120, 119, 118, 117, 116, 115, 98, 97, 96, 95, 94, 93, 92, 79, 78, 77, 76, 75, 74, 73, 72, 56, 55, 54, 53, 52, 51, 50, 49, and 38, and a light-chain variable region selected from the group consisting of SEQ ID NOs: 141, 136, 130, 129, 128, 99, 85, 84, 83, 82, 81, 80, 58, 57, and 29;

[9] the antibody of any one of [6] to [8], which comprises the heavy-chain constant region of SEQ ID NO: 26;

[10] the antibody of any one of [6] to [9], which comprises the light-chain constant region of SEQ ID NO: 27;

[11] the antibody of any one of [1] to [10], which has a neutralizing activity;

[12] the antibody of any one of [1] to [11], which has cytotoxicity;

[13] the antibody of [12], wherein the cytotoxicity is CDC and/or ADCC;

[14] the antibody of any one of [1] to [12], wherein a growth inhibitor or a cytotoxic substance is linked to the antibody;

[15] the antibody of [14], wherein the antibody is a low-molecular-weight antibody;

[16] the antibody of any one of [12] to [15], wherein the heavy-chain constant region of SEQ ID NO: 26 comprises at least one substitution of amino acid at a position selected from the group consisting of 230, 240, 244, 245, 247, 262, 263, 266, 273, 275, 299, 302, 313, 323, 325, 328, and 332 as indicated by EU numbering;

[17] a vector comprising a polynucleotide encoding a heavy-chain variable region that comprises a heavy-chain CDR1 of SEQ ID NO: 9, a heavy-chain CDR2 selected from the group consisting of SEQ ID NOs: 161, 160, 159, 157, 156, 155, 153, 108, 107, 106, 105, 104, 103, 102, 101, and 100, and a heavy-chain CDR3 selected from the group consisting of SEQ ID NOs: 158, 154, 152, 151, 112, 111, 110, and 11;

[18] the vector of [17], which comprises a polynucleotide encoding the heavy-chain constant region of SEQ ID NO: 26;

[19] a vector comprising a polynucleotide encoding a light-chain variable region that comprises a light-chain CDR1 selected from the group consisting of SEQ ID NOs: 163, 68, 67, and 12, a light-chain CDR2 selected from the group consisting of SEQ ID NOs: 71, 69, and 13, and a light-chain CDR3 selected from the group consisting of SEQ ID NOs: 164, 48, 47, and 14;

[20] the vector of claim [19], which comprises a polynucleotide encoding the light-chain constant region of SEQ ID NO: 27;

[21] a vector comprising:
(1) a polynucleotide encoding a heavy-chain variable region comprising a heavy-chain CDR1 of SEQ ID NO: 9, a heavy-chain CDR2 selected from the group consisting of SEQ ID NOs: 161, 160, 159, 157, 156, 155, 153, 108, 107, 106, 105, 104, 103, 102, 101, and 100, and a heavy-chain CDR3 selected from the group consisting of SEQ ID NOs: 158, 154, 152, 151, 112, 111, 110, and 11; and
(2) a polynucleotide encoding a light-chain variable region comprising a light-chain CDR1 selected from the group consisting of SEQ ID NOs: 163, 68, 67, and 12, a light-chain CDR2 selected from the group consisting of SEQ ID NOs: 71, 69, and 13, and a light-chain CDR3 selected from the group consisting of SEQ ID NOs: 164, 48, 47, and 14;

[22] a vector comprising:
(1) a polynucleotide encoding a heavy-chain variable region comprising a heavy-chain CDR1 of SEQ ID NO: 9, a heavy-chain CDR2 selected from the group consisting of SEQ ID NOs: 161, 160, 159, 157, 156, 155, 153, 108, 107, 106, 105, 104, 103, 102, 101, and 100, and a heavy-chain CDR3 selected from the group consisting of SEQ ID NOs: 158, 154, 152, 151, 112, 111, 110, and 11, and a polynucleotide encoding the heavy-chain constant region of SEQ ID NO: 26; and
(2) a polynucleotide encoding a light-chain variable region comprising a light-chain CDR1 selected from the group consisting of SEQ ID NOs: 163, 68, 67, and 12, a light-chain CDR2 selected from the group consisting of SEQ ID NOs: 71, 69, and 13, and a light-chain CDR3 selected from the group consisting of SEQ ID NOs: 164, 48, 47, and 14, and a polynucleotide encoding the light-chain constant region of SEQ ID NO: 27;

[23] a vector comprising the polynucleotide of [18] or [22], which comprises a mutated nucleotide encoding a heavy-chain constant region with at least one substitution of amino acid at a position selected from the group consisting of 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 as indicated by EU numbering in the heavy-chain constant region of SEQ ID NO: 26;

[24] a host cell comprising the vectors of [17] and [19], the vectors of [18] and [20], or the vector of [21] or [22];

[25] a host cell comprising the vector of [23];

[26] the host cell of [25], wherein the ability to add fucose to a sugar chain in the host cell is low;

[27] the host cell of [26], wherein the host cell with a low ability to add fucose to a sugar chain is a host cell deficient in one or more functional proteins selected from the group consisting of fucosyltransferase, fucose transporter, GMD (GDP-mannose-4,6-dehydratase), Fx(GDP-keto-6-deoxymannose-3,5-epimerase, 4-reductase), and GFPP (GDP-β-L-fucose pyrophosphorylase);

[28] the host cell of [25], wherein the host cell has an ability to form a bisecting N-acetylglucosamine structure on a sugar chain;

[29] the host cell of [28], wherein the host cell having an ability to form a bisecting N-acetylglucosamine structure on a sugar chain is a host cell that has β(1,4)-galactosyltransferase activity and comprises a vector comprising a polynucleotide encoding the functional Golgi localization domain of a Golgi-resident polypeptide;

[30] the host cell of [29], comprising a vector that comprises a polynucleotide encoding a functional Golgi localization domain selected from the group consisting of the localization domain of mannosidase II, the localization domain of β(1,2)-N-acetylglucosaminyltransferase I, the localization domain of β(1,2)-N-acetylglucosaminyltransferase II, the localization domain of mannosidase I, and the localization domain of α1-6 core fucosyltransferase; and a polynucleotide encoding a fusion polypeptide comprising the catalytic domain of β(1,4)-galactosyltransferase;

[31] the host cell of any one of [24] to [30], wherein the host cell is selected from the group consisting of a CHO cell, a BHK cell, an NS0 cell, an SP2/0 cell, a YO myeloma cell, a P3X63 mouse myeloma cell, a PER cell, a PER.C6 cell, an HEK293 cell, and a hybridoma cell;

[32] a method for producing the antibody of any one of [1] to [16], which comprises collecting the host cell of any one of [24] to [31] from a culture solution;

[33] an antibody produced by the method of [32];

[34] the antibody of [33], wherein a growth inhibitory agent or a cytotoxic substance is linked to the antibody;

[35] a pharmaceutical composition comprising the antibody of any one of [1] to [16] or [33] or [34] as an active ingredient;

[36] a therapeutic agent for cancer or an agent for suppressing cancer recurrence or metastasis, which comprises the antibody of any one of [1] to [16] or [33] or [34] as an active ingredient;

[37] the therapeutic agent for cancer or agent for suppressing cancer recurrence or metastasis of [36], wherein the cancer is any cancer selected from the group consisting of colon cancer, lung adenocarcinoma, pancreatic cancer, stomach cancer, and kidney cancer;

[38] the therapeutic agent for cancer or agent for suppressing cancer recurrence or metastasis of [37], wherein the colon cancer is a poorly differentiated colon cancer, a moderately differentiated colon cancer, or a well differentiated colon cancer; and

[39] the therapeutic agent for cancer or agent for suppressing cancer recurrence or metastasis of any one of [36] to [38], wherein a subject administered with the therapeutic agent for cancer is a subject carrying Epiregulin protein-expressing cancer cells detected in an isolated tissue sample.

The present invention also relates to methods for suppressing cell proliferation, methods for preventing or treating cancer, and methods for suppressing cancer recurrence or metastasis, which comprise the step of administering to a subject an antibody of the present invention or an antibody produced by a production method of the present invention. Furthermore, the present invention relates to uses of an antibody of the present invention or an antibody produced by a production method of the present invention in producing agents for inhibiting cell proliferation, agents for preventing or treating cancer, or agents for suppressing cancer recurrence or metastasis. The present invention also relates to antibodies of the present invention or antibodies produced by a production method of the present invention for use in suppressing cell proliferation, preventing or treating cancer, or suppressing cancer recurrence or metastasis. Furthermore, the present invention relates to methods for producing agents for inhibiting cell proliferation, agents for preventing or treating cancer, or agents for suppressing cancer recurrence or metastasis, which comprise the step of using an antibody of the present invention or an antibody produced by a production method of the present invention.

MODE CARRYING OUT THE INVENTION

Figure 1:
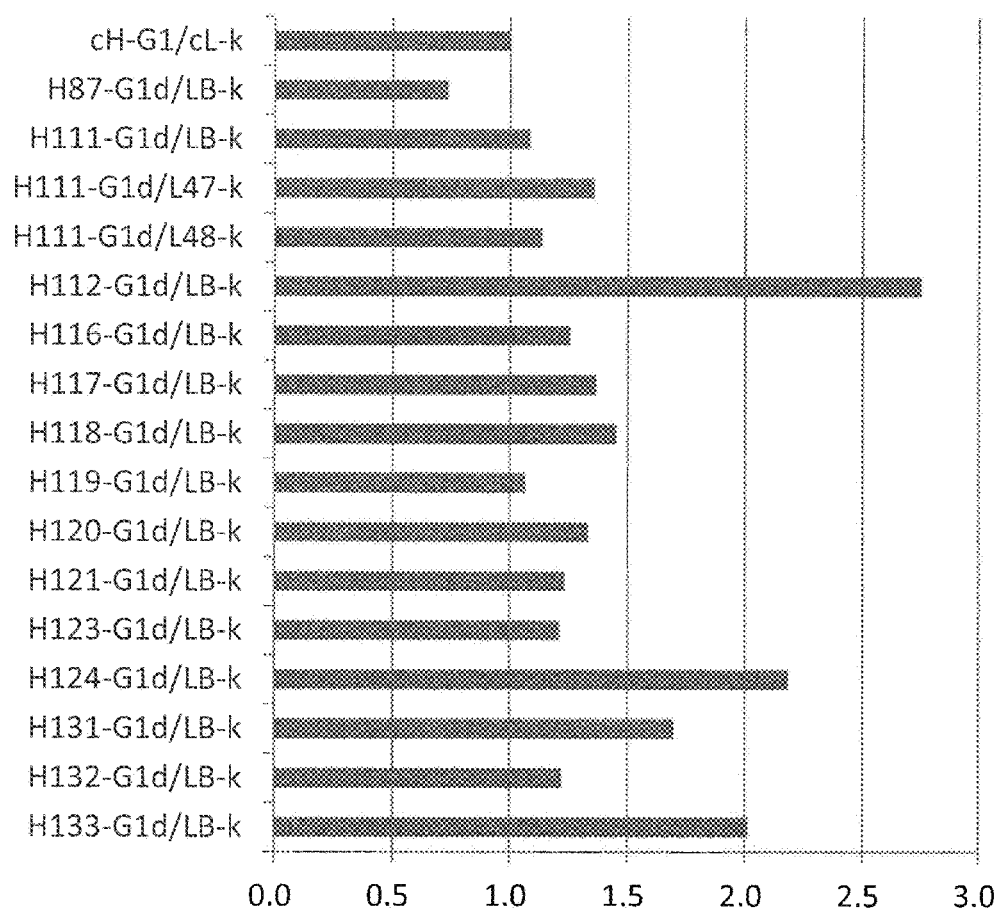
FIG. 1 depicts a graph showing the affinity ratio of each of the antibodies to human Epiregulin (KD value of each antibody/KD value of the chimeric antibody EP27). While notation of the antibody name is described by the name of the variable region only, the figure depicts test results of antibodies containing the G1d heavy-chain and the kappa light-chain constant regions.

The present invention relates to anti-Epiregulin antibodies showing cross-species reactivity between non-human animals and humans. The present invention further relates to anti-Epiregulin antibodies with suppressed chemical degradation. The present invention also relates to anti-Epiregulin antibodies with reduced isoelectric point. Furthermore, the present invention relates to anti-Epiregulin antibodies with reduced amount of aggregate. In addition, the present invention relates to pharmaceutical compositions or therapeutic agents for cancer comprising the above-mentioned anti-Epiregulin antibodies. The present invention also relates to methods for producing the aforementioned anti-Epiregulin antibodies.

The definitions and detailed description below are provided to help the understanding of the present invention illustrated herein.

Definitions

Amino Acids

Herein, amino acids are described in one or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V. Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

Antigens

Antibodies provided by the present invention bind to Epiregulin as an antigen. Epiregulin is a membrane-bound epidermal growth factor protein. Its amino acid sequence is disclosed in GenBank Accession Number NP_001423 (SEQ ID NO: 167). In the present invention, the definition of Epiregulin includes both the full-length protein and fragments thereof. "Fragments" refers to polypeptides comprising any region of Epiregulin, and may not have the function of native Epiregulin. An example of the fragments includes a fragment comprising the extracellular region of Epiregulin. Positions 30 to 118 in the amino acid sequence of SEQ ID NO: 167 correspond to the extracellular region of Epiregulin. Positions 119 to 140 in the amino acid sequence of SEQ ID NO: 167 correspond to the transmembrane region. Herein, Epiregulin may be referred to as EREG, and they are used synonymously.

"Epitope" means an antigenic determinant in an antigen, and refers to an antigen site to which the antigen-binding domain of an anti-Epiregulin antibody disclosed herein binds. Thus, for example, the epitope can be defined according to its structure. Alternatively, the epitope may be defined according to the antigen-binding activity of an anti-Epiregulin antibody that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope whose primary amino acid sequence is recognized such as an epitope consisting of a number of consecutive amino acids in the primary amino acid sequence. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Binding Activity

Examples of a method for confirming the binding of an antibody to Epiregulin, or more specifically an epitope present in the Epiregulin molecule, are shown below; but the method is not limited to the following methods, and one skilled in the art can appropriately use known methods for measuring the antigen binding activity of an antibody.

For example, whether an anti-Epiregulin antibody recognizes a linear epitope in the Epiregulin molecule can be confirmed for example as mentioned below. A linear peptide comprising an amino acid sequence forming the extracellular domain of Epiregulin is synthesized for the above purpose. The peptide can be synthesized chemically, or obtained by genetic engineering techniques using a region encoding the amino acid sequence corresponding to the extracellular domain in a cDNA encoding Epiregulin (examples include CR541887 (SEQ ID No: 169) and such as a cDNA sequence and NM_001432 and such as an mRNA sequence). Then, an anti-Epiregulin antibody is assessed for its binding activity towards a linear peptide comprising the amino acid sequence forming the extracellular domain. For example, an immobilized linear peptide can be used as an antigen by ELISA to evaluate the binding activity of the antibody towards the peptide. Alternatively, the binding activity towards a linear peptide can be assessed based on the level that the linear peptide inhibits the binding of the antibody to Epiregulin-expressing cells. These tests can demonstrate the binding activity of the antibody towards the linear peptide.

Whether an anti-Epiregulin antibody recognizes a conformational epitope can be assessed as follows. Epiregulin-expressing cells are prepared for the above purpose. An anti-Epiregulin antibody can be determined to recognize a conformational epitope when it strongly binds to Epiregulin-expressing cells upon contact, but does not substantially bind to an immobilized linear peptide comprising an amino acid sequence forming the extracellular domain of Epiregulin. Herein, "not substantially bind" means that the binding activity is 80% or less, generally 50% or less, preferably 30% or less, and particularly preferably 15% or less compared to the binding activity towards cells expressing human Epiregulin.

Methods for assaying the binding activity of an anti-Epiregulin antibody towards Epiregulin-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using Epiregulin-expressing cells as antigen.

In the ELISA format, the binding activity of an anti-Epiregulin antibody towards Epiregulin-expressing cells can be assessed quantitatively by comparing the levels of signal generated by enzymatic reaction. Specifically, a test antibody is added to an ELISA plate onto which Epiregulin-expressing cells are immobilized. Then, the test antibody bound to the cells is detected using an enzyme-labeled antibody that recognizes the test antibody. Alternatively, when FACS is used, a dilution series of a test antibody is prepared, and the antibody binding titer for Epiregulin-expressing cells can be determined to compare the binding activity of the test antibody towards Epiregulin-expressing cells.

The binding of a test antibody towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of an anti-Epiregulin antibody towards Epiregulin include, for example, the following method. First, Epiregulin-expressing cells are reacted with a test antibody, and then this is stained with an FITC-labeled secondary antibody that recognizes the test antibody. The test anti-Epiregulin antibody is appropriately diluted with a suitable buffer to prepare the antibody at a desired concentration. For example, the antibody can be used at a concentration within the range of 10 μg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antibody, which is represented by the quantity of the test antibody bound, can be determined by measuring the Geometric Mean value.

Whether an anti-Epiregulin antibody shares a common epitope with another antibody can be assessed based on the competition between the two molecules for the same epitope. The competition between antibodies can be detected by cross-blocking assay or the like. For example, the competitive ELISA assay is a preferred cross-blocking assay.

Specifically, in cross-blocking assay, the Epiregulin protein immobilized to the wells of a microtiter plate is pre-incubated in the presence or absence of a candidate competitor antibody, and then a test antibody is added thereto. The quantity of test antibody bound to the Epiregulin protein in the wells is indirectly correlated with the binding ability of a candidate competitor antibody that competes for the binding to the same epitope. That is, the greater the affinity of the competitor antibody for the same epitope, the lower the binding activity of the test antibody towards the Epiregulin protein-coated wells.

The quantity of the test antibody bound to the wells via the Epiregulin protein can be readily determined by labeling the antibody in advance. For example, a biotin-labeled antibody is measured using an avidin/peroxidase conjugate and appropriate substrate. In particular, cross-blocking assay that uses enzyme labels such as peroxidase is called "competitive ELISA assay". The antibody can also be labeled with other labeling substances that enable detection or measurement. Specifically, radiolabels, fluorescent labels, and such are known.

When the candidate competitor antibody can block the binding by an antibody towards Epiregulin by at least 20%, preferably at least 20 to 50%, and more preferably at least 50% compared to the binding activity in a control experiment conducted in the absence of the competitor antibody, the test antibody is determined to substantially bind to the same epitope bound by the competitor antibody, or compete for the binding to the same epitope.

When the structure of an epitope bound by an anti-Epiregulin antibody has already been identified, whether the test and control antibodies share a common epitope can be assessed by comparing the binding activities of the two antibodies towards a peptide prepared by introducing amino acid mutations into the peptide forming the epitope.

To measure the above binding activities, for example, the binding activities of test and control antibodies towards a linear peptide into which a mutation is introduced are compared in the above ELISA format. Besides the ELISA methods, the binding activity towards the mutant peptide bound to a column can be determined by flowing test and control antibodies in the column, and then quantifying the antibody eluted in the elution solution. Methods for adsorbing a mutant peptide to a column, for example, in the form of a GST fusion peptide, are known.

Alternatively, when the identified epitope is a conformational epitope, whether test and control antibodies share a common epitope can be assessed by the following method. First, Epiregulin-expressing cells and cells expressing Epiregulin with a mutation introduced into the epitope are prepared. The test and control antibodies are added to a cell suspension prepared by suspending these cells in an appropriate buffer such as PBS. Then, the cell suspensions are appropriately washed with a buffer, and an FITC-labeled antibody that recognizes the test and control antibodies is added thereto. The fluorescence intensity and number of cells stained with the labeled antibody are determined using FACSCalibur (BD). The test and control antibodies are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antibodies, which are represented by the quantity of labeled antibody bound, can be determined by measuring the Geometric Mean value.

In the above method, whether an antibody does "not substantially bind to cells expressing mutant Epiregulin" can be assessed, for example, by the following method. First, the test and control antibodies bound to cells expressing mutant Epiregulin are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the antibody, the comparison value (ΔGeo-Mean) can be calculated according to the following formula (Formula 1) to determine the ratio of increase in fluorescence intensity as a result of the binding by the antibody.

[Formula 1]

$$\Delta\text{Geo-Mean} = \text{Geo-Mean (in the presence of the antibody)}/\text{Geo-Mean (in the absence of the antibody)}$$

The Geometric Mean comparison value (ΔGeo-Mean value for the mutant Epiregulin molecule) determined by the above analysis, which reflects the quantity of a test antibody bound to cells expressing mutant Epiregulin, is compared to the ΔGeo-Mean comparison value that reflects the quantity of the test antibody bound to Epiregulin-expressing cells. In this case, the concentrations of the test antibody used to determine the ΔGeo-Mean comparison values for Epiregulin-expressing cells and cells expressing mutant Epiregulin are particularly preferably adjusted to be equal or substantially equal. An antibody that has been confirmed to recognize an epitope in Epiregulin is used as a control antibody.

If the ΔGeo-Mean comparison value of a test antibody for cells expressing mutant Epiregulin is smaller than the ΔGeo-Mean comparison value of the test antibody for Epiregulin-expressing cells by at least 80%, preferably 50%, more preferably 30%, and particularly preferably 15%, then the test antibody "does not substantially bind to cells expressing mutant Epiregulin". The formula for determining the Geo-Mean (Geometric Mean) value is described in the CELL QUEST Software User's Guide (BD biosciences). When the comparison shows that the comparison values are substantially equivalent, the epitope for the test and control anti-Epiregulin antibodies can be determined to be the same.

Antibodies

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing an antibody with desired binding activity are known to those skilled in the art. Below is a non-limiting example that describes a method for producing an antibody that binds to Epiregulin (anti-Epiregulin antibody).

Anti-Epiregulin antibodies can be obtained as polyclonal or monoclonal antibodies using known methods. The anti-Epiregulin antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an Epiregulin protein as a sensitizing antigen. Resulting immune cells are fused with known parental cells by conventional cell fusion methods. Then, hybridomas producing an anti-Epiregulin antibody can be selected by screening for monoclonal cells producing an antibody that binds to an epitope in Epiregulin molecule using conventional screening methods.

Specifically, monoclonal antibodies are prepared as mentioned below. First, the human Epiregulin gene whose nucleotide sequence is disclosed in SEQ ID NO: 169 can be expressed to produce a human Epiregulin protein shown in SEQ ID NO: 167, which will be used as a sensitizing antigen for antibody preparation. That is, a gene sequence encoding human Epiregulin is inserted into a known expression vector, and appropriate host cells are transformed with this vector. The desired human Epiregulin protein is purified from the host cells by known methods. In order to obtain soluble human Epiregulin from culture supernatants, for example, a polypeptide comprising the amino acids at positions 30 to 118 in the human Epiregulin polypeptide sequence of SEQ ID NO: 167 or a protein included in the amino acids at positions 30 to 108 shown as SEQ ID NO: 34. Purified natural human Epiregulin protein can also be used as a sensitizing antigen.

The purified Epiregulin protein can be used as a sensitizing antigen for immunization of mammals. A partial Epiregulin peptide may also be used as a sensitizing antigen. In this case, a partial peptide can be prepared by chemical synthesis based on the amino acid sequence of human Epiregulin, or by inserting a partial human Epiregulin gene into an expression vector for expression. Alternatively, a partial peptide can be produced by degrading a human Epiregulin protein with a protease. The length and region of the partial human Epiregulin peptide are not limited to particular embodiments. A preferred region can be arbitrarily selected from the amino acid sequence at amino acid positions 30 to 118 or positions 30 to 108 in the amino acid sequence of SEQ ID NO: 167. The number of amino acids forming a peptide to be used as a sensitizing antigen is preferably at least five or more, for example, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the Epiregulin protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing Epiregulin to be used as a sensitizing antigen, and immunization methods using Epiregulin are specifically described in WO 2008/047723, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as Epiregulin; and there is no need to purify the antigen for immunization.

In order to prepare a monoclonal antibody of the present invention using DNA immunization, first, a DNA expressing an Epiregulin protein is administered to an animal to be immunized. The Epiregulin-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized Epiregulin can also be produced by the methods described in WO 2003/104453.

After immunizing a mammal as described above, an increase in the titer of an Epiregulin-binding antibody is confirmed in the serum. Then, immune cells are collected from the mammal, and then subjected to cell fusion. In particular, splenocytes are preferably used as immune cells.

A mammalian myeloma cell is used as cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:
P3(P3x63Ag8.653) (J. Immunol. (1979) 123 (4), 1548-1550);
P3x63Ag8U.1 (Current Topics in Microbiology and Immunology (1978)81, 1-7);
NS-1 (C. Eur. J. Immunol. (1976)6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);
S194/5.XX0.BU.1 (J. Exp. Med. (1978) 148 (1), 313-323);
R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) prewarmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an Epiregulin-binding monoclonal antibody can bind to Epiregulin expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, Epiregulin-expressing cells are first prepared. Cells preferably used for screening are mammalian cells in which Epiregulin is forcedly expressed. As control, the activity of an antibody to bind to cell-surface Epiregulin can be selectively detected using non-transformed mammalian cells as host cells. Specifically, hybridomas producing an anti-Epiregulin monoclonal antibody can be isolated by selecting hybridomas that produce an antibody which binds to cells forced to express Epiregulin, but not to host cells.

Alternatively, the activity of an antibody to bind to immobilized Epiregulin-expressing cells can be assessed based on the principle of ELISA. For example, Epiregulin-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J.

Biochem. (1990) 192(3), 767-775). Methods for producing recombinant antibodies are also known as described below.

For example, a cDNA encoding the variable region (V region) of an anti-Epiregulin antibody is prepared from hybridoma cells expressing the anti-Epiregulin antibody. For this purpose, total RNA is first extracted from hybridomas. Methods used for extracting mRNAs from cells include, for example:

the guanidine ultracentrifugation method (Biochemistry (1979) 18(24), 5294-5299), and
the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding $\gamma 1$, $\gamma 2a$, $\gamma 2b$, and $\gamma 3$ heavy chains and $\kappa$ and $\lambda$ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the Epiregulin-binding activity of a reshaped immunoglobulin as an indicator. When the objective is to isolate an antibody against Epiregulin, it is more preferred that the binding of the antibody to Epiregulin is specific. An Epiregulin-binding antibody can be screened, for example, by the following steps:

(1) contacting an Epiregulin-expressing cell with an antibody comprising the V region encoded by a cDNA isolated from a hybridoma;
(2) detecting the binding of the antibody to the Epiregulin-expressing cell; and
(3) selecting an antibody that binds to the Epiregulin-expressing cell.

Methods for detecting the binding of an antibody to Epiregulin-expressing cells are known. Specifically, the binding of an antibody to Epiregulin-expressing cells can be detected by the above-described techniques such as FACS. Immobilized samples of Epiregulin-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-Epiregulin antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-Epiregulin antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame two genes digested with the same combination of restriction enzymes.

To produce a monoclonal antibody that bind to Epiregulin, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described later, a peptide having the amino acid sequence MGWSCIILFLVATATGVHS (SEQ ID NO: 168) are used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-Epiregulin antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994/011523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, human embryonic kidney (HEK) 293, or such;
(2) amphibian cells: Xenopus oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When an anti-Epiregulin antibody described herein is administered to human, an antigen-binding domain derived from a genetically recombinant antibody that has been artificially modified to reduce the heterologous antigenicity against human and such, can be appropriately used as the antigen-binding domain of the antibody. Such genetically recombinant antibodies include, for example, humanized antibodies. These modified antibodies are appropriately produced by known methods.

An antibody variable region used to produce the antigen-binding domain of an anti-Epiregulin antibody described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

EU Numbering and Kabat Numbering

According to the methods used in the present invention, amino acid positions assigned to antibody CDR and FR are specified according to Kabat numbering (Sequences of Proteins of Immunological Interest (National Institute of Health, Bethesda, Md., 1987 and 1991)). Herein, variable region amino acids of an anti-Epiregulin antibody are indicated according to Kabat numbering, while constant region amino acids are indicated according to EU numbering based on Kabat's amino acid positions.

Amino Acid Alteration

Known methods such as site-directed mutagenesis (Kunkel et al., (Proc. Natl. Acad. Sci. USA (1985) 82, 488-492)) and overlap extension PCR can be appropriately employed to modify amino acids in amino acid sequences of antibodies. Furthermore, various known methods can also be used as an alteration method for substituting amino acids with those other than natural amino acids (Annu. Rev. Biophys. Biomol. Struct. (2006) 35, 225-249; Proc. Natl. Acad. Sci. U.S.A. (2003) 100 (11), 6353-6357). For example, one may appropriately use a cell-free translation system (Clover Direct (Protein Express)) containing tRNAs linked with an unnatural amino acid on amber suppressor tRNAs, which are complementary to the UAG codon (amber codon) which is a stop codon.

As used herein, when describing the position of amino acid alteration, the meaning of the term "and/or" includes every combination where "and" and "or" are appropriately combined. Specifically, for example, "the amino acid(s) at position(s) 33, 55, and/or 96 are substituted" includes the following variation of amino acid alterations: amino acid(s) at (a) position 33, (b) position 55, (c) position 96, (d) positions 33 and 55, (e) positions 33 and 96, (f) positions 55 and 96, and (g) positions 33, 55, and 96.

Reduction in Immunogenicity

Preferably, the predicted immunogenicity of the antibody of the present invention in a human host is reduced.

"Low immunogenicity" means that a sufficient time to achieve therapeutic efficacy, an antibody does not induce an antibody response in at least the majority of individuals receiving a sufficient amount of the antibody to reduce the effectiveness of continued administration of the antibody.

The level of immunogenicity in humans can be predicted using the MHC class II binding prediction program Propred www.imtech.res.in/raghava/propred) using a 1% threshold value analysis of all alleles. Other programs which may be used include:

Rankpep bio.dfci.harvard.edu/Tools/rankpep.html); and
Epibase (Algonomics proprietary software: algonomics.com).

In comparison with the starting donor molecule, molecules with reduced immunogenicity contain no or a reduced number of peptides predicted to bind to MHC class II alleles that are highly expressed in the target population (Flower et al., Drug Discov. Today (2004) 9(2), 82-90).

Functional analysis of MHC class II binding can be performed by generating overlapping peptides corresponding to the protein of interest, and testing their ability to evoke T cell activation (T cell proliferation assay) or replacing a known MHC class II-binding peptide, which is a reporter peptide (Hammer J et al., J. Exp. Med. (1994) 180, 2353-2358).

Several methods may be employed to reduce the immunogenicity of anti-Epiregulin antibodies of the present invention. The first method is to humanize the aforementioned antibodies. More specifically, CDRs of an anti-Epiregulin antibody isolated from a non-human animal such as a mouse are grafted into a human antibody. To maintain or enhance binding to Epiregulin, amino acid residue(s) of FR(s) may additionally be substituted so that the CDRs of a humanized anti-Epiregulin antibody will form appropriate antigen-binding sites.

A non-limiting embodiment of CDRs of an anti-Epiregulin antibody isolated from mice of the present invention includes heavy chain CDR1 (HCDR1) of SEQ ID NO: 9, heavy chain CDR2 (HCDR2) of SEQ ID NO: 10, and heavy chain CDR3 (HCDR3) of SEQ ID NO: 11. Furthermore, a non-limiting embodiment of CDRs of an anti-Epiregulin antibody isolated from mice of the present invention includes light chain CDR1 (CDR1) of SEQ ID NO: 12, light chain CDR2 (LCDR2) of SEQ ID NO: 13, and light chain CDR3 (LCDR3) of SEQ ID NO: 14.

A non-limiting embodiment of FRs of a human antibody of the present invention includes heavy chain FR1 (HFR1) of SEQ ID NO: 1, heavy chain FR2 (HFR2) of SEQ ID NO: 2 heavy chain FR3 (HFR3) of SEQ ID NO: 3, and heavy chain FR4 (HFR4) of SEQ ID NO: 4.

Furthermore, a non-limiting embodiment of FRs of a human antibody of the present invention includes light chain FR1 (LFR1) of SEQ ID NO: 5, light chain FR2 (LFR2) of SEQ ID NO: 6, light chain FR3 (LFR3) of SEQ ID NO: 7, and light chain FR4 (LFR4) of SEQ ID NO: 8.

A non-limiting embodiment of the variable region of a humanized anti-Epiregulin antibody of the present invention includes the heavy-chain variable region of SEQ ID NO: 15. Furthermore, a non-limiting embodiment of the variable region of a humanized anti-Epiregulin antibody of the present invention includes the light-chain variable region of SEQ ID NO: 16.

In addition, a non-limiting embodiment of FRs of a human antibody of the present invention includes heavy chain FR1 (HFR1) of SEQ ID NO: 17, and heavy chain FR3 (HFR3) of SEQ ID NO: 18. Furthermore, a non-limiting embodiment of FRs of a human antibody of the present invention includes light chain FR2 (LFR2) of SEQ ID NO: 20, light chain FR3 (LFR3) of SEQ ID NO: 21, and light chain FR3 (LFR3) of SEQ ID NO: 23.

A non-limiting embodiment of the variable region of a humanized anti-Epiregulin antibody of the present invention includes the heavy-chain variable region of SEQ ID NO: 19. Furthermore, a non-limiting embodiment of the variable region of a humanized anti-Epiregulin antibody of the present invention includes the light-chain variable region of SEQ ID NO: 22 or 24.

Furthermore, a non-limiting embodiment of FRs of a humanized antibody of the present invention includes heavy chain FR3 (HFR3) of SEQ ID NO: 35 and heavy chain FR3 (HFR3) of SEQ ID NO: 36. A non-limiting embodiment of the variable region of a humanized anti-Epiregulin antibody of the present invention includes the heavy-chain variable region of SEQ ID NO: 37 or 38.

The second method is a method of designing an altered sequence with reduced immunogenicity by analyzing an altered sequence with amino acid alterations in the amino acid sequence of an anti-Epiregulin antibody using the aforementioned MHC class II binding prediction program. Suitable non-limiting examples of the site(s) of amino acid alteration(s) for reducing the immunogenicity of anti-Epiregulin antibodies of the present invention include the amino acid(s) at position(s) 87 and/or 101, as indicated by Kabat numbering, in the heavy-chain sequence of the anti-Epiregulin antibody of SEQ ID NO: 38. Furthermore, preferred non-limiting examples of the site of amino acid alteration for reducing the immunogenicity of anti-Epiregulin antibodies include the amino acid at position 24, as indicated by Kabat numbering, in the light-chain sequence of the anti-Epiregulin antibody of SEQ ID NO: 29.

A preferred example of a non-limiting embodiment of the aforementioned amino acid substitution(s) includes substituting Ser (S) for the amino acid at position 87 and/or substituting Tyr(Y) or Phe(F) for the amino acid at position 101, as indicated by Kabat numbering, in the heavy-chain sequence of the anti-Epiregulin antibody of SEQ ID NO: 38. Furthermore, a preferred example of a non-limiting embodiment of the aforementioned amino acid substitution includes substituting Arg(R) for the amino acid at position 24, as indicated by Kabat numbering, in the light-chain sequence of the anti-Epiregulin antibody of SEQ ID NO: 29.

The third method is a method of appropriately selecting a constant region of an IgG1 allotype selected from among the G1m3 type (a sequence produced by adding GK to the C terminus of the sequence of SEQ ID NO: 31), G1m17, 1 type (SEQ ID NO: 26), and the G1m17 type (a sequence produced by adding GK to the C terminus of the sequence of SEQ ID NO: 30), when designing an anti-Epiregulin antibody comprising a constant region of an IgG1 antibody. Compatibility between the allotype of the human animal species to which the antibody pharmaceutical is administered, and the allotype of this antibody pharmaceutical is known to affect immune responses in the animal species (Genes and Immunity (2011) 12, 213-221).

A non-limiting embodiment of a heavy chain of a humanized anti-Epiregulin antibody of the present invention with reduced immunogenicity includes heavy chains selected from the group consisting of SEQ ID NOs: 37, 38, 49-56, 72-79, 92-98, 115-127, 131-135, 137-140, and 142-150. Furthermore, a non-limiting embodiment of a light chain of a humanized anti-Epiregulin antibody of the present invention includes light chains selected from the group consisting of SEQ ID NO: 29, 57, 58, 80-85, 99, 128-130, 136, and 141.

A non-limiting embodiment of a humanized anti-Epiregulin antibody of the present invention with reduced immunogenicity includes humanized anti-Epiregulin antibodies comprising heavy chains selected from the group consisting of SEQ ID NOs: 37, 38, 49-56, 72-79, 92-98, 115-127, 131-135, 137-140, and 142-150, and light chains selected from the group consisting of SEQ ID NOs: 29, 57, 58, 80-85, 99, 128-130, 136, and 141.

Suppression of Deamidation, Isomerization, and Hydrolysis

It is preferred that deamidation, isomerization, and hydrolysis are suppressed in the anti-Epiregulin antibodies of the present invention.

It is very important to control the amount of aggregate in a protein pharmaceutical when considering quality control and influences on the drug efficacy and immunogenicity (Curr. Opin. Biotechnol. (2009) 20 (6), 708-714). Generally, aggregate formation is affected by both colloidal stability resulting from the protein solution environment and conformational stability resulting from the protein structure (J. Pharm Sci. (2010) 100 (4), 1306-1315). Conditions effective for colloidal stability can be obtained by screening antibody concentration or pH, type of buffer solution, ionic strength, additive, and such by examining the prescription of an antibody fomulation. On the other hand, conformational stability partly depends on the amino acid sequence, and in the case of antibodies, it is considered important to maintain characteristic structures such as the canonical structure of CDRs, consensus sequences of FR, and the VH/VL interface and such (Jung et al., J. Mol. Biol. (2001) 309 (3), 701-716; Xiang et al., J. Mol. Biol. (1995) 253 (3), 385-390; Ewert et al., Methods. (2004) 34 (2), 184-199; Vargas-Madrazo et al., J. Mol. Recognit. (2003) 16 (3) 113-120; and Morea et al., J. Mol. Biol. (1998) 275, 269-294).

Deamidation reaction refers to reactions that take place non-enzymatically on the asparagine and glutamine side chains, and changes amides on the asparagine and glutamine side chains to carboxylic acids. Isomerization results from formation of an unstable cyclic imide intermediate by deamidation of asparagine or dehydration of aspartic acid, as a result of attack of the carbonyl group present on the side chain of asparagine or aspartic acid by a nitrogen electron pair on a residue positioned on the C terminus. This intermediate is changed mostly to isoaspartic acid by cleavage, and the rest becomes aspartic acid. In the case of glutamine, the deamidation rate is generally one tenth that of asparagine, but the mechanism is essentially the same, and only needs water molecules for the reaction to progress. Since these deamidation and isomerization reactions that take place during storage of proteins such as antibodies become causes of the above-described heterogeneity, they are desirably suppressed to the extent possible. Furthermore, deamidation reactions have been reported to readily take place especially at sites where asparagine and glycine are adjacent to each other (Asn-Gly) (Geiger et al., J. Biol. Chem. (1987) 262, 785-794). Furthermore, cleavage of the peptide chain by hydrolysis reaction has been reported to take place in aspartic acid, and hydrolysis is said to take place readily under acidic conditions particularly in a sequence where proline is present on the C-terminal side (Asp-Pro) (Segalas et al., FEBS Letters (1995) 371, 171-175).

To suppress deamidation, isomerization, and hydrolysis, amino acid alterations and such to remove glutaminyl and asparaginyl residues which are sites that undergo deamidation may be carried out when appropriate. A preferred non-limiting embodiment of a deamidation site whose removal is particularly effective includes sites where deamidation reaction is promoted, or more specifically glycine residue, asparagine residue, or glutamine residue in motifs indicated as the NG and QG sequences. Substitution of any of these amino acid residues (N, Q, or G) can remarkably suppress deamidation reactions (WO 2003/057881, WO 2005/067620, or such). Furthermore, methods for producing antibodies with suppressed deamidation reaction by controlling the method for culturing antibody-producing cells may also be used when appropriate. Anti-Epiregulin antibodies provided by the present invention also include anti-Epiregulin antibodies to which the aforementioned technique of suppressing deamidation reaction has been applied.

Non-limiting examples of sites that undergo deamidation preferably include amino acid(s) at position(s) 31, 52, 54, 56, and/or 101 as indicated by Kabat numbering in the heavy-chain sequence of the anti-Epiregulin antibody of SEQ ID NO: 38. Furthermore, non-limiting examples of sites that undergo deamidation preferably include amino acid(s) at position(s) 28, 92, and/or 93 as indicated by Kabat numbering in the light-chain sequence of the anti-Epiregulin antibody of SEQ ID NO: 29.

A non-limiting embodiment of the aforementioned amino acid substitution(s) preferably includes substitution(s) of Ala (A) for the amino acid at position 31 and/or substitution of Thr (T), Lys (K), Phe (F), Val (V), Arg (R), or Leu (L) for the amino acid at position 55, as indicated by Kabat numbering, in the heavy-chain sequence of the anti-Epiregulin antibody of SEQ ID NO: 38. Furthermore, a non-limiting embodiment of the aforementioned amino acid substitution(s) preferably includes substitution(s) of Glu (E) for the amino acid at position 92 and/or Arg (R) or Gln (Q) for the amino acid at position 93, as indicated by Kabat numbering, in the light-chain sequence of the anti-Epiregulin antibody of SEQ ID NO: 29.

Non-limiting embodiments of a heavy chain of a humanized anti-Epiregulin antibody of the present invention with suppressed deamidation, isomerizaton, and hydrolysis include heavy chains selected from the group consisting of SEQ ID NOs: 49-56, 98 115-127, 131-135, 137-140, and 142-150. Furthermore, non-limiting embodiments of a light chain of a humanized anti-Epiregulin antibody of the present invention with suppressed deamidation, isomerization, and hydrolysis include light chains selected from the group consisting of SEQ ID NOs: 57, 58, 128, and 141.

Non-limiting embodiments of a humanized anti-Epiregulin antibody of the present invention with suppressed deamidation, isomerization, and hydrolysis include humanized anti-Epiregulin antibodies comprising heavy chains selected from the group consisting of SEQ ID NOs: 49-56, 98, 115-127, 131-135, 137-140, and 142-150, and light chains selected from the group consisting of SEQ ID NOs: 57, 58, 128, and 141.

Modulation of Isoelectric Point

Preferably, the isoelectric points of anti-Epiregulin antibodies of the present invention are modulated. Methods of controlling the surface charge of an antibody molecule by altering the amino acid residues exposed on the surface of the antibody molecule are known as one of methods for controlling the plasma half-life of antibodies (WO 2007/114319 and WO 2009/041543). Specifically, reducing the isoelectric point (pI) value of an antibody has been known to be able to prolong the plasma half-life of the antibody. Conversely, elevating an antibody's isoelectric point has been known to shorten its plasma half-life, and improve the tissue migration properties of the antibody (Vaisitti et al., J. Biol. Regal. Homeost. Agents. (2005) 19 (3-4), 105-112; Pardridge et al., J. Pharmacol. Exp. Ther. (1998) 286 (1), 548-554). On the other hand, the anti-tumor effect of an antibody whose isoelectric point has been reduced is known to be enhanced compared to that of the antibody prior to alteration (WO 2009/04106).

The pI of a protein such as an antibody is defined as the pH at which the polypeptide has an effective charge. In this field, typically, protein solubility is known to be lowest when the pH of the solution is equivalent to the isoelectric point (pI) of the protein. Therefore, based on the pI, protein solubility at a given pH, for example, pH 6 can be evaluated. The pI of a protein is also a good indicator for the viscosity of a protein in a liquid preparation. High pI shows high solubility and low viscosity (which is particularly important for a highly concentrated preparation). In a non-limiting embodiment of the present invention, candidate domains having a higher pI than a predetermined threshold are selected. Antibody pI also plays a specific role in drug efficacy and biological distribution of the antibody. For example, when the antibody pI becomes high, localization in cells and/or outside the vessel has been known to increase. The most desirable pI properties for a particular antibody must be determined to achieve the desired objective. In several embodiments, antibodies with a pI value of approximately 5.0, 5.5, 6.0, 6.5, 7.0, 7.5, 8.0, 8.5, 9.0 or higher can be obtained. In another non-limiting embodiment, antibodies with a pI value of approximately 9.0, 8.5, 8.0, 7.5, 7.0, 6.5, 6.0, 5.5, 5.0 or less may be selected. One skilled in the art will understand that a single protein may have a plurality of charged forms. Without being bound to a particular theory, the charge of a protein may be modulated by a number of different action mechanisms; and without limitation, examples of such mechanisms include amino acid substitution(s), cation formation, deamination, carboxy-terminal amino acid heterogeneity, phosphorylation, glycosylation, and such. pI used herein is defined as pI of the major-charge form.

A protein pI can be determined by various methods, and without limitation, a non-limiting embodiment of such methods includes isoelectric focusing, and various computer algorithms (see for example, Bjellqvist et al., Electrophoresis (1993) 14, 1023). In a non-limiting embodiment, pI is determined using a Pharmacia Biotech Multiphor 2 electrophoresis system equipped with a multi-temp III cooling bath recirculation unit and an EPS 3501 XL power supply. Pre-cast Ampholine Gel (Amersham Biosciences, pI range: 2.5 to 10) is loaded together with 5 μg of the protein. The relative pI of an antibody is determined using a broad-range pI marker standard (Amersham, pI range: 3-10, 8 μL). Electrophoresis is performed under conditions of 1,500 V and 50 mA for 105 minutes. Next, the gel is fixed using a Sigma fixing solution (5×) diluted to 1× with purified water. The gel is stained using the Simply Blue Stain (Invitrogen) overnight at room temperature. The gel is then destained using a solution consisting of 25% ethanol, 8% acetic acid and 67% purified water. The isoelectric point is determined based on a standard calibration curve using a Bio-Rad densitometer.

To modulate the isoelectric point of an anti-Epiregulin antibody of the present invention, amino acid alterations and such involving removal of charged amino acids in the amino acid sequence of an anti-Epiregulin antibody, or addition or insertion of charged amino acids to the amino acid sequence of an anti-Epiregulin antibody may be carried out when appropriate. Charged amino acids are known to be present among the amino acids. Generally, lysine (K), arginine (R), and histidine (H) are known as amino acids having a positive charge (positively-charged amino acids). Aspartic acid (D), glutamic acid (E), and such are known as amino acids having a negative charge (negatively-charged amino acids). The other amino acids are known as uncharged amino acids.

The above-mentioned "altered amino acid residue" is preferably an amino acid residue selected appropriately from amino acids in either group (a) or group (b) subjected to addition, insertion, or removal, but are not particularly limited to these amino acids.
(a) glutamic acid (E), aspartic acid (D)
(b) lysine (K), arginine (R), histidine (H)

When the original amino acid residue (before alteration) is already charged, altering it to an uncharged amino acid residue is also a preferred embodiment of the present invention. More specifically, alterations in the present invention include (1) substituting a charged amino acid with an uncharged amino acid, (2) substituting a charged amino acid with an oppositely-charged amino acid as compared to the original amino acid, and (3) substituting an uncharged amino acid with a charged amino acid.

Non-limiting examples of positions where amino acids are altered to modulate the isoelectric point of an anti-Epiregulin antibody of the present invention preferably include amino acid(s) at position(s) 13, 61, 62, 64, 65, 97, and/or 98 as indicated by Kabat numbering in the heavy chain sequence of the anti-Epiregulin antibody of SEQ ID NO: 38. Furthermore, non-limiting examples of positions where amino acids are altered to modulate the isoelectric point of an anti-Epiregulin antibody preferably include amino acid(s) at position(s) 24, 55, 56, and/or 107 as indicated by Kabat numbering in the light chain sequence of the anti-Epiregulin antibody of SEQ ID NO: 29.

A non-limiting embodiment of the aforementioned amino acid substitution(s) preferably includes substitution(s) of Asn (N) or Lys (K) for the amino acid at position 14, substitution of Asp (D) or Glu (E) for the amino acid at position 61, substitution of Ser (S) or Gln (Q) for the amino acid at position 62, substitution of Asp (D) or Glu (E) for the amino acid at position 64, substitution of Asp (D) or Glu (E) for the amino acid at position 65, substitution of Arg (R) for the amino acid at position 97 and/or substitution of Glu (E) for the amino acid at position 98, as indicated by Kabat numbering, in the heavy-chain sequence of the anti-Epiregulin antibody of SEQ ID NO: 38. Furthermore, a non-limiting embodiment of the aforementioned amino acid substitution(s) preferably includes substitution(s) of Gln (Q) or Ser (S) for the amino acid at position 24, substitution of Glu (E) for the amino acid at position 55, substitution of Glu (E) for the amino acid at position 56, and/or substitution of Glu (E) for the amino acid at position 106a, as indicated by Kabat numbering, in the light-chain sequence of the anti-Epiregulin antibody of SEQ ID NO: 29.

A non-limiting embodiment of a heavy chain of an anti-Epiregulin antibody of the present invention with modulated isoelectric point includes heavy chains selected from the group consisting of SEQ ID NOs: 72-79, 98, 115-127, 131-135, 137-140, and 142-150. Furthermore, a non-limiting embodiment of a light chain of a humanized anti-Epiregulin antibody of the present invention with modulated isoelectric point includes light chains selected from the group consisting of SEQ ID NOs: 80-85, and 99.

A non-limiting embodiment of an anti-Epiregulin antibody of the present invention with modulated isoelectric point includes anti-Epiregulin antibodies comprising heavy chains selected from the group consisting of SEQ ID NOs: 72-79, 98, 115-127, 131-135, 137-140, and 142-150 and light chains selected from the group consisting of SEQ ID NOs: 80-85, and 99.

Improvement of Stability

Preferably, the stability of anti-Epiregulin antibodies of the present invention is improved. One or more parameters that describe the stability of an antibody include the thermal melting temperature (Tm) value of a domain. The Tm value of an antibody is an excellent indicator of the antibody's thermal stability, and it may also be an indicator of storage period for the antibody. A lower Tm value indicates aggregate formation/lower stability, whereas a higher Tm value indicates non-formation of aggregates/high stability. Therefore, it is preferred that antibodies with high Tm values are provided. In a non-limiting embodiment of the present invention, antibodies with Tm values higher than the predetermined threshold are selected. In some embodiments, antibodies having a Tm value of at least 50° C., 55° C., 60° C., 65° C., 70° C., 75° C., 80° C., 85° C., 90° C., 95° C., or 100° C. or higher are selected.

The thermal melting temperature (Tm) of an antibody can be measured by various standard methods well known in the art. For example, Vermeer et al. studied the unfolding and denaturation of a monoclonal mouse anti-rat IgG of isotype 2b by differential scanning calorimetry (DSC) and circular dichroism (CD) spectroscopy (Biophys. J. (2000) 78, 394-404; Colloids Surfaces A: Physicochem. Eng. Aspects. (2000) 161, 139-150; J. Colloid Interface Sci. (2000) 225, 394-397; and 2000, Biophys. J. (2000) 79, 2150-2154). As a result, it is considered that the folding and unfolding of the IgG can be characterized by two main transitions which are themselves overlap of various steps. The bimodal distribution observed in both DSC and CD experiments did not depend on the scan rate in the experiments. The two transitions appeared to be independent, and the unfolding was irreversible. The secondary structure as well as the thermodynamic stability of Fab and Fc, which were digested from the IgG, were compared with those of the intact immunoglobulin (Vermeer et al., Biophys. J. (2000) 79, 2150-2154). It was shown that the two peaks observed for intact IgG can be assigned to the Fab fragment and Fc fragment, respectively. Vermeer et al. also showed that, in addition to induction by heat, the structural perturbation of IgG in general could also be triggered by changing the pH (Biophys. J. (2000) 78, 394-404) or by interaction with a hydrophobic environment, for example, adsorption onto Teflon surfaces or interaction with surfactants (Vermeer et al., 1998, Biochim. Biophys. Acta. (1988) 1425, 1-12; Colloids Surfaces A: Physicochem. Eng. Aspects. (2000) 161, 139-150; J. Colloid Interface Sci. 225 (2000) 394-397).

In a non-limiting embodiment of the present invention, the Tm of an antibody is measured using a sample containing isolated antibodies. In one embodiment, the Tm of an antibody is measured using a VP-DSC (MicroCal, LLC) under conditions of a scan rate of 1.0° C./minute and a temperature range of 25° C. to 120° C. A. filtering period of eight seconds may be used along with a five-minute pre-scan thermostat. In a specific example, samples are prepared by dialysis into 25 mM Histidine-HCl using Pierce dialysis cups (3.5 kD). The average antibody concentration is 50 μg/mL as determined by absorption at 280 nm. Melting temperatures are determined following the manufacturer's procedures using the Origin software supplied with the system. Briefly, multiple baselines are loaded with buffer in both the sample and reference cells to establish thermal equilibration. After the baseline is subtracted from the sample thermogram, the data are concentration-normalized and fitted using the deconvolution function. In another embodiment, stability of the antibodies is evaluated using a method described below. One or more metrics may further include metrics characterizing the antibody stability under one or more different conditions selected from the group consisting of different pH values, different temperatures, different shear stresses, and different freeze/thaw cycles.

In a non-limiting embodiment of the present invention, DSC measurements can be performed using the Setaram Micro-DSC III (Setaram, Caluire, France). The samples are placed in the calorimeter in a 1-mL sample cell against a 1-mL reference cell containing an appropriate blank solution. The cells are stabilized for four hours at 25° C. inside the calorimeter before the cells are heated to the final temperature at a selected heating rate. The transition temperature and enthalpy can be determined using the Setaram software (Setaram, Version 1.3).

In a non-limiting embodiment of the present invention, the thermal denaturation/renaturation curve can be obtained using circular dichroism (CD) spectroscopy. Changes in the secondary structure of IgG as a function of temperature and/or, for example, pH, can be studied by CD spectroscopy (Fasman et al., (Circular Dichroism and the Conformational Analysis of Biomolecules. (1996) Plenum Press)). According to de Jongh et al., the advantages of this technique are that the spectroscopic signal is not affected by the presence of the surrounding solution and that well-defined procedures are available to elucidate the secondary structure based on reference spectra of the different structure elements (Biochemistry (1994) 33, 14521-14528). The fractions of the secondary structural elements can be obtained from the CD spectra.

In a non-limiting embodiment of the present invention, measurements can be made on a JASCO spectropolarimeter, model J-715 (JASCO International Co.). A quartz cuvette of 0.1 cm light path length can be used. Temperature regulation can be carried out using a JASCO PTC-348WI (JASCO International) thermocouple. Temperature scans are recorded using the Peltier thermocouple with a resolution of 0.2° C. and a time constant of 16 seconds. Wavelength scans in the far-ultraviolet region (0.2 nm resolution) can be obtained by accumulation of a plurality of scans with a suitable scan rate.

The thermal denaturation/renaturation curve can also be measured by a spectroscopic method. When a protein in a solution denatures in response to heating, the molecules aggregate and the solution scatters light more strongly. Aggregation leads to changes in the optical transparency of the sample, and can be measured by monitoring the change in absorbance of visible or ultraviolet light of a defined wavelength.

In a non-limiting embodiment of the present invention, fluorescence spectroscopy is used to obtain the thermal denaturation/renaturation curve. In one embodiment, intrinsic protein fluorescence, for example, intrinsic tryptophan fluorescence is monitored. In another embodiment, fluorescence probe molecules are monitored. Methods for performing fluorescence spectroscopy experiments are well known to those skilled in the art. See, for example, Bashford et al. (Spectrophotometry and Spectrofluorometry: A Practical Approach (1987) 91-114, IRL Press Ltd.), Bell, J. E. (Spectroscopy in Biocheinistry (1981) Vol. I, 155-194, CRC Press), or Brand et al., (Ann. Rev. Biochem. (1972) 41, 843).

As with biological activities of antibody compositions, various methods can be used for assessing their stability based on the physical and chemical structures of the antibodies. For example, to study denaturation of antibodies, methods such as charge-transfer absorption, fluorescence spectroscopy, NMR, reducing capillary gel electrophoresis (rCGE), and/or high performance size exclusion chromatography (HPSEC), are available (for example, Wang et al. (J. Parenteral Science & Technology 42 (Suppl.), S4-S26)) in addition to the above-mentioned analytical methods.

The reducing capillary gel electrophoresis and high performance size exclusion chromatography are the most common and simplest methods to assess the formation of protein aggregates, protein degradation products, and protein fragments. Accordingly, the stability of the composition comprising an anti-Epiregulin antibody provided by the present invention can also be assessed by these methods.

To modify the stability of anti-Epiregulin antibodies of the present invention, appropriate amino acid alterations in the amino acid sequence of anti-Epiregulin antibodies and such may be carried out.

As a non-limiting embodiment for modifying the stability of an anti-Epiregulin antibody of the present invention, when the anti-Epiregulin antibody is an IgG1 antibody, amidation of the C-terminal amino group due to deletion of the C-terminal amino acid lysine residue and deletion of two C-terminal amino acids glycine and lysine is reported as heterogeneity derived from the heavy chain C-terminal sequence of human IgG antibody (G1, SEQ ID NO: 25) (Anal. Biochem. (2007) 360 (1), 75-83). A preferred method for reducing such heterogeneity includes alteration of deleting two heavy-chain C-terminal amino acids, namely deleting glycine at position 446 and lysine at position 447 as indicated by EU numbering (WO 2009/041613). Since it is desirable that heterogeneity derived from the heavy-chain C-terminal sequence in the anti-Epiregulin antibodies of the present invention is not present, the IgG1 sequence in which the glycine at position 446 and lysine at position 447 as indicated by EU numbering in human IgG1 are deleted (G1d, SEQ ID NO: 26) can be used as the constant region sequence.

A non-limiting embodiment of a heavy chain of an anti-Epiregulin antibody of the present invention with improved stability includes heavy chains selected from the group consisting of SEQ ID NOs: 37, 38, 49-56, 72-79, 92-98, 115-127, 131-135, 137-140, and 142-150. Furthermore, a non-limiting embodiment of a light chain of a humanized anti-Epiregulin antibody of the present invention with improved stability includes light chains selected from the group consisting of SEQ ID NOs: 99, 128-130, 136, and 141.

A non-limiting embodiment of an anti-Epiregulin antibody of the present invention with improved stability includes anti-Epiregulin antibodies comprising heavy chains selected from the group consisting of SEQ ID NOs: 37, 38, 49-56, 72-79, 92-98, 115-127, 131-135, 137-140, and 142-150, and light chains selected from the group consisting of SEQ ID NOs: 99, 128-130, 136, and 141.

Reduction in the Amount of Aggregate

The amount of aggregate of anti-Epiregulin antibodies of the present invention is preferably reduced. Controlling the amount of aggregate in a protein pharmaceutical is very important when considering quality control and influences on the drug efficacy and immunogenicity (Curr. Opin. Biotechnol. (2009) 20 (6), 708-714). Generally, aggregate formation is affected by both colloidal stability resulting from the protein solution environment and conformational stability resulting from the protein structure (J. Pharm Sci. (2010) 100 (4), 1306-1315). Desirable conditions effective for colloidal stability can be achieved by screening antibody concentration, pH, type of buffer solution, ionic strength, additive, and such by examining the prescription of an antibody formulation. On the other hand, conformational stability partly depends on the amino acid sequence, and in the case of antibodies, it is considered important to maintain characteristic structures such as the canonical structure of CDRs, and consensus sequences of FRs, and the VH/VL interface and such (Jung et al., J. Mol. Biol. (2001) 309 (3), 701-716; Xiang et al., J. Mol. Biol. (1995) 253 (3), 385-390; Ewert et al., Methods. (2004) 34 (2), 184-199; Vargas-Madrazo et al., J. Mol. Recognit. (2003) 16 (3) 113-120; Morea et al., J. Mol. Biol. (1998) 275, 269-294; and Vargas-Madrazo et al., J. Mol. Recognit. (2003) 16 (3) 113-120).

Various methods can be used to assess the stability of protein formulations containing antibody formulations, based on the physical and chemical structures of the proteins as well as their biological activities. For example, to study protein denaturation, methods such as charge-transfer absorption, thermal analysis, fluorescence spectroscopy, circular dichroism (CD), NMR, as well as HPSEC, tangential flow filtration (TFF), static light scattering (SLS), Fourier transform infrared spectroscopy (FTIR), urea-induced protein unfolding technology, intrinsic tryptophan fluorescence, differential scanning calorimetry, and 1-anilino-8-naphthalene sulfonate (ANS) protein binding technology are available. For example, a method selected from those described in Wang et al. (J. Parenteral Science & Technology (1988) 42 (Suppl), S4-S26) may be used appropriately.

The rCGE and HPSEC are the most common and simplest methods for assessing the formation of protein aggregates, protein degradation, and protein fragmentation. Accordingly, the stability of the liquid formulations of the present invention may be assessed by these methods.

For example, the stability of the anti-Epiregulin antibodies of the present invention may be evaluated by HPSEC or rCGE, wherein the percent area of the peak represents the non-degraded antibody or non-degraded antibody fragment. In a non-limiting embodiment, approximately 250 µg of the antibody (approximately 25 µL of a liquid formulation containing 10 mg/mL of the aforementioned antibody) is injected to a TosoH Biosep TSK G3000SWXL column (7.8 mm×30 cm) equipped with a TSK S×1 guard column (6.0 mm×4.0 cm). The antibody (including antibody fragments thereof) is eluted isocratically with 0.1 M disodium phosphate containing 0.1 M sodium sulfate and 0.05% sodium azide, at a flow rate of 0.8 to 1.0 mL/min. The eluted protein is detected using UV absorbance at 280 nm. A reference standard is run in the assay as a control, and the results are reported as the percent area of the product monomer peak compared to all other peaks excluding the contained volume peak observed at approximately 12 to 14 minutes. Peaks eluting earlier than the monomer peak are recorded as percent aggregate.

To reduce the amount of aggregate of an anti-Epiregulin antibody of the present invention, the hydrophobic interaction between molecules containing the heavy chain and light chain of the anti-Epiregulin antibody is reduced. Specifically, amino acid alteration(s) that substitutes hydrophilic residue(s) for hydrophobic residue(s) in the amino acid sequence of the heavy chain or light chain of an anti-Epiregulin antibody and such are performed appropriately. In a preferred non-limiting embodiment, amino acid alteration(s) that substitutes hydrophilic residue(s) for hydrophobic residue(s) in the CDRs of an anti-Epiregulin antibody and such are performed appropriately. Amino acids are known to include hydrophilic amino acids and hydrophobic amino acids. Generally, Asp (D), Glu (E), Arg (R), Lys (K), His (H), Gly (G), Ser (S), Thr (T), Cys (C), Asn (N), Gln (Q), and Tyr (Y) are known as the hydrophilic amino acids. Ala (A), Val (V), Leu (L), Ile (I), Met (M), Trp (W), Phe (F), and Pro (P) are known as the hydrophobic amino acids. Preferably, the aforementioned amino acid alteration is appropriately selected from substitution(s) of one or more amino acids selected from among the aforementioned hydrophobic residues with amino acids selected from among the aforementioned hydrophilic resides, but are not particularly limited to specific amino acids.

Non-limiting examples of positions that undergo amino acid alterations for reducing the amount of anti-Epiregulin antibody aggregate of the present invention preferably include amino acid(s) at position(s) 60 and/or 98 as indicated by Kabat numbering in the heavy-chain sequence of the anti-Epiregulin antibody of SEQ ID NO: 38.

A non-limiting embodiment of the aforementioned amino acid substitution preferably includes substituting His (H), Lys (K), Thr (T), Ser (S), or Arg (R) for the amino acid at position 60 and/or substituting Ser (S) or Glu (E) for the amino acid at position 98, as indicated by Kabat numbering, in the heavy-chain sequence of the anti-Epiregulin antibody of SEQ ID NO: 38.

A non-limiting embodiment of a heavy chain of an anti-Epiregulin antibody of the present invention with reduced amount of aggregate includes heavy chains selected from the group consisting of SEQ ID NOs: 92-98, 115-127, 131-135, 137-140, and 142-150.

A non-limiting embodiment of an anti-Epiregulin antibody of the present invention with reduced amount of aggregate includes anti-Epiregulin antibodies comprising heavy chains selected from the group consisting of SEQ ID NOs: 92-98, 115-127, 131-135, 137-140, and 142-150, and light chains selected from the group consisting of SEQ ID NOs: 99, 128-130, 136, and 141.

Conferring Cross-Species Reactivity for Binding to Non-Human Animal Epiregulin and Human Epiregulin The anti-Epiregulin antibodies of the present invention are preferably anti-Epiregulin antibodies showing cross-species reactivity between non-human animals and humans. More specifically, the present invention provides an anti-Epiregulin antibody that binds to an epitope bound by an anti-Epiregulin antibody comprising heavy chain variable region CDRs of SEQ ID NOs: 9, 10, and 11 and light chain variable region CDRs of SEQ ID NO: 12, 13, and 14, wherein the antibody is characterized in that its ratio of the KD value for monkey Epiregulin of SEQ ID NO: 170 (cEREG KD) to the KD value for human Epiregulin of SEQ ID NO: 34 (hEREG KD) (cEREG KD/hEREG KD) is smaller than the cEREG KD/hEREG KD ratio of the anti-Epiregulin antibody comprising heavy chain variable region CDRs of SEQ ID NOs: 9, 10, and 11 and light chain variable region CDRs of SEQ ID NO: 12, 13, and 14.

More specifically, in the present invention, the amino acid sequences of heavy chain variable region CDRs of SEQ ID NOs: 9, 10, and 11 and light chain variable region CDRs of SEQ ID NO: 12, 13, and 14 were altered to modify the binding activity to monkey Epiregulin of the anti-Epiregulin antibody comprising the aforementioned CDRs. Since structural differences between monkey Epiregulin and human Epiregulin had not been elucidated, there had been absolutely no guidance as to which amino acid residues of the anti-Epiregulin antibody should be altered to enhance the binding activity to monkey Epiregulin. In the present invention, multiple antibody sequences with amino acid residue substitution(s) at an arbitrary site(s) in the CDRs were designed. Specifically, anti-Epiregulin antibodies with substitution of an Arg (R) residue for an amino acid in the aforementioned CDR sequences were produced.

The anti-Epiregulin antibodies with substitution of an Arg (R) residue for an amino acid in the CDR sequences surprisingly had an enhanced binding activity to monkey Epiregulin. That is, substituting an Arg (R) residue for an amino acid in the CDR sequences of an anti-Epiregulin antibody was able to confer cross-species reactivity of binding to a non-human animal Epiregulin and a human Epiregulin.

The KD value for monkey Epiregulin of SEQ ID NO: 170 (cEREG KD) can be calculated by the method described in the above-mentioned section on "binding activity". Epiregulin-binding activity of an anti-Epiregulin antibody can be measured by methods known to those skilled in the art, and the measurement conditions can be determined appropriately by those skilled in the art. The Epiregulin-binding activity of an anti-Epiregulin antibody can be assessed as KD (dissociation constant), apparent KD (apparent dissociation constant), kd which is the dissociation rate (dissociation rate constant), apparent kd (apparent dissociation constant), or such. They can be measured by methods known to those skilled in the art, and for example, Biacore (GE healthcare), Scatchard plot, FACS, and such may be used. The ratio of the KD value for monkey Epiregulin (cEREG KD) to the KD value for human Epiregulin (hEREG KD) (cEREG KD/hEREG KD) can be determined by dividing this KD value by the KD value for human Epiregulin of SEQ ID NO: 34.

In the present invention, cEREG KD/hEREG KD is preferably less than 40. Furthermore, in a non-limiting embodiment, cEREG KD/hEREG KD is preferably less than 10. In another non-limiting embodiment, cEREG KD/hEREG KD is preferably less than 6, and in a different non-limiting embodiment, cEREG KD/hEREG KD is preferably less than 4.

Non-limiting examples of position(s) where amino acid(s) is/are altered to confer cross-species reactivity for binding to non-human animal Epiregulin and human Epiregulin provided by the present invention preferably include amino acid(s) at position(s) 33, 51, 54, 55, 56, 57, 58, 59, 60, 62, 65, 96, 97, and/or 98 as indicated by Kabat numbering in the heavy chain variable region of the anti-Epiregulin antibody of SEQ ID NO: 38. Furthermore, non-limiting examples of position(s) where amino acid(s) is/are altered to confer cross-species reactivity for binding to non-human animal Epiregulin and human Epiregulin provided by the present invention preferably include amino acid(s) at position(s) 24, 93, and/or 94 as indicated by Kabat numbering in the light chain sequence of the anti-Epiregulin antibody of SEQ ID NO: 29. A preferred example of the amino acid alteration includes substitution of Arg (R) for one or more of the above-mentioned amino acids.

Examples of a non-limiting embodiment of the heavy chain of an anti-Epiregulin antibody of the present invention conferred with cross-species reactivity include heavy chains selected from the group consisting of SEQ ID NOs: 115-127, 131-135, 137-140, and 142-150. Examples of a non-limiting embodiment of the light chain of a humanized anti-Epiregulin antibody of the present invention conferred with cross-species reactivity include light chains selected from the group consisting of SEQ ID NOs: 128-130, 136, and 141.

Examples of a non-limiting embodiment of an anti-Epiregulin antibody of the present invention conferred with cross reactivity include anti-Epiregulin antibodies comprising heavy chains selected from the group consisting of SEQ ID NOs: 98, 115-127, 131-135, 137-140, and 142-150, and light chains selected from the group consisting of SEQ ID NOs: 29, 128-130, 136, and 141.

Neutralizing Activity

An anti-Epiregulin antibody of the present invention is preferably an antibody that has neutralizing activity. Generally, "neutralizing activity" refers to the activity to inhibit the biological activity of a ligand such as viruses or toxins towards cells. More specifically, "substances having neutralizing activity" refers to substances that bind to the ligand or to a receptor binding to the ligand, and inhibit the binding between the ligand and the receptor. When the ligand binding of a receptor is blocked by neutralizing activity, the receptor-mediated biological activity cannot be exerted. Antibodies that have such neutralizing activity are generally referred to as neutralizing antibodies. The neutralizing activity can be measured by comparing the biological activities in the presence and absence of a test substance of which the neutralizing activity is to be evaluated, in the presence of the ligand of interest.

In the present invention, ligand binding of the EGF receptor, which is considered to be the main receptor of Epiregulin, results in dimerization of the receptor, and activation of the intracellular tyrosine kinase domain of the receptor. The activated tyrosine kinase forms phosphorylated tyrosine-containing peptides by autophosphorylation, and the peptides associate with various signal transduction accessory molecules. They are mainly PLCγ (phospholipase Cγ), Shc, Grb2, and such. Of these accessory molecules, the former two are further phosphorylated by the EGF receptor tyrosine kinase. The main signal transduction pathway from the EGF receptor is the pathway in which phosphorylation is transduced in the order of Shc, Grb2, Sos, Ras, Raf/MAPK kinase/MAP kinase. Furthermore, an alternative pathway which is from PLCγ to PKC is considered to exist.

Since such intracellular signal cascades vary depending on the cell type, suitable molecules can be targeted in the target cell of interest, and the target molecules are not limited to the above-mentioned factors. Commercially available kits for measuring in vivo signal activation can be suitably used (for example, the protein kinase C activity assay system (GE Healthcare Bio-Sciences)).

Furthermore, in vivo signaling activation can be detected using as an index, the transcription-inducing effect on a target gene present downstream of the in vivo signaling cascade. Changes in the transcriptional activity can be detected based on the principle of reporter assay. More specifically, a reporter gene such as green fluorescence protein (GFP) or luciferase is positioned downstream of the transcriptional factor or promoter region of the target gene, and the reporter activity is measured. The change in transcriptional activity can be measured based on the reporter activity.

Furthermore, since the EGF receptor usually functions to promote cell proliferation, in vivo signaling activation can be evaluated by measuring the proliferation activity of target cells. In the present invention, the neutralizing activity of a neutralizing antibody of the present invention is evaluated by assessing the cell proliferation activity. However, the present invention is not limited to this method, and the neutralizing activity can be assessed by suitably applying the aforementioned methods to selected target cells.

Specifically, for example, by measuring the below-mentioned cell proliferation activity, the neutralizing activity of an anti-Epiregulin antibody can be evaluated or measured. For example, a method that measures the incorporation of [$^3$H]-labeled thymidine added to the medium by living cells as an index of DNA replication ability is used. As a more convenient method, a dye exclusion method that measures under a microscope the ability of a cell to release a dye such as trypan blue to the outside of the cell, or the MTT method is used. The latter makes use of the ability of living cells to convert 3-(4,5-dimethylthiazol-2-yl)-2,5-diphenyl tetrazolium bromide (MTT), which is a tetrazolium salt, to a blue formazan product. More specifically, a test antibody is added to the culture solution of a test cell, and after a certain period of time, the MTT solution is added to the culture solution, and this is left to stand for a certain time for MTT to be incorporated into the cell. As a result, MTT which is a yellow compound is converted to a blue compound by the action of succinate dehydrogenase in the mitochondria of the cell. After dissolving this blue product for coloration, absorbance is measured and used as an indicator for the number of viable cells.

Besides MTT, reagents such as MTS, XTT, WST-1, and WST-8 are commercially available (Nacalai Tesque, and such) and can be suitably used. Furthermore, methods that evaluate cell proliferation activity using cellular ATP or impedance of cell culture as an indicator are known. For activity measurements, a binding antibody that has the same isotype as the anti-Epiregulin antibody but does not have the neutralizing activity can be used as a control antibody in the same manner as the anti-Epiregulin antibody, and it can be determined that the activity is present when the anti-Epiregulin antibody has a stronger neutralizing activity than the control antibody.

Cytotoxicity

An antibody used in the present invention is preferably an antibody having cytotoxicity.

In the present invention, the cytotoxicity includes, for example, antibody-dependent cell-mediated cytotoxicity (ADCC) activity and complement-dependent cytotoxicity (CDC) activity. In the present invention, CDC activity refers to complement system-mediated cytotoxic activity. Meanwhile, ADCC activity refers to the activity of damaging a target cell when a specific antibody attaches to its cell surface antigen. An Fcγ receptor-retaining cell (immunocyte or such) binds to the Fc portion of the antibody via the Fcγ receptor and the target cell is damaged. An antibody used in the present invention may be an antibody having CDC activity or ADCC activity, or may be an antibody having both CDC activity and ADCC activity.

Whether or not an anti-Epiregulin antibody has ADCC activity or CDC activity can be determined by known methods (for example, Current protocols in Immunology, Chapter 7. Immunologic studies in humans, Editor, John E, Coligan et al., John Wiley & Sons, Inc., (1993), etc.).

First, specifically, effector cells, complement solution, and target cells are prepared.

(1) Preparation of Effector Cells

Spleen is removed from a CBA/N mouse or the like, and spleen cells are isolated in RPMI1640 medium (Invitrogen). After washing the cells with the same medium containing 10% fetal bovine serum (FBS, HyClone), the concentration of the washed spleen cells may be adjusted to $5\times10^6$ /mL to prepare effector cells.

(2) Preparation of Complement Solution

Baby Rabbit Complement (CEDARLANE) is diluted 10-fold in a culture medium (Invitrogen) containing 10% FBS to prepare a complement solution.

(3) Preparation of Target Cells

Target cells can be radioactively labeled by culturing cells expressing an Epiregulin protein with 0.2 mCi sodium chromate-$^{51}$Cr (GE Healthcare Bio-Sciences) in a DMEM medium containing 10% FBS for one hour at 37° C. For Epiregulin protein-expressing cells, one may use cells transformed with a gene encoding the Epiregulin protein, primary colon cancer cells, metastatic colon cancer cells, lung adenocarcinoma cells, pancreatic cancer cells, stomach cancer cells, kidney cancer cells, colon cancer cells, esophageal cancer cells, or such. After radioactive labeling, cells are washed three times with RPMI1640 medium containing 10% FBS, and the target cells can be prepared by adjusting the cell concentration to $2\times10^5$ cells/mL.

ADCC activity and CDC activity can be measured by the method described below. In the case of ADCC activity measurement, 50 μL of the target cell and 50 μL of an anti-Epiregulin antibody are added to each well of a 96-well U-bottom plate (Becton Dickinson), and this is left to stand on ice for 15 minutes. Then, 100 μL of the effector cell is added to each well of the plate, and the plate is incubated in a carbon dioxide incubator for four hours. The final concentration of the antibody can be adjusted to 0 or 10 μg/mL. After incubation, 100 μL of the supernatant is collected, and the radioactivity is measured with a gamma counter (CO-BRAII AUTO-GAMMA, MODEL D5005, Packard Instrument Company). The measured value is used to calculate cytotoxic activity (%) according to:

[Formula 2]

$$(A-C)/(B-C)\times100.$$

A represents the radioactivity (cpm) in each sample, B represents the radioactivity (cpm) in a sample to which 1% NP-40 (Nacalai Tesque) has been added, and C represents the radioactivity (cpm) of a sample containing the target cells only.

Meanwhile, in the case of CDC activity measurement, 50 μL of the target cell and 50 μL of an anti-Epiregulin antibody are added to each well of a 96-well flat-bottom plate (Becton Dickinson), and this is left to stand on ice for 15 minutes. Then, 100 μL of the complement solution is added to each well, and the plate is incubated in a carbon dioxide incubator for four hours. The final concentration of the antibody is adjusted to 0 or 3 μg/mL. After the incubation, 100 μL of the supernatant is collected, and the radioactivity is measured with a gamma counter. The cytotoxicity can be calculated in the same way as in the ADCC activity determination.

Anti-Epiregulin Antibodies with Enchanced ADCC Activity

Anti-Epiregulin antibodies with enhanced ADCC activity may also be used preferably as anti-Epiregulin antibodies of the present invention. As described above, ADCC activity refers to the activity of damaging a target cell when a specific antibody adheres to its cell surface antigen, and an Fcγ receptor-expressing cell (immune cell or such) binds to the antibody's Fc portion via the Fcγ receptor. Therefore, the anti-Epiregulin antibody-mediated ADCC activity can be enhanced by enhancing the Fcγ receptor-binding activity of Fcγ receptor-expressing cells such as immune cells. As methods for enhancing the Fcγ receptor-binding activity of Fcγ receptor-expressing cells such as immune cells, at least the following three known methods can be used.

(1) Anti-Epiregulin Antibodiwes with Fc Region Amino Acid Alteration(s)

Anti-Epiregulin antibodies with enhanced Fcγ receptor-binding activity can be obtained by altering the Fc region amino acid(s) comprised in the anti-Epiregulin antibodies of the present invention. Examples of preferred Fc regions of IgG immunoglobulins for the alteration include Fc regions of human IgGs (IgG1, IgG2, IgG3, or IgG4, and variants thereof).

Amino acids at any positions may be altered to other amino acids as long as the Fcγ receptor-binding activity of an antibody can be enhanced. When an anti-Epiregulin antibody of the present invention contains the Fc region of human IgG1 as an Fc region, it is preferred to include alterations that result in enhancement of Fcγ receptor-binding compared to the binding activity of the Fc region derived from human IgG1. Amino acid alterations for enhancing Fcγ receptor-binding activity have been reported, for example, in WO 2007/024249, WO 2007/021841, WO 2006/031370, WO 2000/042072, WO 2004/029207, WO 2004/099249, WO 2006/105338, WO 2007/041635, WO 2008/092117, WO 2005/070963, WO 2006/020114, WO 2006/116260, and WO 2006/023403.

Examples of such amino acids that can be altered include at least one or more amino acids selected from the group consisting of those at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 according to EU numbering, Alteration of these amino acids may enhance the Fcγ receptor-binding of an Fc region of an anti-Epiregulin antibody. These amino acid alterations can enhance the Fcγ receptor-binding of the Fc region of an anti-Epiregulin antibody of the present invention. An anti-Epiregulin antibody of the present invention may comprise at least one substitution of amino acid, for example, at a position selected from the group consisting of 230, 240, 244, 245, 247, 262, 263, 266, 273, 275, 299, 302, 313, 323, 325, 328, and 332 as indicated by EU numbering in the heavy chain constant region of SEQ ID NO: 26.

Particularly preferred examples of alterations for use in the present invention include at least one or more amino acid alterations selected form the group consisting of:
the amino acid at position 221 to either Lys or Tyr;
the amino acid at position 222 to any one of Phe, Trp, Glu, and Tyr;
the amino acid at position 223 to any one of Phe, Trp, Glu, and Lys;
the amino acid at position 224 to any one of Phe, Trp, Glu, and Tyr;
the amino acid at position 225 to any one of Glu, Lys, and Trp;
the amino acid at position 227 to any one of Glu, Gly, Lys, and Tyr;
the amino acid at position 228 to any one of Glu, Gly, Lys, and Tyr;
the amino acid at position 230 to any one of Ala, Glu, Gly, and Tyr;
the amino acid at position 231 to any one of Glu, Gly, Lys, Pro, and Tyr;
the amino acid at position 232 to any one of Glu, Gly, Lys, and Tyr;
the amino acid at position 233 to any one of Ala, Asp, Phe, Gly, His, Ile, Lys, Leu, Met, Asn, Gln, Arg, Ser, Thr, Val, Trp, and Tyr;
the amino acid at position 234 to any one of Ala, Asp, Glu, Phe, Gly, His, Ile, Lys, Met, Asn, Pro, Gln, Arg, Ser, Thr, Val, Trp, and Tyr;
the amino acid at position 235 to any one of Ala, Asp, Gln, Gly, His, Ile, Lys, Met, Asn, Pro, Gln, Arg, Ser, Thr, Val, Trp, and Tyr;
the amino acid at position 236 to any one of Ala, Asp, Glu, Phe, His, Ile, Lys, Leu, Met, Asn, Pro, Gln, Arg, Ser, Thr, Val, Trp, and Tyr;
the amino acid at position 237 to any one of Asp, Glu, Phe, His, Ile, Lys, Leu, Met, Asn, Pro, Gln, Arg, Ser, Thr, Val, Trp, and Tyr;
the amino acid at position 238 to any one of Asp, Gln, Phe, Gly, His, Ile, Lys, Leu, Met, Asn, Gln, Arg, Ser, Thr, Val, Trp, and Tyr;
the amino acid at position 239 to any one of Asp, Glu, Phe, Gly, His, Ile, Lys, Leu, Met, Asn, Pro, Gln, Arg, Thr, Val, Trp, and Tyr;
the amino acid at position 240 to any one of Ala, Ile, Met, and Thr;
the amino acid at position 241 to any one of Asp, Gln, Leu, Arg, Trp, and Tyr;
the amino acid at position 243 to any one of Leu, Glu, Leu, Gln, Arg, Trp, and Tyr;
the amino acid at position 244 to His;
the amino acid at position 245 to Ala;
the amino acid at position 246 to any one of Asp, Glu, His, and Tyr;
the amino acid at position 247 to any one of Ala, Phe, Gly, His, Ile, Leu, Met, Thr, Val, and Tyr;
the amino acid at position 249 to any one of Glu, His, Gln, and Tyr;
the amino acid at position 250 to either Glu or Gln;
the amino acid at position 251 to Phe;
the amino acid at position 254 to any one of Phe, Met, and Tyr;
the amino acid at position 255 to any one of Glu, Leu, and Tyr;
the amino acid at position 256 to any one of Ala, Met, and Pro;
the amino acid at position 258 to any one of Asp, Glu, His, Ser, and Tyr;
the amino acid at position 260 to any one of Asp, Glu, His, and Tyr;
the amino acid at position 262 to any one of Ala, Glu, Phe, Ile, and Thr;
the amino acid at position 263 to any one of Ala, Ile, Met, and Thr;

the amino acid at position 264 to any one of Asp, Glu, Phe, Gly, His, Ile, Lys, Leu, Met, Asn, Pro, Gln, Arg, Ser, Thr, Trp, and Tyr;

the amino acid at position 265 to any one of Ala, Leu, Phe, Gly, His, Ile, Lys, Leu, Met, Asn, Pro, Gln, Arg, Ser, Thr, Val, Trp, and Tyr;

the amino acid at position 266 to any one of Ala, Ile, Met, and Thr;

the amino acid at position 267 to any one of Asp, Glu, Phe, His, Ile, Lys, Leu, Met, Asn, Pro, Gln, Arg, Thr, Val, Trp, and Tyr;

the amino acid at position 268 to any one of Asp, Glu, Phe, Gly, Ile, Lys, Leu, Met, Pro, Gln, Arg, Thr, Val, and Trp;

the amino acid at position 269 to any one of Phe, Gly, His, Ile, Lys, Leu, Met, Asn, Pro, Arg, Ser, Thr, Val, Trp, and Tyr;

the amino acid at position 270 to any one of Glu, Phe, Gly, His, Ile, Leu, Met, Pro, Gln, Arg, Ser, Thr, Trp, and Tyr;

the amino acid at position 271 to any one of Ala, Asp, Glu, Phe, Gly, His, Ile, Lys, Leu, Met, Asn, Gln, Arg, Ser, Thr, Val, Trp, and Tyr;

the amino acid at position 272 to any one of Asp, Phe, Gly, His, Ile, Lys, Leu, Met, Pro, Arg, Ser, Thr, Val, Trp, and Tyr;

the amino acid at position 273 to either Phe or Ile;

the amino acid at position 274 to any one of Asp, Glu, Phe, Gly, His, Ile, Leu, Met, Asn, Pro, Arg, Ser, Thr, Val, Trp, and Tyr;

the amino acid at position 275 to either Leu or Trp;

the amino acid at position 276 to any one of Asp, Glu, Phe, Gly, His, Ile, Leu, Met, Pro, Arg, Ser, Thr, Val, Trp, and Tyr;

the amino acid at position 278 to any one of Asp, Glu, Gly, His, Ile, Lys, Leu, Met, Asn, Pro, Gln, Arg, Ser, Thr, Val, and Trp;

the amino acid at position 279 to Ala;

the amino acid at position 280 to any one of Ala, Gly, His, Lys, Leu, Pro, Gln, Trp, and Tyr;

the amino acid at position 281 to any one of Asp, Lys, Pro, and Tyr;

the amino acid at position 282 to any one of Glu, Gly, Lys, Pro, and Tyr;

the amino acid at position 283 to any one of Ala, Gly, His, Ile, Lys, Leu, Met, Pro, Arg, and Tyr;

the amino acid at position 284 to any one of Asp, Glu, Leu, Asn, Thr, and Tyr;

the amino acid at position 285 to any one of Asp, Glu, Lys, Gln, Trp, and Tyr;

the amino acid at position 286 to any one of Glu, Gly, Pro, and Tyr;

the amino acid at position 288 to any one of Asn, Asp, Glu, and Tyr;

the amino acid at position 290 to any one of Asp, Gly, His, Leu, Asn, Ser, Thr, Trp, and Tyr;

the amino acid at position 291 to any one of Asp, Glu, Gly, His, Ile, Gln, and Thr;

the amino acid at position 292 to any one of Ala, Asp, Glu, Pro, Thr, and Tyr;

the amino acid at position 293 to any one of Phe, Gly, His, Ile, Leu, Met, Asn, Pro, Arg, Ser, Thr, Val, Trp, and Tyr;

the amino acid at position 294 to any one of Phe, Gly, His, Ile, Lys, Leu, Met, Asn, Pro, Arg, Ser, Thr, Val, Trp, and Tyr;

the amino acid at position 295 to any one of Asp, Glu, Phe, Gly, His, Ile, Lys, Met, Asn, Pro, Arg, Ser, Thr, Val, Trp, and Tyr;

the amino acid at position 296 to any one of Ala, Asp, Glu, Gly, His, Ile, Lys, Leu, Met, Asn, Gln, Arg, Ser, Thr, and Val;

the amino acid at position 297 to any one of Asp, Glu, Phe, Gly, His, Ile, Lys, Leu, Met, Pro, Gln, Arg, Ser, Thr, Val, Trp, and Tyr;

the amino acid at position 298 to any one of Ala, Asp, Glu, Phe, His, Ile, Lys, Met, Asn, Gln, Arg, Thr, Val, Trp, and Tyr;

the amino acid at position 299 to any one of Ala, Asp, Glu, Phe, Gly, His, Ile, Lys, Leu, Met, Asn, Pro, Gln, Arg, Ser, Val, Trp, and Tyr;

the amino acid at position 300 to any one of Ala, Asp, Glu, Gly, His, Ile, Lys, Leu, Met, Asn, Pro, Gln, Arg, Ser, Thr, Val, and Trp;

the amino acid at position 301 to any one of Asp, Glu, His, and Tyr;

the amino acid at position 302 to Ile;

the amino acid at position 303 to any one of Asp, Gly, and Tyr;

the amino acid at position 304 to any one of Asp, His, Leu, Asn, and Thr;

the amino acid at position 305 to any one of Glu, Ile, Thr, and Tyr;

the amino acid at position 311 to any one of Ala, Asp, Asn, Thr, Val, and Tyr;

the amino acid at position 313 to Phe;

the amino acid at position 315 to Leu;

the amino acid at position 317 to either Glu or Gln;

the amino acid at position 318 to any one of His, Leu, Asn, Pro, Gln, Arg, Thr, Val, and Tyr;

the amino acid at position 320 to any one of Asp, Phe, Gly, His, Ile, Leu, Asn, Pro, Ser, Thr, Val, Trp, and Tyr;

the amino acid at position 322 to any one of Ala, Asp, Phe, Gly, His, Ile, Pro, Ser, Thr, Val, Trp, and Tyr;

the amino acid at position 323 to Ile;

the amino acid at position 324 to any one of Asp, Phe, Gly, His, Ile, Leu, Met, Pro, Arg, Thr, Val, Trp, and Tyr;

the amino acid at position 325 to any one of Ala, Asp, Glu, Phe, Gly, His, Ile, Lys, Leu, Met, Pro, Gln, Arg, Ser, Thr, Trp, and Tyr;

the amino acid at position 326 to any one of Ala, Asp, Glu, Gly, Ile, Leu, Met, Asn, Pro, Gln, Ser, Thr, Val, Trp, and Tyr;

the amino acid at position 327 to any one of Ala, Asp, Glu, Phe, Gly, His, Ile, Lys, Leu, Met, Asn, Pro, Arg, Thr, Trp, and Tyr;

the amino acid at position 328 to any one of Ala, Asp, Glu, Phe, Gly, His, Ile, Lys, Met, Asn, Pro, Gln, Arg, Ser, Thr, Val, Trp, and Tyr;

the amino acid at position 329 to any one of Asp, Glu, Phe, Gly, His, Ile, Lys, Leu, Met, Asn, Gln, Arg, Sec, Thr, Val, Trp, and Tyr;

the amino acid at position 330 to any one of Cys, Glu, Phe, Gly, His, Ile, Lys, Leu, Met, Asn, Pro, Arg, Ser, Thr, Val, Trp, and Tyr;

the amino acid at position 331 to any one of Asp, Phe, His, Ile, Leu, Met, Gln, Arg, Thr, Val, Trp, and Tyr;

the amino acid at position 332 to any one of Ala, Asp, Glu, Phe, Gly, His, Lys, Leu, Met, Asn, Pro, Gln, Arg, Ser, Val, Trp, and Tyr;

the amino acid at position 333 to any one of Ala, Asp, Glu, Phe, Gly, His, Ile, Leu, Met, Pro, Ser, Thr, Val, and Tyr;

the amino acid at position 334 to any one of Ala, Glu, Phe, Ile, Leu, Pro, and Thr;

the amino acid at position 335 to any one of Asp, Phe, Gly, His, Ile, Leu, Met, Asn, Pro, Arg, Ser, Val, Trp, and Tyr;

the amino acid at position 336 to any one of Glu, Lys, and Tyr;
the amino acid at position 337 to any one of Glu, His, and Asn;
the amino acid at position 339 to any one of Asp, Phe, Gly, Ile, Lys, Met, Asn, Gln, Arg, Ser, and Thr;
the amino acid at position 376 to either Ala or Val;
the amino acid at position 377 to either Gly or Lys;
the amino acid at position 378 to Asp;
the amino acid at position 379 to Asn;
the amino acid at position 380 to any one of Ala, Asn, and Ser;
the amino acid at position 382 to either Ala or Ile;
the amino acid at position 385 to Glu;
the amino acid at position 392 to Thr;
the amino acid at position 396 to Leu;
the amino acid at position 421 to Lys;
the amino acid at position 427 to Asn;
the amino acid at position 428 to either Phe or Leu;
the amino acid at position 429 to Met;
the amino acid at position 434 to Trp;
the amino acid at position 436 to Ile; and
the amino acid at position 440 to any one of Gly, His, Ile, Leu, and Tyr,
according to EU numbering in the Fc region of an anti-Epiregulin antibody of the present invention. The number of amino acids that are altered is not particularly limited. An amino acid at one position only may be altered, or amino acids at two or more positions may be altered. Examples of combinations of amino acid alterations at two or more positions include the combinations shown in Tables 1-1 and 1-2.

TABLE 1-1

| AMINO ACID COMBINATION | AMINO ACID COMBINATION |
|---|---|
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |
| F243L/V264I | S239D/N297D/I332E |
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |

TABLE 1-1-continued

| AMINO ACID COMBINATION | AMINO ACID COMBINATION |
|---|---|
| L234E/I332E | S239N/A330L/I332E |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |

TABLE 1-2

| | |
|---|---|
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |
| L328Y/I332E | S239D/A330Y/I332E/V240I |
| N297D/I332E | S239D/A330Y/I332E/V264T |
| N297E/I332E | S239D/A330Y/I332E/V266I |
| N297S/I332E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239D/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |

Herein, the "Fcγ receptor-binding activity of the Fc region of an anti-Epiregulin antibody is enhanced" means that the activity of an anti-Epiregulin antibody Fc region with the above-mentioned amino acid alterations to bind any of the human Fcγ receptors, FcγRI, FcγRIIa, FcγRIIb, FcγRIIIa, and/or FcγRIIIb, is higher than the activity of the anti-Epiregulin antibody Fe region before the amino acid alteration to bind these human Fcγ receptors. For example, based on the above-mentioned analysis method, this means that the binding activity of the anti-Epiregulin antibody after alteration is 105% or more, preferably 110% or more, 115% or more, 120% or more, 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, twice or more, 2.5 times or more, 3 times or more, 3.5 times or more, 4 times or more, 4.5 times or more, 5 times or more, 7.5 times or more, 10 times or more, 20 times or more, 30 times or more, 40 times or more, 50 times or more, 60 times or mote, 70 times or more, 80 times or more, 90 times or more, or 100 times or more compared to the binding activity of the anti-Epiregulin antibody before alteration used as the control.

(2) Anti-Epiregulin Antibodies with Reduced Fucose Content in Sugar Chains Attached to the Fc Region A non-limiting embodiment of anti-Epiregulin antibodies of the present invention preferably includes anti-Epiregulin antibodies that have been modified so that the composition of sugar chains attached to the anti-Epiregulin antibody Fc regions will be high in fucose-deficient sugar chains. Those skilled in the art can appropriately select anti-Epiregulin antibodies with a high proportion of Fc region bound with fucose-deficient sugar chains by following the method for analyzing sugar chain structures described below. The proportion of such Fc region bound with fucose-deficient sugar chains can be selected appropriately from 10% to 100% by those skilled in the art. In a non-limiting embodiment, the proportion can be selected from among 10%, 20%, 30%, 40%, 50%, 60%, 70%, 80%, 90%, 91%, 92%, 93%, 94%, 95%, 96%, 97%, 98%, 99%, and 100%. It is known that when a fucose residue is removed from N-acetyl glucosamine at the reducing end of N-glycoside-linked comlex-type sugar chain attached to the antibody Fc region, the affinity to FcγRIIIa is enhanced (J. Biol. Chem. (2003) 278, 3466-3473). Since IgG1 antibodies containing such Fc regions are known to have an enhanced ADCC activity as described later, these Fc region-containing anti-Epiregulin antibodies are also useful as anti-Epiregulin antibodies to be included in the pharmaceutical compositions of the present invention. A non-limiting embodiment of an antibody in which fucose residue is removed from N-acetyl glucosamine at the reducing end of N-glycoside-linked complex-type sugar chain attached to the antibody Fc region preferably includes a glycosylation-modified antibody (WO 1999/054342).

Another non-limiting embodiment of an antibody in which fucose residue is removed from N-acetyl glucosamine at the reducing end of N-glycoside-linked complex-type sugar chain attached to the antibody Fc region preferably includes antibodies that are deficient in the fucose attached to sugar chains (for example, WO 2000/061739, WO 2002/031140, and WO 2006/067913). Host cells that are low in their ability to add fucose to sugar chains due to modifications of their activity to form the sugar chain structure for polypeptides to be glycosylated are used for producing antibodies deficient in the fucose attached to sugar chains. By expressing a desired antibody gene in the host cells, the antibody which is deficient in fucose in its sugar chains can be collected from the host cell culture. Non-limiting preferred examples of the activity to form a sugar chain structure of a polypeptide include the activity of an enzyme or transporter selected from the group consisting of fucosyltransferase (EC 2.4.1.152), fucose transporter (SLC35C1), GMD (GDP-mannose-4,6-dehydratase) (EC 4.2.1.47), Fx (GDP-keto-6-deoxymannose-3,5-epimerase, 4-reductase) (EC 1.1.1.271), and GFPP (GDP-β-L-fucose pyrophosphorylase (EC 2.7.7.30). The structures of these enzymes and transporters are not necessarily specified as long as their activities are exhibited. Herein, proteins that can exhibit these activities are referred to as functional proteins. A non-limiting embodiment of a method for modifying these activities includes loss of these activities. To produce host cells deficient in these activities, known methods such as methods for destroying the genes of these functional proteins to make them dysfunctional may be employed appropriately (for example, WO 2000/061739, WO 2002/031140, and WO 2006/067913). Host cells deficient in such activities can be produced, for example, by a method that destroys the endogenous genes of these functional proteins in CHO cells, BHK cells, NS0 cells, SP2/0 cells, YO myeloma cells, P3X63 mouse myeloma cells, PER cells, PER.C6 cells, HEK293 cells, hybridoma cells, or such so that they are unable to function.

By collecting antibodies from the culture supernatant of the aforementioned host cells transformed with an expression vector comprising an anti-Epiregulin antibody gene, anti-Epiregulin antibodies in which the fucose residue is removed from N-acetyl glucosamine at the reducing end of N-glycoside-linked complex-type sugar chain attached to the antibody Fc region are collected.

(3) Anti-Epiregulin Antibodies Comprising Fc Regions Attached with Bisecting N-acetyl Glucosamine A non-limiting embodiment of anti-Epiregulin antibodies of the present invention preferably includes anti-Epiregulin antibodies comprising Fc regions attached with bisecting N-acetyl glucosamine. Antibodies having a sugar chain containing a bisecting GlcNAc structure (WO 2002/079255, and such) are known. Host cells having an activity to form a sugar chain containing a bisecting GlcNAc structure are used to produce antibodies to which bisecting GlcNAc structure-containing sugar chains are attached. In a preferred non-limiting embodiment, host cells expressing a gene encoding a functional protein having GnTIII (β-1,4-mannosyl-glycoprotein, 4-β-N-acetylglucosaminyltransferase) (EC2.4.1.144) activity or GalT (β-1,4-galactosyltransferase) (EC 2.4.1.38) activity are produced. In another preferred non-limiting embodiment, host cells that co-express a gene encoding a functional protein having human ManII (manosidase II) (3.2.1.114) activity, a gene encoding a functional protein having GnTI (β-1,2-acetylglucosaminyltransferase I) (EC 2.4.1.94) activity, a gene encoding a functional protein having GnTII (β-1,2-acetylglucosaminyltransferase II) (EC 2.4.1.143) activity, a gene encoding a functional protein having ManI (mannosidase) (EC 3.2.1.113) activity, and α-1,6-fucosyl transferase (EC 2.4.1.68) in addition to the aforementioned functional proteins are produced (WO 2004/065540). The aforementioned host cells having the activity to form a sugar chain containing a bisecting GlcNAc structure can be produced by transfecting an expression vector containing a gene for the aforementioned functional protein into CHO cells, BHK cells, NS0 cells, SP2/0 cells, YO myeloma cells, P3X63 mouse myeloma cells, PER cells, PER.C6 cells, HEK293 cells, hybridoma cells, or such.

Anti-Epiregulin antibodies comprising Fc regions attached with bisecting N-acetyl glucosamine are harvested by collecting antibodies from the culture supernatant of the aforementioned host cells transfected with an expression vector containing an anti-Epiregulin antibody gene. Known methods can be used to analyze the sugar chain structure attached to the antibodies. In a non-limiting embodiment, allowing N-Glycosidase F (Roche diagnostics) to act on an anti-Epiregulin antibody of the present invention causes the sugar chain attached to the anti-Epiregulin antibody to dissociate from the protein (J. Pharm. Sci. (1994) 83(12), 1670-1675). After protein removal using ethanol (J. Clin. Invest. (2001), 108(11), 1687-95), the free sugar chain is concentrated and dried, and then fluorescence labeling is carried out using 2-aminopyridine or 2-aminobenzamide (Anal. Biochem. (1995) 230 (2), 229-238). The obtained 2-AP-labeled sugar chain or 2-AB-labeled sugar chain is freed of reagents by solid phase extraction using a cellulose cartridge and then concentrated by centrifugation, and the obtained material is subjected to subsequent analyses as a purified 2-AB-labeled sugar chain. Next, by allowing β-Galactosidase (Seilkagaku Corporation) to act on the purified 2-AB-labeled sugar chain, agalactosyl 2-AB-labeled sugar chain is prepared. The agalactosyl 2-AB-labeled sugar chains prepared using the sugar chains dissociated from anti-Epiregulin antibodies of the present invention as starting materials are analyzed by normal phase HPLC using an amide column TSKgel Amide-80 (Tosoh), and their chromatograms are compared.

Furthermore, the strength of interaction between an antibody Fc region and FcgR has been reported to depend on $Zn^{2+}$ concentration (Immunology Letters 143 (2012) 60-69). The antibody shows a stronger interaction between the Fc region and FcgR when the $Zn^{2+}$ ion concentration of the Fc region is higher. Chelation of $Zn^{2+}$ by His310 and His435 present in CH3 of the antibody Fc region opens up each CH2 domain of the Fc region at a distal position. This facilitates interaction between the CH2 domain and FcgR, and the interaction between the Fc region and FcgR is enhanced. A non-limiting embodiment of an antibody of the present invention includes an antibody in which His at position 310, His at position 435, His at position 433, and/or Asn at position 434 (EU numbering) is chelated with $Zn^{2+}$.

Antibody-Drug Conjugate

A non-limiting embodiment of anti-Epiregulin antibodies of the present invention preferably includes anti-Epiregulin antibody-drug conjugates produced by linking an anti-Epiregulin antibody to a drug having cytotoxicity. Hereinafter, an antibody-drug conjugate may be referred to as ADC. More specifically, the anti-Epiregulin antibody-drug conjugates used in the present invention may be linked appropriately with growth inhibitors or cytotoxic substances such as toxic peptides or radioactive chemical substances. "Radioactive chemical substances" in the present invention refers to substances containing a radioisotope. The radioisotope is not particularly limited and while any radioisotope may be used, for example, $^{32}P$, $^{14}C$, $^{125}I$, $^{3}H$, $^{131}I$, $^{186}Re$, $^{188}Re$, and such may be used. Such anti-Epiregulin antibody-drug conjugates can be obtained by chemically modifying the obtained anti-Epiregulin antibodies. More specifically, to enable a growth inhibitor or a cytotoxic substance to chemically conjugate (for example, covalently bond) with an anti-Epiregulin antibody, a linker molecule is used to link a growth inhibitor or a cytotoxic substance to an antibody via chemical bonds (such as those described above).

Preferably, the linking agent (linker) is a cleavable linker. More preferably, the linker is cleaved under mild conditions (i.e., conditions within a cell under which the activity of the drug is not affected). Examples of suitable cleavable linkers include disulfide linkers, acid-labile linkers, photolabile linkers, peptidase labile linkers, and esterase labile linkers. Disulfide containing linkers are linkers that can be cleaved through disulfide exchange, which can occur under physiological conditions. Acid-labile linkers are linkers cleavable at acidic pH. For example, certain intracellular compartments such as endosomes and lysosomes have an acidic pH (pH 4-5), and provide conditions suitable for cleaving acid-labile linkers. Photolabile linkers are useful at the body surface and in many body cavities that are exposable to light. Furthermore, infrared light can penetrate tissues. Peptidase-labile linkers can be used to cleave certain peptides inside or outside cells (see for example, Trouet et al., Proc. Natl. Acad. Sci. USA (1982) 79, 626-629; and Umemoto et al., Int. J. Cancer (1989) 43, 677-684).

In addition to the aforementioned chemical modifications, such ADCs can be obtained in the form of bispecific antibody molecules designed using genetic engineering techniques so that the antibody can recognize growth inhibitors, or cytotoxic substances such as toxic peptides, or radioactive chemical substances. The "anti-Epiregulin antibodies" of the present invention also includes such antibodies.

Examples of a non-limiting embodiment of the anti-Epiregulin antibody-drug conjugates provided by the present invention include anti-Epiregulin antibodies which have been modified using a toxic peptide such as ricin, abrin, ribonuclease, onconase, DNase I, Staphylococcus enterotoxin A, Pokeweed anti-viral protein, gelonin, diphtheria toxin, Pseudomonas exotoxin, Pseudomonas endotoxin, L-asparaginase, or PEG L-Asparaginase. In another embodiment, one, two or more of a growth inhibitor and a cytotoxic substance such as a toxic peptide may be combined and used to modify the anti-Epiregulin antibody. As described above, the anti-Epiregulin antibody may be linked with the above-mentioned growth inhibitor or a cytotoxic substance such as a toxic peptide or a radioactive chemical substance through a covalent bond or a non-covalent bond. Methods for producing ADCs linked with such a growth inhibitor or a cytotoxic substance such as a toxic peptide or a radioactive substance are known in the art. Examples of the linking groups when an anti-Epiregulin antibody and a growth inhibitor or a cytotoxic substance such as toxic peptide or radioactive substance are directly linked together include a disulfide bond using the SH groups. Specifically, the intramolecular disulfide bond in the Fc region of the anti-Epiregulin antibody is reduced with a reducing agent such as dithiothreitol, and the disulfide bond within the growth inhibitor molecule or the cytotoxic substance is likewise reduced so that the two are linked by the disulfide bond. Prior to linking, either the antibody or either one of the growth inhibitor or the cytotoxic substance may be activated by an activation promoting agent such as Ellman's reagent so that the formation of the disulfide bond between the two molecules is promoted. Preferred non-limiting examples of other methods for directly linking the anti-Epiregulin antibody and the growth inhibitor or the cytotoxic substance such as toxic peptide or radioactive substance include a method using a Schiff base, carbodiimide method, active ester method (N-hydroxysuccinimide method), method using a mixed anhydride, and method using a diazo reaction.

The following can be exemplified as the toxic peptide used in the present invention:

Diphtheria toxin A Chain (Langone et al. (Methods in Enzymology (1993) 93, 307-308))

Pseudomonas Exotoxin (Pai et al. (Nat. Med. (1996) 2 (3), 350-353))

Ricin Chain (Ricin A Chain) (Fulton et al. (J. Biol. Chem. (1986) 261, 5314-5319); Sivam et al. (Cancer Res. (1987) 47, 3169-3173); Cumber et al. (J. Immunol. Methods (1990) 135, 15-24); Wawrzynczak et al. (Cancer Res. (1990) 50, 7519-7562); Gheeite et al. (J. Immunol. Methods (1991) 142, 223-230))

Deglicosylated Ricin A Chain (Thorpe et al. (Cancer Res. (1987) 47, 5924-5931))

Abrin A Chain (Wawrzynczak et al. (Br. J. Cancer (1992) 66, 361-366); Wawrzynczak et al. (Cancer Res (1990)

50, 7319-7562); Sivam et al. (Cancer Res. (1987) 47, 3169-3173); Thorpe et al. (Cancer Res. (1987) 47, 5924-5931))

Gelonin (Sivam et al. (Cancer Res. (1987) 47, 3169-3173); Cumber et al. (J. Immunol. Methods (1990) 135, 15-24); Wawrzynczak et al. (Cancer Res. (1990) 50, 7519-7562); Bolognesi et al. (Clin. Exp. Immunol. (1992) 89, 341-346))

PAP-s or Pokeweed anti-viral protein from seeds (Bolognesi et al. (Clin. Exp. Immunol. (1992), 89, 341-346))

Briodin (Bolognesi et al. (Clin. Exp. Immunol. (1992) 89, 341-346))

Saporin (Bolognesi et al. (Clin. Exp. Immunol. (1992), 89, 341-346))

Momordin (Cumber et al. (J. Immunol. Methods (1990) 135, 15-24); Wawrzynczak et al. (Cancer Res. (1990) 50, 7519-7562); Bolognesi et al. (Clin. Exp. Immunol. (1992) 89, 341-346))

Momorcochin (Bolognesi et al. (Clin. Exp. Immunol. (1992) 89, 341-346))

Dianthin 32 (Bolognesi et al. (Clin. Exp. Immunol. (1992) 89, 341-346))

Dianthin 30 (Stirpe et al. (FEBS Let. (1986) 195, 1-8))

Modeccin (Stirpe et al. (FEBS Let. (1986) 195, 1-8))

Viscumin (Stirpe et al. (FEBS Let. (1986) 195, 1-8))

Volkesin (Stirpe et al. (FEBS Let. (1986) 195, 1-8))

Dodecandrin (Stirpe et al. (FEBS Let. (1986) 195, 1-8))

Tritin (Stirpe et al. (FEBS Let. (1986) 195, 1-8))

Luffin (Stirpe et al. (FEBS Let. (1986) 195, 1-8))

Trichokirin (Casellas et al. (Eur. J. Biochem. (1988) 176, 581-588); Bollognesi et al. (Clin. Exp. Immunol. (1992) 89, 341-346))

Proteinaceous or peptidic pharmaceutical agents or toxins can also be linked to the anti-Epiregulin antibody by genetic engineering techniques. Specifically, a DNA encoding the above-mentioned toxic peptide and a DNA encoding the anti-Epiregulin antibody of the present invention may be fused in frame to produce a recombinant DNA, and then inserted into an expression vector to construct a recombinant vector. This vector is then introduced into suitable host cells to generate transformed cells, which are cultured to express the inserted DNA in the cells. An anti-Epiregulin antibody-drug conjugate to which the toxic peptide is linked can be obtained by isolation and purification from the culture solution. When obtaining fusion proteins of the antibody, typically the respective DNAs are linked so that the proteinaceous drugs or toxins are positioned at the C terminus of the antibody, but are not limited thereto. It is also possible to interposition a peptide linker between the antibody and the proteinaceous pharmaceutical agent or toxin.

Growth Inhibitors

In a non-limiting embodiment, growth inhibitors may preferably include DNA damaging agents, antimitotic agents, and/or antimetabolites. DNA damaging agents may be alkylating agents, topoisomerase inhibitors and/or DNA intercalators. Preferred non-limiting examples of the growth inhibitors may include carboplatin (DNA alkylating agent), etoposide (inhibitor of topoisomerase II), doxorubicin (DNA intercalator), docetaxel (antimitotic agent), and Gemzar (gemcitabine, antimetabolite).

At least one below may be selected as the alkylating agent. That is, at least one alkylating agent selected from among chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119 (becatecarin), dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, and procarbazin can be used as the alkylating agent.

At least one below may be selected as the topoisomerase inhibitor. That is, at least one topoisomerase inhibitor selected from among doxorubicin (Doxil), daunorubicin, epirubicin, idarubicin, anthracenedione (Novantrone), mitoxantrone, mitomycin C, bleomycin, dactinomycin, plicatomycin, ilinotecan (Camptosar), camptothecin, rubitecan, belotecan, etoposide, teniposide, and topotecan (Hycamptin) can be used as the topoisomerase inhibitor.

At least one DNA intercalator selected from proflavine, doxorubicin (adriamycin), daunorubicin, dactinomycin, and thalidomide may be used as the DNA intercalator.

At least one below may be selected as the antimitotic agent. At least one antimitotic agent selected from among paclitaxel (Abraxane)/Taxol, docetaxel (Taxotere), BMS-275183, Xyotax, Tocosal, vinorlebine, vincristine, vinblastine, vindesine, vinzolidine, etoposide (VP-16), teniposide (VM-26), ixabepilone, larotaxel, ortataxel, tesetaxel, and ispinesib can be used as the antimitotic agent.

At least one below may be selected as the antimetabolite. At least one antimetabolite selected from among fluorouracil (5-FU), floxuridine (5-FUdR), methotrexate, Xeloda, Arranon, leucovorin, hydroxyurea, thioguanine (6-TG), mercaptopurine (6-MP), cytarabine, pentostatin, fludarabine phosphate, cladribine (2-CDA), asparaginase, gemcitabine, pemetrexed, bortezomib, aminopterin, raltitrexed, clofarabine, enocitabine, sapacitabine, azacitidine, and such can be used as the antimetabolite.

When an anti-Epiregulin antibody-drug conjugate is incorporated into a cell, the conjugate-linked growth inhibitor or cytotoxic substance such as a toxic peptide can induce cell death of the cell that incorporated this antibody. Therefore, the antibody to which the growth inhibitor or the cytotoxic substance such as a toxic peptide is linked preferably also has internalization activity. In the present invention, "antibody having internalization activity" refers to an antibody that is transported into a cell (into the cytoplasm, vesicles, other organelles, and such) upon binding to Epiregulin on the cell surface. Whether or not an antibody has internalization activity can be confirmed using methods known to those skilled in the art. For example, the internalization activity can be confirmed by the method of contacting an anti-Epiregulin antibody linked to a labeled substance with Epiregulin-expressing cells and determining whether the labeled substance is incorporated into the cells, or the method of contacting an anti-Epiregulin antibody linked to a growth inhibitor or a cytotoxic substance such as a toxic peptide with Epiregulin-expressing cells and determining whether cell death is induced in the Epiregulin-expressing cells. More specifically, whether or not an antibody has internalization activity can be confirmed, for example, by the method described in the later-described Examples.

After an antibody having cytotoxicity such as ADCC binds to a target antigen expressed on the cell surface, the antibody stays at the cell surface via binding to the antigen, and effector cells such as NK cells bind to the Fc regions of the antibody, and this causes the effector cells to induce cytotoxicity against cells expressing the target antigen. In contrast, the antibody which is used as ADC is preferably internalized into cells after binding to the antigen. As one can estimate from the aforementioned action mechanism, it is normally considered that preferably an antibody that damages target cells by cytotoxicity such as ADCC has a low internalization activity, and an antibody that damages target cells in the form of an ADC has a high internalization activity (Anticancer Research (1993) 13, 2207-2212). Surprisingly in contrast to this, anti-Epiregulin antibodies of the present application not only suppress proliferation of Epiregulin-expressing cells by their neutralizing activity, but also induce cell damage to Epiregulin-expressing cells by cytotoxicities such as ADCC; and meanwhile, antibody-drug conjugates containing anti-Epiregulin antibodies of the present application have also been found to induce cytotoxicity against Epiregulin-expressing cells.

Low-Molecular-Weight Antibody

In a non-limiting embodiment, anti-Epiregulin antibodies included in the anti-Epiregulin antibody-drug conjugate of the present invention may be low-molecular-weight antibodies. A low-molecular weight antibody contains an antibody fragment lacking a portion of a whole antibody (for example, whole IgG). As long as it has the activity to bind the Epiregulin antigen, partial deletions of an antibody molecule are permissible. Antibody fragments of the present invention preferably contain a heavy-chain variable region (VH) and/or a light-chain variable region (VL). The amino acid sequence of VH or VL may have substitutions, deletions, additions, and/or insertions. Furthermore, as long as it has the activity to bind the Epiregulin antigen, VH and/or VL can be partially deleted. The variable region may be chimerized or humanized. Specific examples of the antibody fragments include Fab, Fab', F(ab')$_2$, and Fv. Specific examples of low-molecular-weight antibodies include Fab, Fab', F(ab')$_2$, Fv, scFv (single chain Fv), diabody, and sc(Fv)$_2$ (single chain (Fv)$_2$). Multimers of these antibodies (for example, dimers, trimers, tetramers, and polymers) are also included in the low-molecular-weight antibodies of the present invention.

Low-molecular-weight antibodies can be obtained by treating an antibody with an enzyme to produce antibody fragments. Known enzymes that produce antibody fragments are, for example, papain, pepsin, and plasmin. Alternatively, genes encoding these antibody fragments can be inserted into expression vectors; an appropriate host cells introduced with the expression vectors are cultured to express antibody fragment; and then the antibody fragment can be obtained by isolating from the culture medium and purifying them (see, for example, Co et al., (J. Immunol. (1994) 152, 2968-2976); Better et al., (Methods in Enzymology (1989) 178, 476-496); Plueckthun et al., (Methods in Enzymology (1989) 178, 476-496); Lamoyi (Methods in Enzymology (1989) 121, 652-663); Rousseaux et al., (Methods in Enzymology (1989) 121, 663-669); Bird et al., (TIBTECH (1991) 9, 132-137).

A diabody refers to a bivalent antibody fragment constructed by gene fusion (Hollinger et al., Proc. Natl. Acad. Sci. USA (1993) 90: 6444-6448; EP 404,097; WO 1993/11161; and such). A diabody is a dimer composed of two polypeptide chains. Generally, in each polypeptide chain constituting the dimer, VL and VH are linked by a linker within the same chain. The linker in a diabody is generally short enough to prevent binding between VL and VH. Specifically, the amino acid residues constituting the linker are, for example, five residues or so. Therefore, VL and VH that are encoded by the same polypeptide chain cannot form a single-chain variable region fragment, and form a dimer with another single chain variable region fragment. As a result, diabodies have two antigen binding sites. scFv can be obtained by ligating the H-chain V region and L-chain V region of an antibody. Specifically, scFv can be prepared by ligating the H-chain V region and L-chain V region via a linker, preferably a peptide linker (Huston et al., Proc. Natl. Acad. Sci. U.S.A., (1988) 85, 5879-5883). The H-chain V region and L-chain V region of scFv may be derived from any of the antibodies described herein as anti-Epiregulin antibodies. The structure and property of peptide linker for ligating the V regions is not particularly limited. For example, any single-chain peptide consisting of 3 to 25 residues or so can be used as the linker.

sc(Fv)$_2$ is a low-molecular-weight antibody prepared by ligating two VHs and two VLs with linkers or such to form a single chain (Hudson et al., J. Immunol. Methods (1999) 231, 177-189). sc(Fv)$_2$ can be produced, for example, by linking scFvs with a linker.

Pharmaceutical Compositions

In another aspect, the present invention provides pharmaceutical compositions comprising an anti-Epiregulin antibody of the present invention as an active ingredient. Furthermore, the present invention relates to cell growth inhibitors, in particular, anticancer agents or agents for suppressing cancer recurrence or metastasis, which comprise an anti-Epiregulin antibody of the present invention as an active ingredient. Preferably, the cell growth inhibitors and anticancer agents or agents for suppressing cancer recurrence or metastasis of the present invention are administered to a subject who suffers from cancer or may suffer from cancer in the future.

In the present invention, cell growth inhibitors comprising an anti-Epiregulin antibody as an active ingredient can also be expressed as methods for suppressing cell growth, which comprise the step of administering an anti-Epiregulin antibody to a subject; uses of an anti-Epiregulin antibody in producing cell growth inhibitors; or anti-Epiregulin antibodies for use in suppressing cell growth.

Furthermore, in the present invention, anticancer agents or agents for suppressing cancer recurrence or metastasis comprising an anti-Epiregulin antibody as an active ingredient can also be expressed as methods for preventing or treating cancer or methods for suppressing cancer recurrence or metastasis, which comprise the step of administering an anti-Epiregulin antibody to a subject; use of an anti-Epiregulin antibody in producing anticancer agents or agents for suppressing cancer recurrence or metastasis; or anti-Epiregulin antibodies for use in preventing or treating cancer or suppressing cancer recurrence or metastasis.

In the present invention, "comprising an anti-Epiregulin antibody as an active ingredient" means comprising an anti-Epiregulin antibody as the major active ingredient, and there is no limitation on the content of the anti-Epiregulin antibody. The antibodies included in the pharmaceutical compositions of the present invention (for example, cell growth inhibitors and anticancer agents of the present invention; and the same hereinafter) are not particularly limited as long as they bind to the Epiregulin protein, and can be exemplified by the antibodies described herein.

The pharmaceutical compositions of the present invention can be administered to subjects (patients) either orally or parenterally. Parenteral administration is preferred. Such administration methods specifically include administration by injection, transnasal administration, pulmonary administration, and transdermal administration. For administration by injection, a pharmaceutical composition of the present invention can be systemically or locally administered by, for example, intravenous injection, intramuscular injection, intraperitoneal injection, and subcutaneous injection. The method of administration can be selected appropriately according to the age and symptoms of the patient. The dose can be selected, for example, within the range from 0.0001 mg to 1000 mg per kilogram body weight per administration. Alternatively, the dose may be selected, for example, within the range from 0.001 mg/body to 100000 mg/body per patient. However, the pharmaceutical compositions of the present invention are not limited to these doses.

The pharmaceutical compositions of the present invention can be formulated according to conventional methods (for example, Remington's Pharmaceutical Science, latest edition, Mark Publishing Company, Easton, U.S.A), and may also contain pharmaceutically acceptable carriers and additives. Examples include surfactants, excipients, coloring agents, flavoring agents, preservatives, stabilizers, buffers, suspending agents, isotonization agents, binders, disintegrants, lubricants, fluidity-promoting agents, and corrigents. Without limitation to these, other commonly used carriers can be suitably used. Specific examples of carriers include light anhydrous silicic acid, lactose, crystalline cellulose, mannitol, starch, carmellose calcium, carmellose sodium, hydroxypropyl cellulose, hydroxypropyl methyl cellulose, polyvinylacetal diethyl aminoacetate, polyvinylpyrrolidone, gelatin, medium-chain fatty acid triglycerides, polyoxyethylene hardened castor oil 60, saccharose, carboxymethyl cellulose, corn starch, inorganic salts, and such.

The anti-Epiregulin antibodies are described above as Epiregulin protein-binding antibodies included in the pharmaceutical compositions of the present invention. Cells that are bound by the anti-Epiregulin antibodies are not particularly limited as long as the cells are Epiregulin-expressing cells. Preferred Epiregulin-expressing cells of the present invention are cancer cells. More preferably, the cells are colon cancer cells, lung adenocarcinoma cells, pancreatic cancer cells, stomach cancer cells, esophageal cancer cells, and kidney cancer cells. Methods of the present invention can be applied to both primary and metastatic foci of these cancers. More preferred cancer cells are primary colon cancer cells, metastatic colon cancer cells, and pancreatic cancer cells.

In the present invention "contacting" is accomplished, for example, by adding an antibody to a culture solution of Epiregulin-expressing cells cultured in a test tube. In this case, the antibody can be added in the form of, for example, a solution or a solid obtained by freeze-drying or the like. When adding the antibody as an aqueous solution, the aqueous solution used may purely contain only the antibody, or the solution may include, for example, the above-mentioned surfactants, excipients, coloring agents, perfumes, preservatives, stabilizers, buffers, suspending agents, isotonization agents, binders, disintegrants, lubricants, fluidity promoting agents, or flavoring agents. The concentration for addition is not particularly limited, but the final concentration in the culture that may be suitably used is preferably in the range of 1 pg/mL to 1 g/mL, more preferably 1 ng/mL to 1 mg/mL, and even more preferably 1 µg/mL to 1 mg/mL.

Furthermore, in another embodiment, "contacting" in the present invention is carried out by administration of an antibody to a non-human animal to which an Epiregulin-expressing cell has been transplanted into the body, or to an animal carrying cancel cells endogenously expressing Epiregulin. The method of administration may be oral or parenteral administration. The method of administration is particularly preferably parenteral administration, and specifically, the method of administration is, for example, administration by injection, transnasal administration, transpulmonary administration, or transdermal administration. Examples of administration by injection include systemic and local administrations of pharmaceutical compositions, cell proliferation inhibitors and anticancer agents of the present invention by intravenous injection, intramuscular injection, intraperitoneal injection, subcutaneous injection, or such. A suitable administration method may be selected according to the age of the test animal and symptoms. When administering as an aqueous solution, the aqueous solution used may purely contain only the antibody, or the solution may include, for example, the above-mentioned surfactants, excipients, coloring agents, perfumes, preservatives, stabilizers, buffers, suspending agents, isotonization agents, binders, disintegrants, lubricants, fluidity promoting agents, or flavoring agents. The dosage may be selected, for example, within the range of 0.0001 mg to 1000 mg per kg body weight in each administration. Alternatively, for example, the dosage for each patient may be selected within the range of 0.001 to 100,000 mg/body. However, the antibody dose of the present invention is not limited to these doses.

Therapeutic Agents for Cancer or Agents for Suppressing Cancer Recurrence or Metastasis which are Administered to Subjects Carrying epiregulin Protein-Expressing Cancer Cells The present invention provides therapeutic agents for cancer or agents for suppressing cancer recurrence or metastasis, wherein the subjects administered with the therapeutic agents for cancer or agents for suppressing cancer recurrence or metastasis are subjects carrying Epiregulin protein-expressing cancer cells, which are detected using an isolated tissue sample. Besides the methods described herein, the expression level of the Epiregulin protein can be determined by methods known to those skilled in the art. To determine whether or not a subject is to be administered with therapeutic agents for cancer or agents for suppressing cancer recurrence or metastasis of the present invention, the expression level of the Epiregulin protein can be determined in a tissue sample isolated from a candidate subject. If the Epiregulin protein is detected in the sample, the subject from which the sample is derived can be the subject to be administered with therapeutic agents for cancer or agents for suppressing cancer recurrence or metastasis of the present invention. The expression level of the Epiregulin protein is not limited to a particular numerical value, but in a non-limiting embodiment, it can be set appropriately from the range of numerical values in the order of $10^3$, $10^4$, $10^5$, $10^6$, $10^7$, and $10^8$. As a non-limiting embodiment, the expression level of the Epiregulin protein selected from any one of $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^4$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, and $9\times10^8$ can be shown as a preferred example of the numerical value (threshold value) that can be set as the standard for selecting subjects who will receive the administration. The numerical values mentioned above may be those calculated to one significant figure; and in this case, for example, the EREG expression level of $1\times10^3$ calculated to one significant figure can be an EREG expression level having a numerical value of any one of $0.5\times10^3$, $0.6\times10^3$, $0.7\times10^3$, $0.8\times10^3$, $0.9\times10^3$, $1.0\times10^3$, $1.1\times10^3$, $1.2\times10^3$, $1.3\times10^3$, $1.4\times10^3$ if calculated to two significant figures.

Tissue Samples

The term "tissue sample" used in the present invention refers to any biological sample that can be obtained from an individual, body fluid (for example, blood, serum, plasma, and spinal fluid), tissue culture, tissue sections, or such.

Samples from subjects can be used as preferred examples of biological samples. Preferred samples from subjects are tissues obtained from subjects, and more preferably colon tissues from subjects. Biopsy, a known method, is preferably used as a method for collecting colon tissues. Known means can be used appropriately as the means for biopsy. Such examples include obtaining tissues by biopsy such as aspiration biopsy, clutch biopsy, sponge biopsy, biopsy for cytodiagnosis, endoscopic biopsy, fine-needle aspiration biopsy, needle biopsy, transbronchial lung biopsy, or obtaining tissues during surgery.

In the present invention, since the tissue samples are observed with transmitted light under a microscope, they are sliced to such an extent that the light used on the microscope is sufficiently transmitted through the tissue samples. Prior to slicing, the tissue samples are fixed. Specifically, the tissue samples are solidified by dehydrating or denaturing proteins in the tissues/cells to rapidly kill the cells constituting the tissues. The resulting tissues have a stabilized and insolubilized structure. First, the tissue samples to be fixed are cut into fragments having a size and a shape suitable for preparing paraffin-embedded sections using a cutting knife such as a scalpel. Subsequently, the fragments are immersed into a fixing solution, a reagent used for carrying out fixation. The fixing solution used is preferably formalin, or more preferably neutral buffered formalin. The concentration of the neutral buffered formalin is appropriately selected according to the characteristics or physical properties of the tissue samples. The concentration can be appropriately changed and used between 1% and 50%, preferably between 5% and 25%, and more preferably between 10% and 15%. The fixing solution into which the tissue preparations have been immersed is appropriately deaerated using a vacuum pump. The fixation is carried out by leaving the tissue samples in the fixing solution for several hours under normal pressure and room temperature conditions. The time required for the fixation can be selected appropriately within the range of 1 hour to 7 days, preferably 2 hours to 3 days, or preferably 3 hours to 24 hours, and more preferably 4 hours to 16 hours. The fixed samples are further appropriately immersed into a phosphate buffer or such for several hours (the time can be selected appropriately within the range of 2 hours to 48 hours, preferably 3 hours to 24 hours, and more preferably 4 hours to 16 hours).

Next, from the fixed tissue samples, sections can be prepared preferably using a freeze sectioning method or a paraffin sectioning method. Preferred examples of the freeze sectioning method include a method which involves freezing the tissues by placing them into O.C.T. compound (Miles. Inc.), and slicing the frozen tissues using a Cryostat (frozen section preparing apparatus). In the paraffin sectioning method, the fixed tissue samples are immersed into an embedding agent, which is then fixed to thereby confer uniform and appropriate hardness to the sections. Paraffin can be used preferably as an embedding agent. The fixed tissue samples are dehydrated using ethanol. Specifically, the tissue samples are dehydrated by sequentially immersing the tissue samples into 70% ethanol, 80% ethanol, and 100% ethanol. The time and number of times required for the immersion can be selected appropriately within the ranges of 1 hour to several days and once to three times, respectively. Moreover, the immersion may be performed at room temperature or at 4° C. For the immersion at 4° C., a longer immersing time, for example overnight, is preferable. Subsequently, the liquid phase is replaced by xylene, and then the tissue samples are embedded in paraffin. The time required for the xylene replacement of the liquid phase can be selected appropriately within the range of one hour to several hours. In this procedure, the replacement may be performed at room temperature or at 4° C. For the replacement at 4° C., a longer replacement time, for example, overnight is preferable. The time and number of times required for the paraffin embedding can be selected appropriately within the ranges of one hour to several hours and once to four times, respectively. In this procedure, the embedding may be performed at room temperature or at 4° C. For embedding at 4° C., a longer embedding time, for example, overnight is preferable. Moreover, the tissue samples can be paraffin-embedded preferably by use of a paraffin embedding apparatus (for example, EG1160, Leica) which automatically processes the paraffin embedding reaction.

The paraffin-embedded tissue samples as described above are attached to a base to prepare a "block", which is then sliced using a microtome to a desired thickness selected from thicknesses of 1 μm to 20 μm. The thinly sliced tissue sections are left to stand on slide glass used as a transparent support for bonding. In this case, slide glasses coated with 0.01% poly-L-lysine (Sigma) and dried can also be used preferably to prevent peel-off of the tissue sections. The fixed tissue sections are air dried for an appropriate period of time selected from between several minutes to an hour.

Antigen Retrieval

In the method of the present invention, the reactivity of an antigen of which antibody reactivity has been decreased due to formalin fixation is retrieved. In the present invention, a protease-induced epitope retrieval method (PIER method) is applied to one of the two tissue samples, while a heat-induced epitope retrieval method (HIER method) is applied to the other sample. Then, the difference in the degree of staining between them after antibody reaction is digitized.

The heat-induced epitope retrieval method appropriately utilizes a microwave heating method, an autoclave heating method, a heating method by boiling treatment, or the like. When the boiling treatment is performed at an output of 780 W to keep the temperature of the solution at approximately 98° C., the time required for the retrieval including the treatment is appropriately selected from between five and 60 minutes and is, for example, ten minutes. The antigen retrieval treatment can be performed in a 10 mM sodium citrate buffer as well as the commercially available Target Retrieval Solution (DakoCytomation) or such. In the Examples described later, the Target Retrieval Solution is used. Any buffer or aqueous solution is preferably used as long as an epitope in the antigen recognized by an Epiregulin antibody acquires binding to the antibody as a result of retrieval treatment such that an antigen-antibody complex described later can be detected.

The type or origin of protease used in the protease-induced epitope retrieval method is not particularly limited, and generally an available protease can appropriately be selected and used. Preferred examples of the protease to be used include 0.05% pepsin in 0.01N hydrochloric acid, 0.1% trypsin further containing 0.01% $CaCl_2$ in a Tris buffer at pH 7.6, and 1 to 50 μg/ml protease K in a 10 mM Tris-HCl buffer at pH 7.8 containing 10 mM EDTA and 0.5% SDS. Furthermore, when protease K is used, the pH of its reaction solution is appropriately selected from between 6.5 and 9.5, and an SH reagent, a trypsin inhibitor, or a chymotrypsin inhibitor may be used appropriately. Protease attached to the Histofine HER2 Kit (MONO) (Nichirei Bioscience) described herein in the Examples is also included in such specific examples of preferred protease. The protease-induced epitope retrieval is usually performed at 37° C.

However, the reaction temperature can be changed appropriately within the range of 25° C. to 50° C. When the protease-induced epitope retrieval is performed at 37° C., the reaction time is appropriately selected from between, for example, one minute and five hours and is, for example, 15 minutes, 30 minutes, 45 minutes, 1 hour, 2 hours, 3 hours, or 4 hours. After completion of the retrieval treatment, the treated tissue samples are washed with a wash buffer. PBS (phosphate-buffered saline) is preferably used as the wash buffer. In addition, a Tris-HCl buffer can be used preferably. The washing conditions usually adopt a method involving performing 5-minute washes at room temperature three times. However, the wash time and temperature can be changed appropriately.

Substances for detection used in the present invention generally include antibodies, nucleic acids, and such. For example, it is possible to (1) detect the EREG protein by an immunological method using EREG antibodies that can detect the EREG protein, and (2) detect EREG-encoding mRNA using a nucleic acid molecule (for example, DNA, RNA, or mRNA) complementary to the EREG-encoding mRNA which can detect the mRNA, or suitably a complementary nucleic acid molecule, wherein the detection makes use of hybridization between the nucleic acid molecules involved (for example the FISH method). In the present invention, immunological techniques, in particular, immunohistological staining is preferably used.

Reaction of Tissue Samples with an Epiregulin Antibody

The tissue sample subjected to the antigen retrieval treatment based on the heat-induced epitope retrieval method and the tissue sample subjected to the antigen retrieval treatment based on the protease-induced epitope retrieval method are reacted with an Epiregulin antibody as the primary antibody. This reaction is carried out under conditions appropriate for recognition of an epitope in the antigen by the Epiregulin antibody and formation of an antigen-antibody complex. The reaction is usually performed overnight at 4° C. or at 37° C. for one hour. However, the reaction conditions can be changed appropriately within a range suitable for recognition of an epitope in the antigen by the antibody and formation of an antigen-antibody complex. For example, the reaction temperature can be changed within the range of 4° C. to 50° C., and the reaction time can be changed between one minute and seven days. When performing the reaction at a low temperature, longer reaction time is preferable. After the primary antibody reaction is completed, the tissue samples are washed with a wash buffer. PBS (phosphate-buffered saline) is preferably used as the washing buffer. In addition, a Tris-HCl buffer can also be used preferably. The washing conditions usually adopt a method involving 5 minute-washes at room temperature three times. However, the washing time and temperature can be changed appropriately.

Subsequently, the tissue samples subjected to the primary antibody reaction are reacted with a secondary antibody that recognizes the primary antibody. A secondary antibody labeled in advance with a labeling substance for visualizing the secondary antibody is usually used. Preferred labeling substance include: fluorescent dyes such as fluorescein isothiocyanate (FITC), Cy2 (Amersham), and Alexa488 (Molecular Probes); enzymes such as peroxidase and alkaline phosphatase; and colloidal gold.

The reaction with the secondary antibody is carried out under conditions appropriate for formation of an antigen-antibody complex by the Epiregulin antibody and the secondary antibody that recognizes the Epiregulin antibody. The reaction is usually performed at room temperature or 37° C. for 30 minutes to one hour. However, the reaction conditions can be changed appropriately within a range suitable for formation of an antigen-antibody complex by the Epiregulin antibody and the secondary antibody. For example, the reaction temperature can be changed within the range of 4° C. to 50° C., and the reaction time can be changed between one minute and seven days. When performing the reaction at a low temperature, longer reaction time is preferable. After the secondary antibody reaction is completed, the tissue samples are washed with a wash buffer. PBS (phosphate-buffered saline) is preferably used as the wash buffer. In addition, a Tris-HCl buffer can also be used preferably. The washing conditions usually adopt a method involving 5 minute-washes at room temperature three times. However, the washing time and temperature can be changed appropriately.

Next, the tissue samples subjected to the secondary antibody reaction are reacted with a substance for visualizing the labeling substance. When peroxidase is used as the labeling substance for the secondary antibody, the tissue samples are incubated with a reaction solution obtained by mixing, immediately before the incubation, equal amounts of a 0.02% aqueous hydrogen peroxide solution and a DAB (diaminobenzidine) solution adjusted to a concentration of 0.1% with a 0.1 M Tris-HCl buffer (pH 7.2). In addition to DAB, chromogenic substrates such as DAB-Ni and AEC+ (all DAKO) can be selected appropriately. During the course of incubation, the degree of color development is observed under a microscope with time. At the point where appropriate color development is confirmed, the visualization reaction is terminated by immersing the tissue samples in PBS.

When alkaline phosphatase is used as a labeling substance for the secondary antibody, the tissue samples are incubated with a BCIP (5-bromo-4-chloro-3-indolyl phosphate)/NBT (nitro blue tetrazolium) (Zymed) substrate solution (NBT at a concentration of 0.4 mM and BCIP at a concentration of 0.38 mM are dissolved in a 50 mM sodium carbonate buffer (pH 9.8) containing 10 mM $MgCl_2$ and 28 mM NaCl). Moreover, in addition to BCIP and NBT, Permanent Red, Fast Red, or Fuchsin+ (all DAKO) may be used appropriately. Prior to the incubation, the tissue samples may be preincubated at room temperature for one minute to several hours with a 0.1 M Tris-HCl buffer (pH 9.5) containing 0.1 M sodium chloride, 50 mM magnesium chloride, and levamisole chloride which is an inhibitor of endogenous alkaline phosphatase (Nacalai Tesque) at a concentration of 1 mM. During the course of incubation, the tissue samples are observed under a microscope with time. At the point where the deposits of purple formazan, a final reaction product, are observed, the reaction is terminated by washing the tissue samples with water or by adding TBS containing 2% polyvinyl alcohol. Then, the tissue samples are washed with TBST (TBS containing 0.1% Tween 20). When colloidal gold is used as a label for the secondary antibody, the colloidal gold is visualized by attaching metallic silver to the gold particles by silver enhancement. The silver enhancement method is known to those skilled in the art.

When any one of the fluorescent dyes such as FITC (fluorescein isothiocyanate), Cy2 (Amersham), and Alexa488 (Molecular Probes, Inc.) is used as a labeling substance for the secondary antibody, a reaction step for visualizing the substance is unnecessary. A light emitted by irradiation with a light at the excitation wavelength of the fluorescent substance can be detected appropriately by using a fluorescence microscope.

In the present invention, the Epiregulin protein contained in the tissue samples isolated from test subjects is detected as described above. Whether the detected Epiregulin protein contained in the tissue samples is highly expressed in tissues containing cancer cells can be determined by staining intensity scores which digitize the staining patterns obtained by the above-mentioned immunohistological staining method. The following criteria can be exemplified as a non-limiting embodiment of the digitization of staining patterns:

Staining intensity score of 0: none or less than 10% of the tumor cells in the tested tissue are Epiregulin-positive cells;

Staining intensity score of 1: Epiregulin-positive cells account for 10% or more of the tumor cells in the tested tissue but have a weak staining intensity localized to a portion of the tumor cell membrane;

Staining intensity score of 2: Epiregulin-positive cells account for 30% or more of the tumor cells in the tested tissue, or Epiregulin-positive cells account for 10% or more of the tumor cells in the tested tissue and have a moderate staining intensity localized to the tumor cell membrane; and Staining intensity score of 3: Epiregulin-positive cells account for 60% or more of the tumor cells in the tested tissue, or Epiregulin-positive cells account for 10% or more of the tumor cells in the tested tissue and have a strong staining intensity localized to the tumor cell membrane.

Furthermore, in the present invention, when determining the expression level of Epiregulin in tissue samples isolated from test subjects based on the staining intensity scores which digitize the staining patterns obtained by the immunohistological staining method described above, one can compare with the images of the staining patterns for predetermined expression levels of the Epiregulin protein prepared for detection correction. To determine the expression level of Epiregulin protein, a known method which uses fluorescence-labeled beads used to prepare a calibration curve for antigen quantification (for example, BD Quantibrite PE™) can be used appropriately.

Whether or not Epiregulin contained in a tissue sample isolated from a test subject is highly expressed can be determined by the above-mentioned method. Examples of "highly expressed" may be suitably selected from the range of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^5$, $1\times10^7$, $2\times10^7$, $3\times10^7$, $4\times10^7$, $5\times10^7$, $6\times10^7$, $7\times10^7$, $8\times10^7$ and $9\times10^7$ in terms of the number of Epiregulin molecules expressed per cell.

All prior art references cited in the present specification are herein incorporated by reference.

EXAMPLES

Herein below, the present invention will be more specifically described by way of the Examples, but is not to be limited thereto.

Example 1

Humanization of the Chimeric Antibody EP27

1-1. Selection of Framework Sequences for Humanization

The chimeric antibody EP27 (described in WO 2008/047723) comprising mouse variable regions and human IgG1 constant regions was humanized. The CDR and FR were determined according to the Kabat definition (Kabat numbering).

First, human antibody variable region sequences and EP27 mouse variable region sequences on databases were compared to select the human FR sequences below which can be used as a humanization template. The IMGT Database (www.imgt.org) and NCBI GenBank (www.ncbi.nim-.nih.gov/genbank) were used as databases. The selected FR sequences are shown in Table 2.

TABLE 2

| Framework | Accession number | Database name | SEQ ID NO |
|---|---|---|---|
| H chain FR1 | M99642 | IMGT Database | 1 |
| H chain FR2 | L22582 | IMGT Database | 2 |
| H chain FR3 | AJ252274 | NCBI GenBank | 3 |
| H chain FR4 | J00256 | IMGT Database | 4 |
| L chain FR1 | M64856 | IMGT Database | 5 |
| L chain FR2 | X01668 | IMGT Database | 6 |
| L chain FR3 | M64856 | IMGT Database | 7 |
| L chain FR4 | J00242 | IMGT Database | 8 |

Subsequently, humanized antibody variable region sequences were designed by linking the CDR sequences (Table 3, SEQ ID NOs: 9 to 14) of the H and L chains of the EP27 variable region to the human FR selected above. They were designated as the humanized H-chain variable region sequence HA (SEQ ID NO: 15) and humanized L-chain variable region sequence LA (SEQ ID NO: 16).

TABLE 3

| CDR | SEQ ID NO |
|---|---|
| H chain CDR1 | 9 |
| H chain CDR2 | 10 |
| H chain CDR3 | 11 |
| L chain CDR1 | 12 |
| L chain CDR2 | 13 |
| L chain CDR3 | 14 |

1-2. Design of the Humanized EP27 Variable Region HJ

It is reported that in the H-chain FR1 sequence selected in Table 2, the amino acid residues at positions 2, 4, 24, 27, and 29 indicated by Kabat numbering contribute to stabilization of the antibody structure by upper core formation (Ewert et al., Methods. 2004 October;34(2): 184-99). According to the Chothia definition, the amino acid residues at positions 26 to 30 indicated by Kabat numbering are included in the CDR1 (Honegger et al., J. Mol. Biol. (2001) 309, 657-670). Based on the above information, to prepare a humanized antibody having an antigen binding activity equivalent to that of the chimeric antibody EP27, the above-mentioned amino acid residues were restored to the residues present in the EP27 mouse variable region sequence. Thus, the humanized H-chain FR1 (Table 4, SEQ ID NO: 17) was newly designed by restoring the amino acid residues at positions 2, 24, 27, 28, 29, and 30, indicated by Kabat numbering, in the human H-chain FR1 (SEQ ID NO: 1) selected in Table 2, to the amino acid residues present in the EP27 mouse variable region sequence.

The amino acid residue at position 93 indicated by Kabat numbering in the H-chain FR3 sequence selected in Table 2 is Ala, while the residue in the EP27 mouse variable region sequence is Val. Based on the IMGT Database (www.imgt.org) of mouse and human germline sequences, it was confirmed that only a small number of sequences contain Val at the corresponding position. The Val at position 93, indicated by Kabat numbering, in the EP27 mouse variable region sequence is considered to be involved in antigen binding. Thus, the humanized H-chain FR3 (Table 4, SEQ ID NO: 18) was newly designed by substituting the amino acid residue at position 93, indicated by Kabat numbering, in the human H-chain FR3 (SEQ ID NO: 3) selected in Table 2, with the residue present in the EP27 mouse variable region sequence.

From the humanized H chain variable region sequence HA (SEQ ID NO: 15), the humanized H chain variable region sequence HJ (SEQ ID NO: 19) comprising the FR1 (Table 4, SEQ ID NO: 17) and FR3 (Table 4, SEQ ID NO: 18) newly designed and shown in Table 4, was newly designed.

TABLE 4

| Altered FR | SEQ ID NO |
|---|---|
| H chain FR1 | 17 |
| H chain FR3 | 18 |

1-3. Design of the EP27 Humanized Variable Regions LB and L18

The amino acid residue at position 49, indicated by Kabat numbering, in the L-chain FR2 sequence selected in Table 2 is Tyr, while the residue in the EP27 mouse variable region sequence is Gln. Based on the IMGT Database (www.imgt.org) of mouse and human germline sequences, it was confirmed that only a small number of sequences contain Gln at the corresponding position. This suggested the possibility that Gln at position 49 contained in the EP27 mouse variable region sequence is involved in antigen binding. Based on this, the humanized L-chain FR2 (Table 5, SEQ ID NO: 20) was newly designed by substituting the amino acid residue at position 49, indicated by Kabat numbering, in the human L-chain FR2 (SEQ ID NO: 6) selected in Table 2 with the amino acid residue present in the EP27 mouse variable region sequence.

It is reported that in the L-chain FR3 sequence selected in Table 2, the amino acid residue at position 71, indicated by Kabat numbering, contributes to stabilization of the antibody structure by upper core formation (Ewert et al., Methods. 2004 October; 34(2): 184-99). To prepare a humanized antibody having an antigen binding activity equivalent to that of the chimeric antibody EP27, to substitute the above amino acid residue with the amino acid residue of the EP27 mouse variable region sequence, the humanized L-chain FR3 (Table 5, SEQ ID NO: 21) was newly designed by substituting the amine acid residue at position 71, indicated by Kabat numbering, in the human L-chain FR3 (SEQ ID NO: 7) selected in Table 2 with the amino acid residue in the EP27 mouse variable region sequence.

From the humanized L-chain variable region sequence LA (SEQ ID NO: 16), the humanized L-chain variable region sequence LB (SEQ ID NO: 22) comprising the newly designed FR2 and FR3 (Table 5, SEQ ID NOs: 20 and 21) was designed.

Also, from the humanized L-chain variable region sequence LA (SEQ ID NO: 16), the humanized L-chain variable region sequence L18 (SEQ ID NO: 24) comprising the newly designed FR2 (Table 5, SEQ ID NO: 20) and FR3 of the human antibody L chain sequence (Table 5, SEQ ID NO: 23) shown in Accession No. AB064134 (NCBI GenBank) was designed.

TABLE 5

| Altered FR | SEQ ID NO |
|---|---|
| H chain FR2 | 20 |
| H chain FR3 | 21 |
| H chain FR3 | 23 |

1-4. Preparation of the Humanized EP27 Antibody Sequence

First, to prepare a cDNA of the humanized EP27 variable region, synthetic oligo-DNAs were designed for the H (HJ) and L (LB) chains. Next, the synthetic oligo-DNAs were mixed to amplify a gene fragment encoding the variable region of the humanized EP27 antibody by a method known to those skilled in the art, such as assembly PCR. Finally, the amplified fragment was cloned in an appropriate animal cell expression vector, and was ligated to a human IgG1 constant region gene. The nucleotide sequence of the resulting expression vector was determined by a method known to those skilled in the art.

For the heterogeneity derived from the C-terminal sequence (G1, SEQ ID NO: 25) of the human IgG antibody H chain, deletion of the lysine residue at the C-terminal amino acid, and amidation of the C-terminal amino group by deletion of two C-terminal amino acids, glycine and lysine, has been reported (Anal Biochem. 2007 Jan. 1; 360(1): 75-83.). As a method for reducing the heterogeneity, a method that deletes two amino acids at the C terminus of the H chain, i.e., glycine at position 446 and lysine at position 447, indicated by EU numbering, is known (WO 2009/041613). Desirably, the heterogeneity derived from the C-terminal sequence of the H chain is also absent from the humanized EP27 antibody. Thus, the IgG1 sequence (G1d, SEQ ID NO: 26) lacking glycine at position 446 and lysine at position 447, indicated by EU numbering, in the human IgG1 can be used as a constant region sequence. On the other hand, a native human κ chain (k, SEQ ID NO: 27) can be used as the constant region sequence of the L-chain constant region. HJ-G1d (SEQ ID NO: 28) and LB-k (SEQ ID NO: 29) were prepared respectively as H chain and L chain for the humanized EP27 antibody sequence obtained as described above. Allotypes were reported for the IgG1 constant region (Jefferis et al., mAbs 1: 4, 1-7; July/August 2009). Besides the above-mentioned G1m17,1-type constant region (SEQ ID NO: 26) of IgG1, the G1m17 (SEQ ID NO: 30) and G1m3 (SEQ ID NO: 31) types can be used for the preparation of the humanized EP27 antibody.

1-5. Evaluation of the Humanized EP27 Antibody

To evaluate the designed humanized EP27 antibody sequence, the H chain (HJ-G1d, SEQ ID NO: 28) and L chain (LB-k, SEQ ID NO: 29) were co-expressed to obtain the humanized EP27 antibody HJ-G1d/LB-k. Specifically, the H and L chain expression vectors prepared as mentioned above were transiently transfected into the human embryonic kidney carcinoma cell-derived HEK293II strain (Invitrogen) or FreeStyle293 cells (Invitrogen) to express antibodies. From the culture supernatant obtained, antibodies were purified by a method known to those skilled in the art using rProtein A Sepharose™ Fast Flow (GE Healthcare) or the like. The absorbance of an antibody-containing solution was measured at the 280-nm wavelength using a spectrophotometer, and the antibody concentration was calculated using the absorbance measured and the absorbance coefficient determined by the PACE method (Protein Science 1995; 4: 2411-2423). Meanwhile, cH-G1/cL-k which is the chimeric antibody EP27 was prepared as a control by the same method using the H (cH-G1, SEQ ID NO: 32) and L (cL-k, SEQ ID NO: 33) chains.

The ability of the humanized EP27 antibody to bind human epiregulin (SEQ ID NO: 167) was evaluated using an epiregulin binding inhibition evaluation assay (Reference example 5) for the chimeric antibody EP27. If the IC50 concentration of the chimeric antibody EP27 (cH-G1/cL-k) was set to 100, the value of the humanized EP27 antibody HJ-G1d/LB-k was 24.

1-6. Preparation of Humanized EP27 Antibodies with Activity Equivalent to that of the Chimeric Antibody Sequences were designed with substitution of some amino acid residues of the FR sequence in the H chain sequence HJ-G1d of the humanized EP27 antibody with amino acid residues of the EP27 mouse variable region sequence. First, a sequence (SEQ ID NO: 35) was designed with substitution of Thr-Asp, which are the amino acid residues at positions 75 and 76 indicated by Kabat numbering of the human FR3 sequence, with Ser-Asn which are amino acid residues contained in the EP27 mouse variable region sequences; and a sequence (SEQ ID NO: 36) was designed with substitution of only Asp at position 76 with Asn which is an amino acid residue of the EP27 mouse variable region sequence (Table 6). Next, HS-G1d (SEQ ID NO: 37) which is a humanized H-chain variable region sequence having an FR3 sequence (SEQ ID NO: 35) shown in Table 6 was prepared by introducing a mutation into an expression vector comprising the humanized H-chain variable region sequence HJ-G1d (SEQ ID NO: 28). The amino acid residue substitution was introduced by a method known to those skilled in the art using PCR or the like. Similarly, HY-G1d (SEQ ID NO: 38) was prepared, which is a humanized H-chain variable region sequence comprising an FR3 sequence (SEQ ID NO: 36) shown in Table 6. Humanized EP27 antibodies, HS-G1d/LB-k, HY-G1d/LB-k, and HY-G1d/L18-k, were obtained in the same manner as in Example 1-4. The ability of the obtained antibodies to bind to human epiregulin was evaluated by the inhibition of epiregulin binding to the chimeric antibody EP27 (Reference Example 5). As a result, if the IC50 concentration of the chimeric antibody EP27 (cH-G1/cL-k) was set to 100, the IC50 concentrations of the humanized EP27 antibodies, HS-G1d/LB-k, HY-G1d/LB-k, and HY-G1d/L18-k, were 142, 146, and 100, respectively.

Accordingly, humanized EP27 antibody sequences having an antigen-binding ability equivalent to that of the chimeric antibody EP27, as well as reduced immunogenicity risks compared with the chimeric antibody EP27 as a result of humanization were found.

TABLE 6

| Altered FR | SEQ ID NO |
|---|---|
| H chain FR3 | 35 |
| H chain FR3 | 36 |

Example 2

Introduction of Mutations that Suppress Deamidation, Isomerization, and Hydrolysis Reaction There is heterogeneity in antibodies used for pharmaceuticals although they are monoclonal antibodies obtained from clones derived from a single antibody-producing cell. Such heterogeneity of antibodies is known to occur as a result of modifications such as oxidation, deamidation, isomerization, and hydrolysis, and is increased when proteins including antibodies are stored for a long time or subjected to stress conditions such as heat stress and light stress (Heterogeneity of Monoclonal Antibodies: Journal of Pharmaceutical Sciences, vol.97, No.7, 2426-2447). However, the physical properties of proteins, in particular, homogeneity and stability are very important for developing antibodies as pharmaceuticals. Desirably, the heterogeneity of a substance of interest should be reduced to obtain a single material to the maximum extent.

Deamidation reaction occurs non-enzymatically in the side chains of asparagine and glutamine, and it is a reaction that changes amide present in the side chains of asparagine and glutamine into carboxylic acid. Isomerization is caused by the formation of an unstable cyclic imide intermediate due to deamidation of asparagine or dehydration of aspartic acid as a result of attack by the nitrogen atom electron pair in the C-terminal side residue on the carbonyl groups in the side chains of asparagine and aspartic acid. This intermediate is mostly changed into isoaspartic acid by cleavage, while the remainder is changed into aspartic acid. Desirably, deamidation and isomerization reaction that occur during storage of proteins such as antibodies should be suppressed as much as possible, because they cause the above-mentioned heterogeneity. It is reported that deamidation reaction tends to occur in particular at a site where glycine and asparagine are adjacent to each other (Asn-Gly) (Geiger et al., J. Biol. Chem. 1987; 262: 785-794). In addition, it is reported that the peptide chain of aspartic acid is cleaved by hydrolysis reaction; and in particular, an (Asp-Pro) sequence where proline is present at the C-terminal side is likely to be degraded under acidic conditions (Segalas et al., FEBS Letters 1995; 371: 171-175).

In the CDR sequence of the humanized H chain variable region sequence HY, asparagine and aspartic acid residues are present at positions 31 (Asp), 52 (Asp), 54 (Asn), 56 (Asn), and 101 (Asp), indicated by Kabat numbering. In the CDR sequence of the humanized L chain variable region sequence LB, they are present at positions 28 (Asp), 92 (Asp), and 93 (Asn), indicated by Kabat numbering. It was examined as to whether variants that suppress deamidation, isomerization, and hydrolysis reaction can be obtained as a result of substituting amino acid residues at these sites.

To suppress the above degradation reactions by substitution of amino acid residues, the amino acid residues were substituted into different residues. Specifically, H71-G1d (SEQ ID NO: 49), H57-G1d (SEQ ID NO: 50), H61-G1d (SEQ ID NO: 51), H65-G1d (SEQ ID NO: 52), H66-G1d (SEQ ID NO: 53), H67-G1d (SEQ ID NO: 54), H23-G1d (SEQ ID NO: 55), and H40-G1d (SEQ ID NO: 56) were prepared as H-chain genes comprising the CDR sequences (SEQ ID NOs: 39 to 46) shown in Table 7. Similarly, L30-k (SEQ ID NO: 57) and L32-k (SEQ ID NO: 58) were designed as L-chain genes comprising the CDR sequences (SEQ ID NOs: 47 and 48) shown in Table 7. Using the technique of Example 1, an H-chain gene vector introduced with a substituted residue was co-expressed with the LB-k vector to obtain the EP27 humanized antibodies, H71-G1d/LB-k, H57-G1d/LB-k, H61-G1d/LB-k, H65-G1d/LB-k, H66-G1d/LB-k, H67-G1d/LB-k, H23-G1d/LB-k, and H40-G1d/LB-k. Similarly, an L-chain gene vector introduced with a substituted residue was co-expressed with the HY-G1d vector to obtain the EP27 humanized antibody HY-G1d /L32-k. The ability of the obtained antibodies to bind to human epiregulin was evaluated as inhibition of epiregulin binding to the EP27 chimeric antibody (Reference Example 5), and the result is shown in Table 8. This demonstrates that the antibodies comprising the sequences shown in Table 7 have a binding activity equivalent to that of the chimeric antibody EP27. Thus, humanized EP27 antibody sequences with suppressed chemical degradation such as deamidation and isomerization were found.

TABLE 7

| CDR variant name | Altered CDR | SEQ ID NO |
|---|---|---|
| H71 | H chain CDR1 | 39 |
| H57 | H chain CDR2 | 40 |
| H61 | H chain CDR2 | 41 |
| H65 | H chain CDR2 | 42 |
| H66 | H chain CDR2 | 43 |
| H67 | H chain CDR2 | 44 |
| H23 | H chain CDR2 | 45 |
| H40 | H chain CDR2 | 46 |
| L30 | L chain CDR3 | 47 |
| L32 | L chain CDR3 | 48 |

TABLE 8

| Name of altered antibody | IC50 concentration |
|---|---|
| H71-G1/LB-k | 90 |
| H57-G1/LB-k | 95 |
| H61-G1/LB-k | 74 |
| H65-G1/LB-k | 78 |
| H66-G1/LB-k | 96 |
| H67-G1/LB-k | 101 |
| H23-G1/LB-k | 87 |
| H40-G1/LB-k | 83 |
| HY-G1/L30-k | 89 |
| HY-G1/L32-k | 83 |

(IC50 concentration: IC50 concentration of each antibody if the IC50 concentration of the chimeric antibody EP27 (cH-G1/cL-k) is set to be 100)

Example 3

Introduction of Mutations that Alter the Isoelectric Point

As a method of controlling the plasma half-life of an antibody, a method that modifies amino acid residues exposed on the surface of the antibody molecule to control the surface charge of the molecule (WO2007/114319 and WO2009/041543) is known. Specifically, it is known that the plasma half-life of an antibody can be extended by lowering the isoelectric point (pI) value of the antibody. On the other hand, it is known that the plasma half-life of an antibody can be shortened by increasing the isoelectric point of the antibody to improve tissue transition of the antibody (Vaisitti et al., J. Biol. Regul. Homeost. Agents. (2005) 19 (3-4), 105-112; Pardridge at al., J. Pharmacol. Exp. Ther. (1998) 286 (1), 548-554).

From the above, an EP27 humanized antibody whose isoelectric point has been altered is expected to have a stronger antitumor activity due to its extended plasma half-life and improved tissue transition. Hence, the present inventors aimed to identify amino acid residues that allow control of the pharmacokinetics of an antibody by adjusting the surface charge of the antibody molecule without affecting the antigen-binding activity and conformation of the EP27 humanized antibody. Specifically, search was carried out for mutation sites that can lower the isoelectric point of the EP27 humanized antibody HY-G1d/LB-k (H chain, HY-G1d, SEQ ID NO: 38; and L chain, LB-k, SEQ ID NO: 29) without largely reducing its antigen-binding inhibitory activity.

The three-dimensional model of the EP27 humanized antibody HY-G1d/LB-k was used to screen for residues that can alter the isoelectric point of the variable region without significantly reducing the binding to epiregulin. Specifically, H3-G1d (SEQ ID NO: 72), H5-G1d (SEQ ID NO: 73), H6-G1d (SEQ ID NO: 74), H7-G1d (SEQ ID NO: 75), H8-G1d (SEQ ID NO: 76), H9-G1d (SEQ ID NO: 77), H10-G1d (SEQ ID NO: 78), and H31-G1d (SEQ ID NO: 79) were designed as H-chain genes comprising one or more of the CDR sequences (SEQ ID NOs: 59 to 71) shown in Table 9. Similarly, L1-k (SEQ ID NO: 80), L2-k (SEQ ID NO: 81), L12-k (SEQ ID NO: 82), L20-k (SEQ ID NO: 83), L21-k (SEQ ID NO: 84), and L23-k (SEQ ID NO: 85) were designed as L-chain genes comprising the CDR sequences shown in Table 9. Using the technique of Example 1, an H-chain gene vector introduced with substituted residues was co-expressed with the LB-k vector to obtain the humanized EP27 antibodies, H3-G1d/LB-k, H5-G1d/LB-k, 116-G1d/LB-k, H7-G1d/LB-k, H8-G1d/LB-k, H9-G1d/LB-k, H10-G1d/LB-k, and H31-G1d/LB-k. Similarly, an L-chain gene vector introduced with substituted residues was co-expressed with the HY-G1d vector to obtain humanized EP27 antibodies, HY-G1d/L1-k, HY-G1d/L2-k, HY-G1d/L12-k, and HY-G1d/L63-k. The ability of the obtained antibodies to bind to human epiregulin was evaluated as inhibition of epiregulin binding to the chimeric antibody EP27 (Reference Example 5). As a result, as shown in Table 10, the antigen-binding abilities of the EP27 humanized antibodies were equivalent to that of the chimeric antibody EP27. From the above investigation, humanized EP27 antibody sequences whose isoelectric points can be altered were found.

TABLE 9

| CDR/FR variant name | Altered CDR/FR | SEQ ID NO |
|---|---|---|
| H3 | H chain CDR2 | 59 |
| H5 | H chain CDR2 | 60 |
| H6 | H chain CDR2 | 61 |
| H7 | H chain CDR2 | 62 |
| H8 | H chain CDR2 | 63 |
| H9 | H chain CDR2 | 64 |
| H10 | H chain CDR2 | 65 |
| H31 | H chain CDR2 | 66 |
| L1 | L chain CDR1 | 67 |
| L2 | L chain CDR1 | 68 |
| L12 | L chain CDR2 | 69 |
| L20 | L chain CDR1, CDR2 | 67, 69 |
| L21 | L chain CDR1, FR4 | 67, 70 |
| L23 | L chain CDR2 | 71 |

TABLE 10

| Name of altered antibody | IC50 concentration |
|---|---|
| H3-G1d/LB-k | 118 |
| H5-G1d/LB-k | 95 |
| H6-G1d/LB-k | 108 |
| H7-G1d/LB-k | 93 |
| H8-G1d/LB-k | 105 |
| H9-G1d/LB-k | 99 |
| H10-G1d/LB-k | 96 |
| H31-G1d/LB-k | 118 |
| HY-G1d/L1-k | 98 |
| HY-G1d/L2-k | 102 |

TABLE 10-continued

| Name of altered antibody | IC50 concentration |
|---|---|
| HY-G1d/L12-k | 101 |
| HY-G1d/L20-k | 91 |
| HY-G1d/L21-k | 98 |
| HY-G1d/L23-k | 75 |

(IC50 concentration: IC50 concentration of each antibody if the IC50 concentration of the chimeric antibody EP27 (cH-G1/cL-k) is set to be 100)

(IC50 concentration: IC50 concentration of each antibody if the IC50 concentration of the chimeric antibody EP27 (cH-G1/cL-5) is set to be 100)

Example 4

Introduction of Mutations that Reduce the Amount of Aggregate

Controlling the amount of aggregate in protein pharmaceuticals is very important in consideration of quality control and influences on efficacy and immunogenicity (Curr. Opin. Biotechnol. (2009) 20 (6), 708-714). In general, aggregation is influenced by both colloidal stability due to the protein solution environment and conformational stability due to the protein structure (J. Pharm. Sci. (2010) 100 (4), 1306-1315). According to investigations on formulations of antibody preparations, it is possible to obtain desirable conditions that are effective for colloidal stability by screening antibody concentration, pH, buffer type, ionic strength, additive and such. On the other hand, conformational stability partially depends on amino acid sequences; and thus, in the case of antibodies, it is considered important to maintain the characteristic structures such as the CDR canonical structure, FR consensus sequence, and VH/VL interface (Jung et al., J. Mol. Biol. (2001) 309 (3), 701-716; Xiang et al., J. Mol. Biol. (1995) 253 (3), 385-390; Ewert et al., Methods. (2004) 34 (2), 184-199; Vargas-Madrazo et al., J. Mol. Recognit. (2003) 16 (3), 113-120; Morea et al., J. Mol. Biol. (1998) 275, 269-294; Vargas-Madrazo et al., J. Mol. Recognit. (2003) 16 (3), 113-120).

From the above viewpoints, in the present invention, the design was carried out in an effort to prepare humanized antibodies that are structurally more stable. As a result, the humanized EP27 antibody HY-G1d/LB-k was found. To further reduce the amount of aggregates contained in HY-G1d/LB-k, hydrophobic residues contained in the CDR of HY-G1d/LB-k were substituted with hydrophilic residues, and the inhibitory effect on aggregation by attenuating the hydrophobic interactions between molecules was examined.

Specifically, H25-G1d (SEQ ID NO: 92), H41-G1d (SEQ ID NO: 93), H42-G1d (SEQ ID NO: 94), H43-G1d (SEQ ID NO: 95), H44-G1d (SEQ ID NO: 96), and H45-G1d (SEQ ID NO: 97) were designed as H-chain genes in which any one of the CDR sequences (SEQ ID NOs: 86 to 91) shown in Table 11 has been introduced into the humanized EP27 antibody HY-G1d/LB-k (H chain HY-G1d/SEQ ID NO: 38; L chain LB-k/SEQ ID NO: 29). Using the technique of Example 1, an H-chain gene vector with substituted residues was co-expressed with the LB-k vector to obtain humanized EP27 antibodies, H25-G1d/LB-k, H41-G1d/LB-k, H42-G1d/L13-k, H43-G1d/LB-k, H44-G1d/LB-k, and H45-G1d/LB-k. The quantity of aggregates contained in the humanized EP27 antibodies was determined by gel filtration chromatography (Reference Example 9), and the result is shown in Table 12. By this, humanized EP27 antibody sequences with a significantly reduced amount of aggregates as compared with the chimeric antibody EP27 (cH-G1d/cL-k) were found.

TABLE 11

| CDR variant name | Altered CDR | SEQ ID NO |
|---|---|---|
| H25 | H chain CDR2 | 86 |
| H41 | H chain CDR2 | 87 |
| H42 | H chain CDR2 | 88 |
| H43 | H chain CDR2 | 89 |
| H44 | H chain CDR2 | 90 |
| H45 | H chain CDR2 | 91 |

TABLE 12

| Name of altered antibody | Aggregate (%) | SEQ ID NO (H chain) | SEQ ID NO (L chain) |
|---|---|---|---|
| cH-G1d/cL-k | 15.6 | 32 | 33 |
| HY-G1d/LB-k | 5.1 | 38 | 29 |
| H25-G1d/LB-k | 2.0 | 92 | 29 |
| H41-G1d/LB-k | 1.4 | 93 | 29 |
| H42-G1d/LB-k | 1.5 | 94 | 29 |
| H43-G1d/LB-k | 2.1 | 95 | 29 |
| H44-G1d/LB-k | 1.6 | 96 | 29 |
| H45-G1d/LB-k | 2.0 | 97 | 29 |

The ability of the obtained antibodies to bind to human epiregulin was evaluated as inhibition of epiregulin binding (Reference Example 5) to the chimeric antibody EP27. As shown in Table 13, the antigen-binding abilities of the humanized EP27 antibodies were equivalent to that of the chimeric antibody EP27. From the above investigation, humanized EP27 antibody sequences with a reduced amount of aggregates and an antigen-binding ability equivalent to that of the chimeric antibody EP27 were found.

TABLE 13

| Name of altered antibody | IC50 concentration |
|---|---|
| H25-G1d/LB-k | 108 |
| H41-G1d/LB-k | 106 |
| H42-G1d/LB-k | 96 |
| H43-G1d/LB-k | 108 |
| H44-G1d/LB-k | 94 |
| H45-G1d/LB-k | 92 |

(IC50 concentration: IC50 concentration of each antibody if the IC50 concentration of the chimeric antibody EP27 (cH-G1/cL-k) is set to be 100)

In addition, the following antibodies which were designed as humanized EP27 antibodies by arbitrarily combining sequences comprising the amino acid residue substitutions found in Examples 1 to 4 were prepared using the method of Example 1:

H87-G1d/LB-k (H chain: SEQ ID NO: 98; L chain: SEQ ID NO: 29),

H87-G1d/L21-k (H chain: SEQ ID NO: 98; L chain: SEQ ID NO: 84),

H87-G1d/L37-k (H chain: SEQ ID NO: 98; L chain: SEQ ID NO: 99).

Their ability to bind to human epiregulin was evaluated as inhibition of epiregulin binding to the chimeric antibody EP27 (Reference Example 5). As a result, as shown in Table 14, all the antibodies had a binding ability equivalent to that of the chimeric antibody EP27 (cH-G1/cL-k). Also, the quantity of aggregates contained in the humanized EP27 antibodies was measured by gel filtration chromatography (Reference Example 9), the thermal denaturation intermediate temperature (Tm) of Fab was measured with a differential scanning calorimeter (Reference Example 10), and the isoelectric point (pI) was measured by isoelectric focusing (Reference Example 11). As shown in Table 14, it was confirmed that the quantities of aggregates were significantly decreased and the Tm values were increased, in comparison with the chimeric antibody EP27 (cH-G1d/cL-k). Thus, humanized EP27 antibody sequences that achieve reduced immunogenicity risks, suppressed chemical degradation, lowered isoelectric points, and reduced quantity of aggregates by humanization as shown in Examples 1 to 4 were found.

TABLE 14

| Antibody name | IC50 concentration | Aggregate (%) | Tm (° C.) | pI |
|---|---|---|---|---|
| cH-G1/cL-k | 100 | 15.6 | <70 | 9.1 |
| H87-G1d/LB-k | 119 | 1.3 | 76.5 | 8.9 |
| H87-G1d/L21-k | 82 | 1.3 | 74.6 | 7.9 |
| H87-G1d/L37-k | 71 | 1.2 | 74.4 | 8.5 |

(IC50 concentration: IC50 concentration of each antibody if the IC50 concentration of the chimeric antibody EP27 (cH-G1/cL-k) is set to be 100)

Example 5

Introduction of Mutations that Improve the Ability to Bind to Monkey Antigen and Reduce Immunogenicity During drug development, in general, toxicity and safety evaluations in preclinical studies are considered to be important for dosage determination and various risk assessments in clinical studies. In the case of antibody pharmaceuticals, their antigen binding specificity could limit the selection of animal species used for preclinical studies. In many cases, primates which are genetically close to human are selected. However, evaluation using primates is sometimes not judged to be appropriate if the antibody of interest does not bind to a primate antigen, or if the binding ability is significantly different from its ability to bind to a human antigen. To cope with such cases, attempts are made to evaluate toxicity and safety in preclinical studies by using a surrogate antibody that binds to an antigen of the animal species to be used, or utilizing human antigen transgenic animals (Chapman et al., Nat. Rev. Drug Discov. (2007) 6, 120-126).

Substitutions of amino acid residues by methods known to those skilled in the art, e.g., affinity maturation using phage library or ribosome display, are thought to be effective for altering the antigen-binding ability of an antibody of interest. In addition, based on the three-dimensional structures of antigens and antibody variable region binding sites, computational science techniques can be used to improve species cross-reactivity (Farady et al., Bioorganic & Medicinal Chemistry Letters 19 (2009) 3744-3747). However, no report has been published on alteration of the antigen-binding ability of an anti-human epiregulin antibody without large-scale screening or computational science techniques. In addition, no structural difference has been revealed between monkey epiregulin and human epiregulin, and thus, no guidance has been shown as to which amino acid residues of an anti-human epiregulin antibody should be modified to enhance its binding activity to monkey epiregulin. In the present invention, multiple antibody sequences were designed by substituting amino acid residues at arbitrary sites of the CDR. Using the technique of Example 1, antibody genes with these residues substituted were prepared, and the antibodies were expressed. Specifically, sequences in which substitution with an Arg residue is made in the H-chain CDR2 and CDR3 and L-chain CDR3 shown in Table 15 were designed, and the antibodies shown in Table 16 were prepared. Affinities for human and monkey epiregulin were evaluated utilizing a device (BIACORE) using surface plasmon scattering (Reference Example 6).

Figure 2:
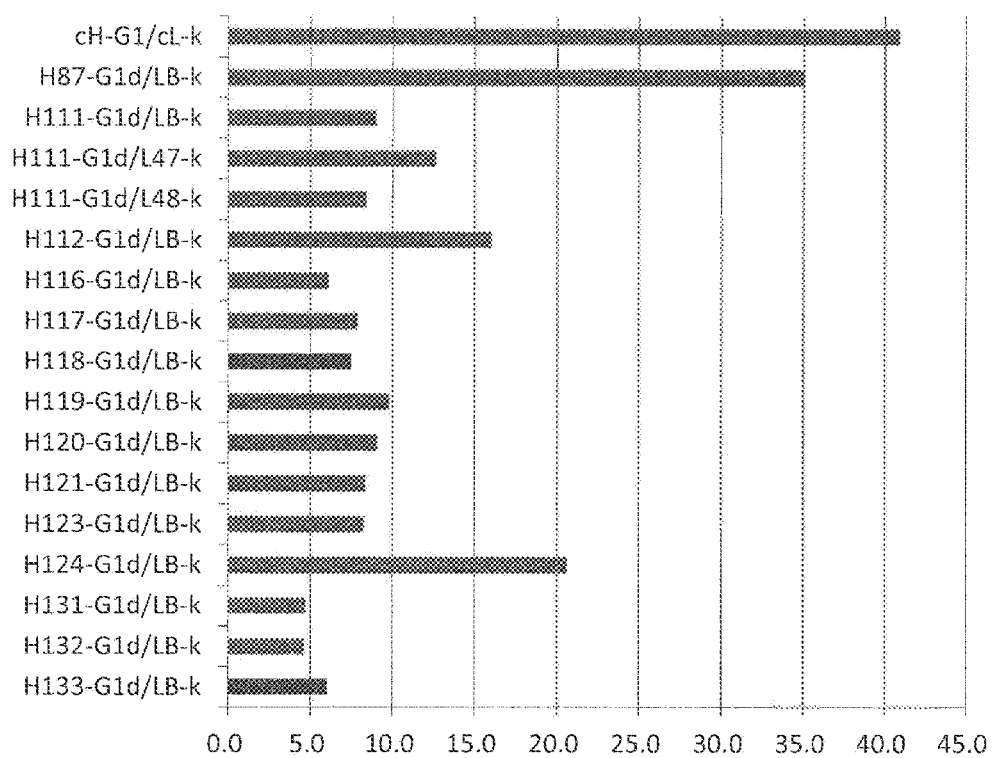
FIG. 2 depicts a graph showing the affinity ratio of each of the antibodies (KD value for monkey Epiregulin/KD value for human Epiregulin). While notation of the antibody name is described by the name of the variable region only, the figure depicts test results of antibodies containing the G1d heavy-chain and the kappa light-chain constant regions.

As a result, in comparison with the chimeric EP27 antibody, humanized EP27 antibody sequences with no reduced affinity for human epiregulin, enhanced affinity for monkey epiregulin, and low affinity ratio (=KD value for monkey epiregulin/KD value for human epiregulin) which is an indicator that shows cross-reactivity for monkey epiregulin and human epiregulin were found (FIGS. 1 and 2).

TABLE 15

| CDR variant name | Altered CDR | SEQ ID NO |
|---|---|---|
| H111 | H chain CDR2 | 100 |
| H112 | H chain CDR2 | 101 |
| H116 | H chain CDR2 | 102 |
| H117 | H chain CDR2 | 103 |
| H118 | H chain CDR2 | 104 |
| H119 | H chain CDR2 | 105 |
| H120 | H chain CDR2 | 106 |
| H121 | H chain CDR2 | 107 |
| H123 | H chain CDR2 | 108 |
| H124 | H chain CDR1 | 109 |
| H131 | H chain CDR3 | 110 |
| H132 | H chain CDR3 | 111 |
| H133 | H chain CDR3 | 112 |
| L47 | L chain CDR3 | 113 |
| L48 | L chain CDR3 | 114 |

TABLE 16

| CDR variant name | SEQ ID NO (H chain) | SEQ ID NO (L chain) | cEREG KD (nM)/ hEREG KD (nM) |
|---|---|---|---|
| cH-G1/cL-k | 32 | 33 | 40.9 |
| H87-G1d/LB-k | 98 | 29 | 35.1 |
| H111-G1d/LB-k | 115 | 29 | 9.0 |
| H111-G1d/L47-k | 115 | 128 | 12.6 |
| H111-G1d/L48-k | 115 | 129 | 8.4 |
| H112-G1d/LB-k | 116 | 29 | 16.0 |
| H116-G1d/LB-k | 117 | 29 | 6.1 |
| H117-G1d/LB-k | 118 | 29 | 7.9 |
| H118-G1d/LB-k | 119 | 29 | 7.5 |
| H119-G1d/LB-k | 120 | 29 | 9.8 |
| H120-G1d/LB-k | 121 | 29 | 9.1 |
| H121-G1d/LB-k | 122 | 29 | 8.3 |
| H123-G1d/LB-k | 123 | 29 | 8.2 |
| H124-G1d/LB-k | 124 | 29 | 20.6 |
| H131-G1d/LB-k | 125 | 29 | 4.7 |
| H132-G1d/LB-k | 126 | 29 | 4.6 |
| H133-G1d/LB-k | 127 | 29 | 6.1 |

In the development of medical pharmaceuticals, the emergence of antibodies against a drug after its administration poses problems on efficacy and safety. Thus, it is important to reduce the immunogenicity of a drug of interest. In vivo, in vitro, and in silico techniques are available for predicting the immunogenicity of biologics, and reports have been published on the correlation with incidence of anti-drug antibodies in clinical practice (Baker et al., Curr. Drug Saf. (2010) 5 (4), 308-313; Bryson et al., BioDrugs. (2010) 24 (1), 1-8; Groot et al., Curr. Opin. Pharmacol. (2008) 8 (5), 620-626). In the present invention, humanized EP27 antibody sequences that reduce immunogenicity risks without impairing the antigen binding ability of an antibody of interest can be predicted by predicting T-cell epitopes using the technique described in Reference Example 13.

Figure 3:
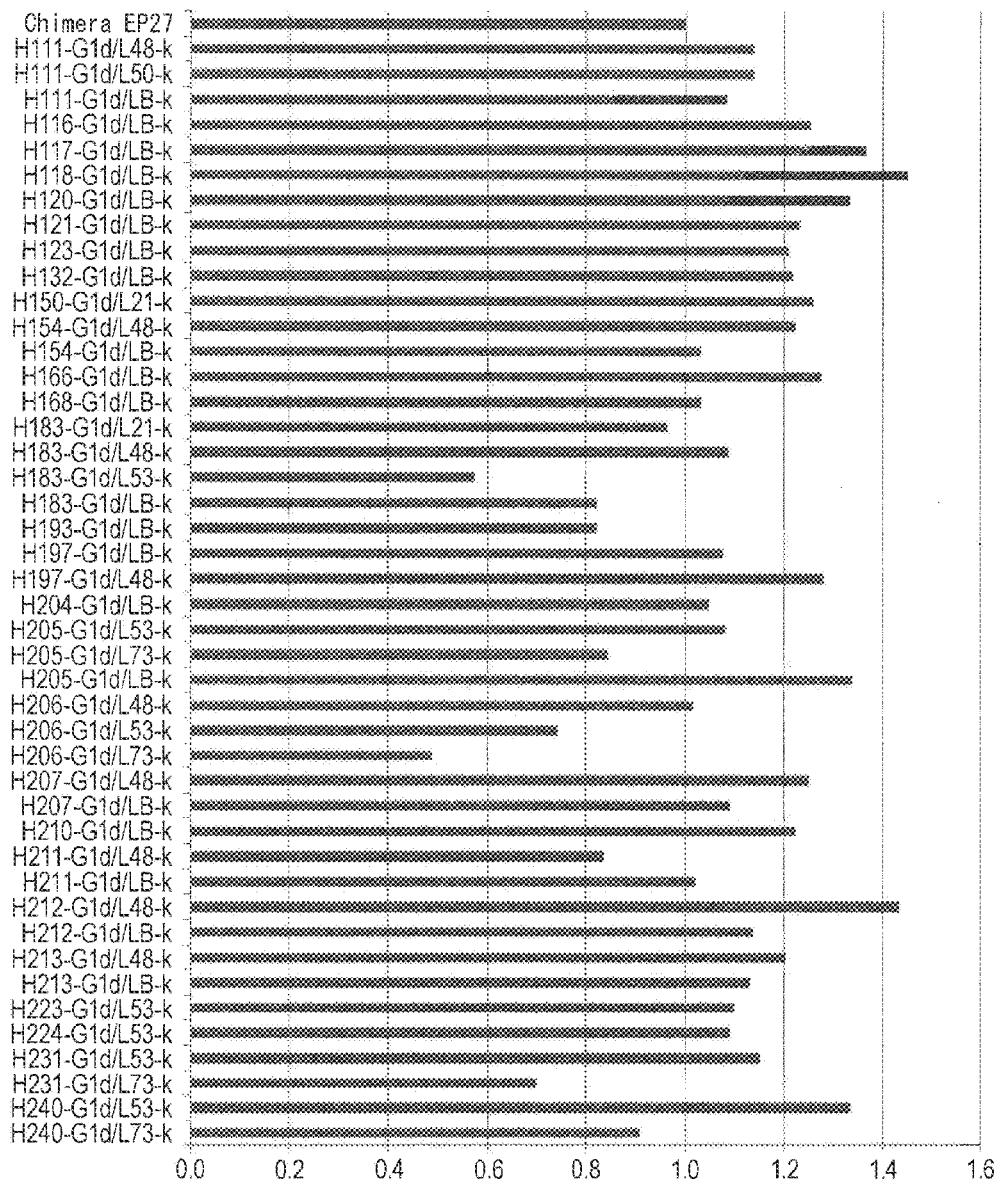
FIG. 3 depicts a graph showing the affinity ratio of each of the antibodies to human Epiregulin (KD value of each antibody/KD value of the chimeric antibody EP27).
Figure 4:
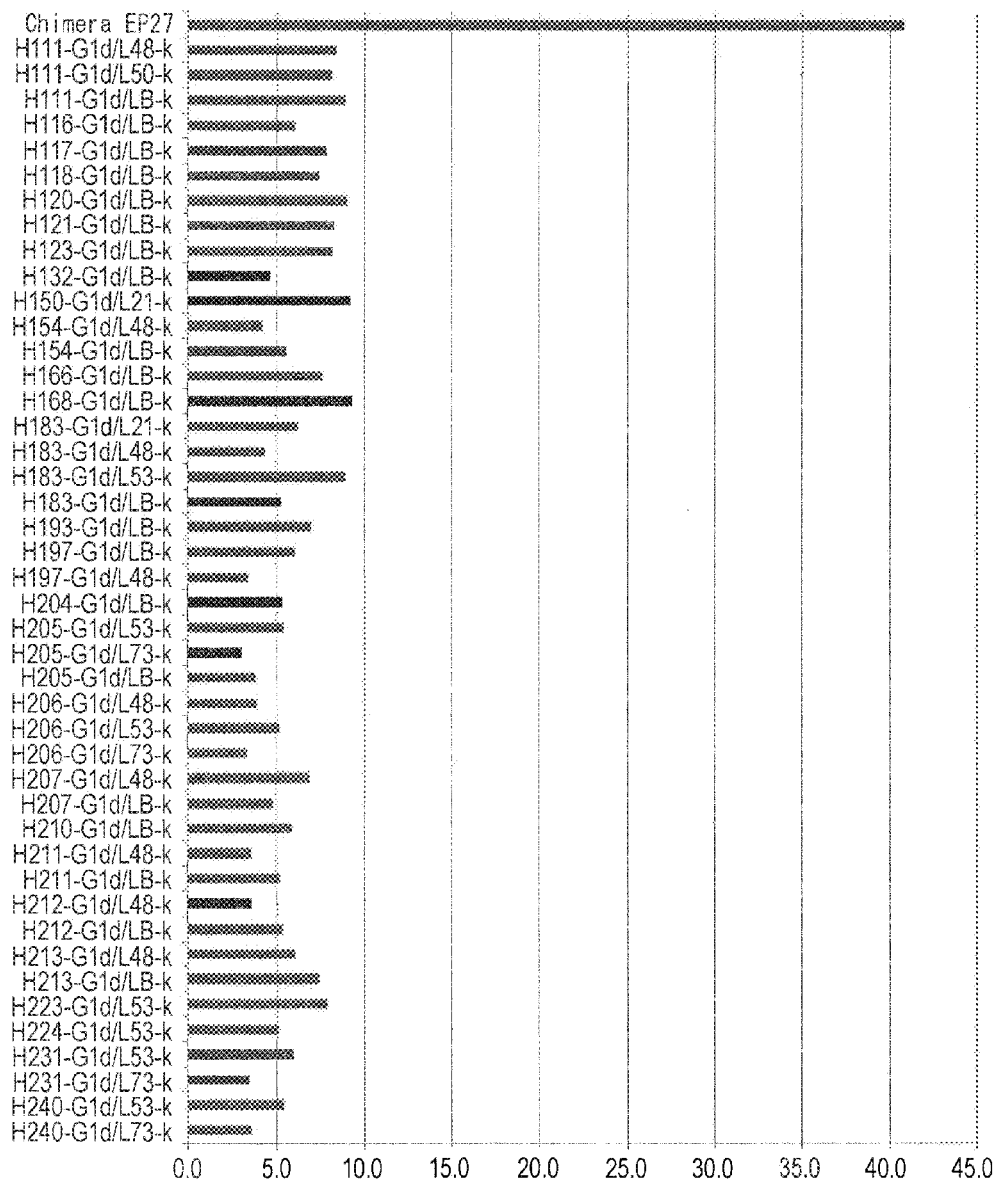
FIG. 4 depicts a graph showing the affinity ratio of each of the antibodies (KD value for monkey Epiregulin/KD value for human Epiregulin).

For the sequences comprising alterations found in Examples 1 to 4, sequences with an arbitrary combination of mutations that improve the affinity for monkey epiregulin and/or reduce immunogenicity were designed. The humanized EP27 antibodies thus designed and listed in Table 17 (SEQ ID NOs: 115 to 150) were prepared using the method of Example 1. Mutated CDR sequences of the humanized EP27 antibodies listed in Table 17 are shown in Table 18. Affinities for human and monkey epiregulin were evaluated utilizing a device (BIACORE) using surface plasmon scattering (Reference Example 6). As shown in FIG. 3, the affinity of each of the humanized EP27 antibodies for human epiregulin was equivalent to the affinity of the chimeric antibody EP27 (cH-G1/cL-k). Affinity ratios (=KD value for monkey epiregulin/KD value for human epiregulin) were compared as an indicator of the difference in the affinities for monkey and human antigens. It was confirmed that the difference in the affinities of each humanized EP27 antibody for the two antigens was significantly reduced as compared with that of the chimeric antibody (FIG. 4). Thus, humanized EP27 antibody sequences that have an improved affinity for monkey epiregulin without reducing the affinity for human epiregulin were found.

TABLE 17

| Antibody name | SEQ ID NO (H chain) | SEQ ID NO (L chain) |
| --- | --- | --- |
| H111-G1d/L48-k | 115 | 129 |
| H111-G1d/L50-k | 115 | 130 |
| H111-G1d/LB-k | 115 | 29 |
| H116-G1d/LB-k | 117 | 29 |
| H117-G1d/LB-k | 118 | 29 |
| H118-G1d/LB-k | 119 | 29 |
| H120-G1d/LB-k | 121 | 29 |
| H121-G1d/LB-k | 122 | 29 |
| H123-G1d/LB-k | 123 | 29 |
| H132-G1d/LB-k | 126 | 29 |
| H150-G1d/L21-k | 131 | 84 |
| H154-G1d/L48-k | 132 | 129 |
| H154-G1d/LB-k | 132 | 29 |
| H166-G1d/LB-k | 133 | 29 |
| H168-G1d/LB-k | 134 | 29 |
| H183-G1d/L21-k | 135 | 84 |
| H183-G1d/L48-k | 135 | 129 |
| H183-G1d/L53-k | 135 | 136 |
| H183-G1d/LB-k | 135 | 29 |
| H193-G1d/LB-k | 137 | 29 |
| H197-G1d/LB-k | 138 | 29 |
| H197-G1d/L48-k | 138 | 129 |
| H204-G1d/LB-k | 139 | 29 |
| H205-G1d/L53-k | 140 | 136 |
| H205-G1d/L73-k | 140 | 141 |
| H205-G1d/LB-k | 140 | 29 |
| H206-G1d/L48-k | 142 | 129 |
| H206-G1d/L53-k | 142 | 136 |
| H206-G1d/L73-k | 142 | 141 |
| H207-G1d/L48-k | 143 | 129 |

TABLE 17-continued

| Antibody name | SEQ ID NO (H chain) | SEQ ID NO (L chain) |
| --- | --- | --- |
| H207-G1d/LB-k | 143 | 29 |
| H210-G1d/LB-k | 144 | 29 |
| H211-G1d/L48-k | 145 | 129 |
| H211-G1d/LB-k | 145 | 29 |
| H212-G1d/L48-k | 146 | 129 |
| H212-G1d/LB-k | 146 | 29 |
| H213-G1d/L48-k | 147 | 129 |
| H213-G1d/LB-k | 147 | 29 |
| H213-G1d/L53-k | 147 | 136 |
| H224-G1d/L53-k | 148 | 136 |
| H231-G1d/L53-k | 149 | 136 |
| H231-G1d/L73-k | 149 | 141 |
| H240-G1d/L53-k | 150 | 136 |
| H240-G1d/L73-k | 150 | 141 |

TABLE 18

| CDR variant name | Altered CDR | SEQ ID NO |
| --- | --- | --- |
| H150 | H chain CDR3 | 151 |
| H154 | H chain CDR3 | 152 |
| H166 | H chain CDR2, 3 | 153, 154 |
| H168 | H chain CDR2, 3 | 155, 154 |
| H183 | H chain CDR2, 3 | 153, 152 |
| H193 | H chain CDR2, 3 | 156, 151 |
| H197 | H chain CDR2, 3 | 157, 151 |
| H204 | H chain CDR2, 3 | 153, 152 |
| H205 | H chain CDR2, 3 | 153, 158 |
| H206 | H chain CDR2, 3 | 153, 152 |
| H207 | H chain CDR2, 3 | 153, 152 |
| H210 | H chain CDR2, 3 | 159, 152 |
| H211 | H chain CDR2, 3 | 157, 152 |
| H212 | H chain CDR2, 3 | 160, 152 |
| H213 | H chain CDR2, 3 | 161, 152 |
| H224 | H chain CDR2, 3 | 153, 158 |
| H231 | H chain CDR2, 3 | 153, 158 |
| H240 | H chain CDR2, 3 | 160, 158 |
| L50 | L chain FR1 | 162 |
| L53 | L chain CDR1 | 163 |
| L73 | L chain CDR1, 3 | 163, 164 |

In addition, the amount of aggregate contained in the humanized EP27 antibodies was measured by gel filtration chromatography (Reference Example 9), and the thermal denaturation intermediate temperature (Tm) of the Fabs prepared from the humanized EP27 antibodies was measured by differential scanning calorimeter (Reference Example 10). As shown in Table 19, it was confirmed that the quantities of aggregates were significantly decreased, and the Tm values were increased, in comparison with the chimeric antibody EP27 (cH-G1d/cL-k). Thus, as shown in Examples 1 to 5, humanized EP27 antibody sequences comprising reduced immunogenicity risks, suppressed chemical degradation, lowered isoelectric points, reduced quantities of aggregates, and improved binding abilities to the monkey antigen as a result of humanization were found.

TABLE 19

| Antibody name | Aggregate (%) | Tm (° C.) | hEREG KD ratio | cEREG KD ratio | cEREG (nM)/ hEREG (nM) | Immunogenicity score |
| --- | --- | --- | --- | --- | --- | --- |
| cH-G1/cL-k | 18.9 | <70 | 1 | 1 | 40.9 | 800.2 |
| H87-G1d/LB-k | 1.0 | 76.2 | 0.74 | 0.99 | 35.1 | 589.4 |
| H205-G1d/L53-k | 1.0 | 74.3 | 1.08 | 0.23 | 5.5 | 516.1 |
| H206-G1d/L53-k | 1.7 | 72.9 | 0.82 | 0.11 | 5.2 | 606.8 |
| H231-G1d/L53-k | 2.2 | 73.3 | 1.15 | 0.27 | 6.0 | 541.7 |
| H240-G1d/L53-k | 1.3 | 74.7 | 1.34 | 0.28 | 5.4 | 515.6 |
| H205-G1d/L73-k | 1.8 | 74.5 | 0.85 | 0.12 | 3.1 | 519.0 |
| H206-G1d/L73-k | 3.6 | 72.9 | 0.49 | 0.08 | 3.4 | 609.7 |

TABLE 19-continued

| Antibody name | Aggregate (%) | Tm (° C.) | hEREG KD ratio | cEREG KD ratio | cEREG (nM)/ hEREG (nM) | Immunogenicity score |
|---|---|---|---|---|---|---|
| H231-G1d/L73-k | 4.0 | 73.2 | 0.70 | 0.12 | 3.5 | 544.6 |
| H240-G1d/L73-k | 2.8 | 74.9 | 0.91 | 0.15 | 3.6 | 518.5 |

(KD ratio represents a relative ratio when the value for cH-G1/cL-k = 1.)

Example 7

Figure 5:
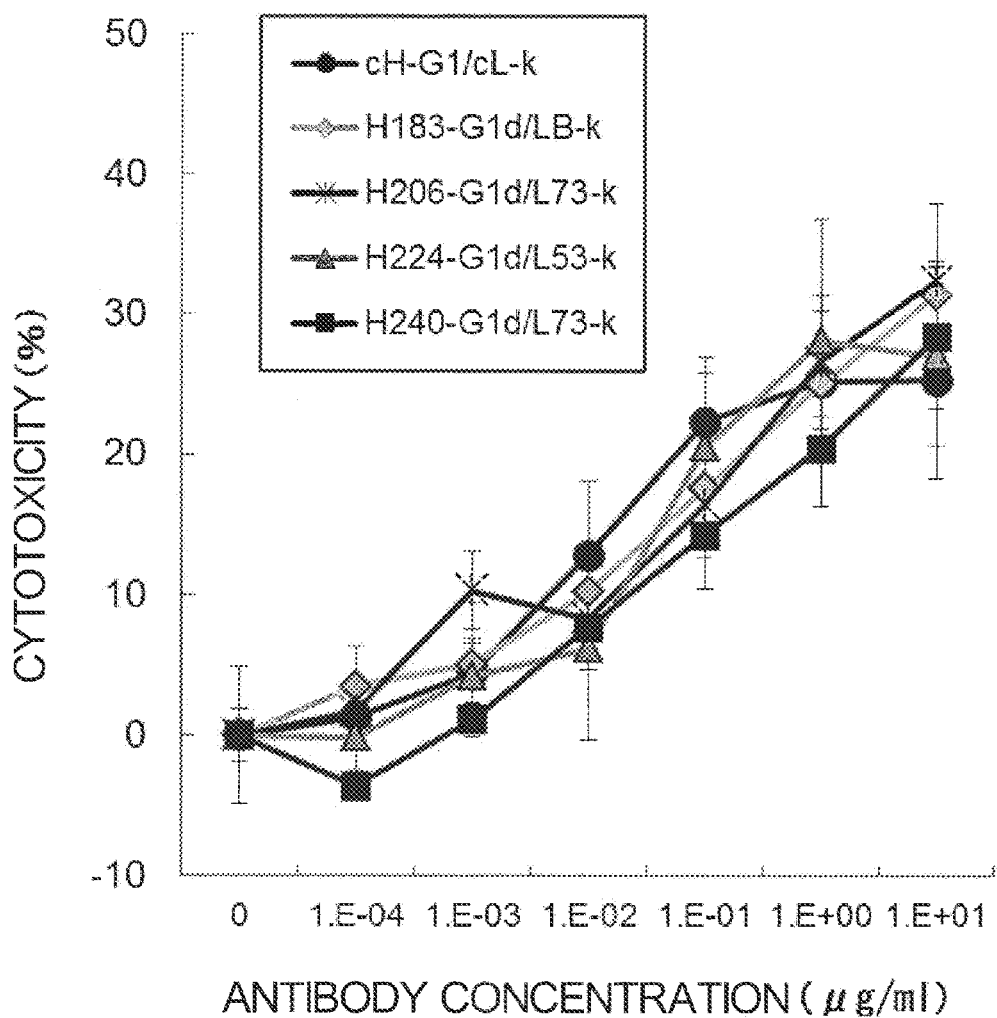
FIG. 5 depicts a graph showing the ADCC activity of each of the antibodies (specific calcein AM release rate).

ADCC Activity of Each Test Antibody Using Human Peripheral Blood Mononuclear Cells as Effector Cells Human peripheral blood mononuclear cells (hereinafter referred to as human PBMC) were used as effector cells to measure the ADCC activity of each test antibody as hereinbelow. A mononuclear cells fraction collected from human peripheral blood was used for the effector cell of human origin. As a result, all humanized EP27 antibodies used in the test were found to induce ADCC against MIA PaCa-2 cells (Reference Example 7) (FIG. 5).

Example 8

Figure 6:
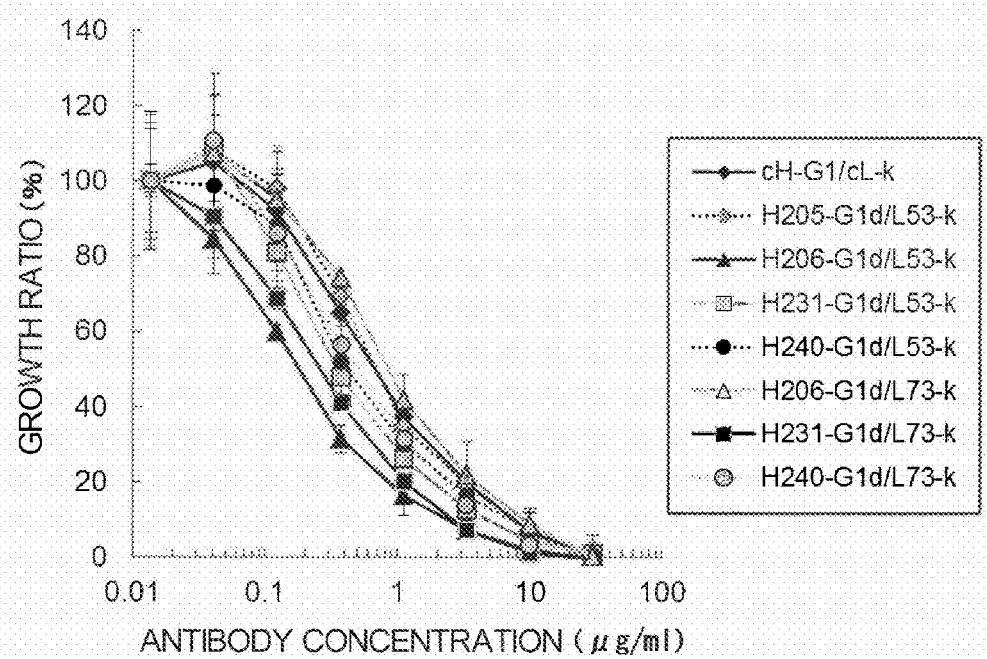
FIG. 6 depicts a graph showing the neutralizing activity of each of the antibodies in terms of the rate of inhibition of human Epiregulin-dependent BAF_EGFR cell proliferation.
Figure 7:
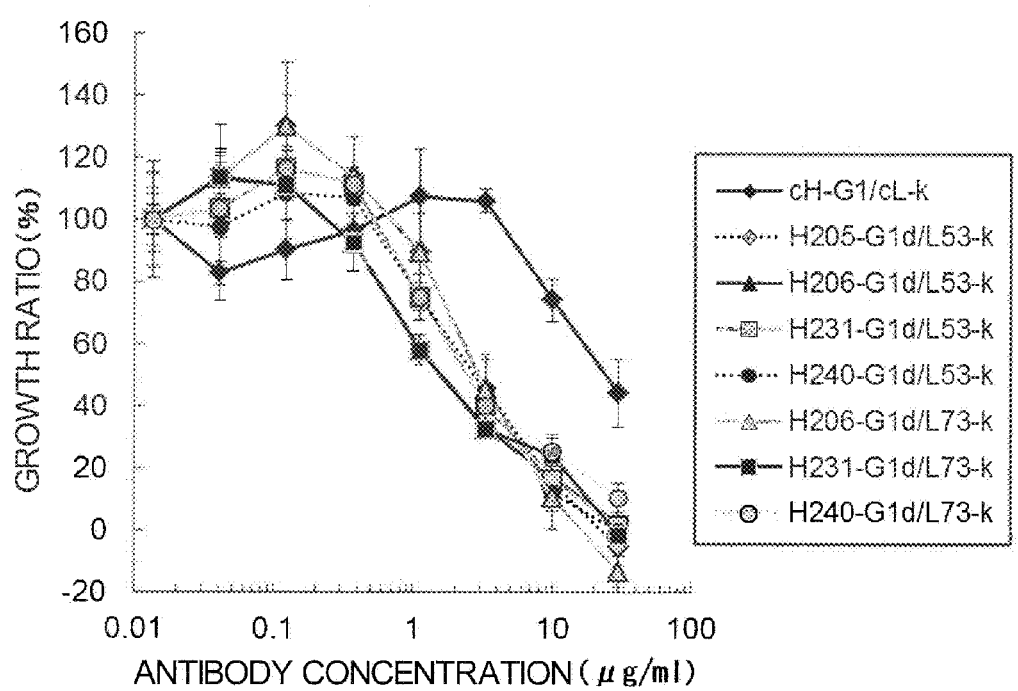
FIG. 7 depicts a graph showing the neutralizing activity of each of the antibodies in terms of the rate of inhibition of monkey Epiregulin-dependent BAF_EGFR cell proliferation.

Measurement of the Activity of Anti-Epiregulin Monoclonal Antibodies to Neutralize Cell Growth Stimulation by Human or Monkey Epiregulin Humanized EP27 antibody sequences with enhanced affinity to monkey Epiregulin were revealed in Example 5. To assess their activities in cells, the humanized EP27 antibodies were measured for their activities to neutralize cell growth stimulation by monkey Epiregulin and human Epiregulin. BAF_EGFR was used for the cells. All of the humanized EP27 antibodies evaluated this time were examined for their neutralizing activities which inhibit human and monkey Epiregulin-dependent EGFR_BAF cell growth (Reference Example 8), and all of the humanized EP27 antibodies showed enhanced neutralizing activities against monkey Epiregulin than the chimeric antibody (FIGS. 6 and 7).

Example 9

Drug Efficacy Test for the Humanized EP27 Antibodies Using an In Vivo Model

Figure 8:
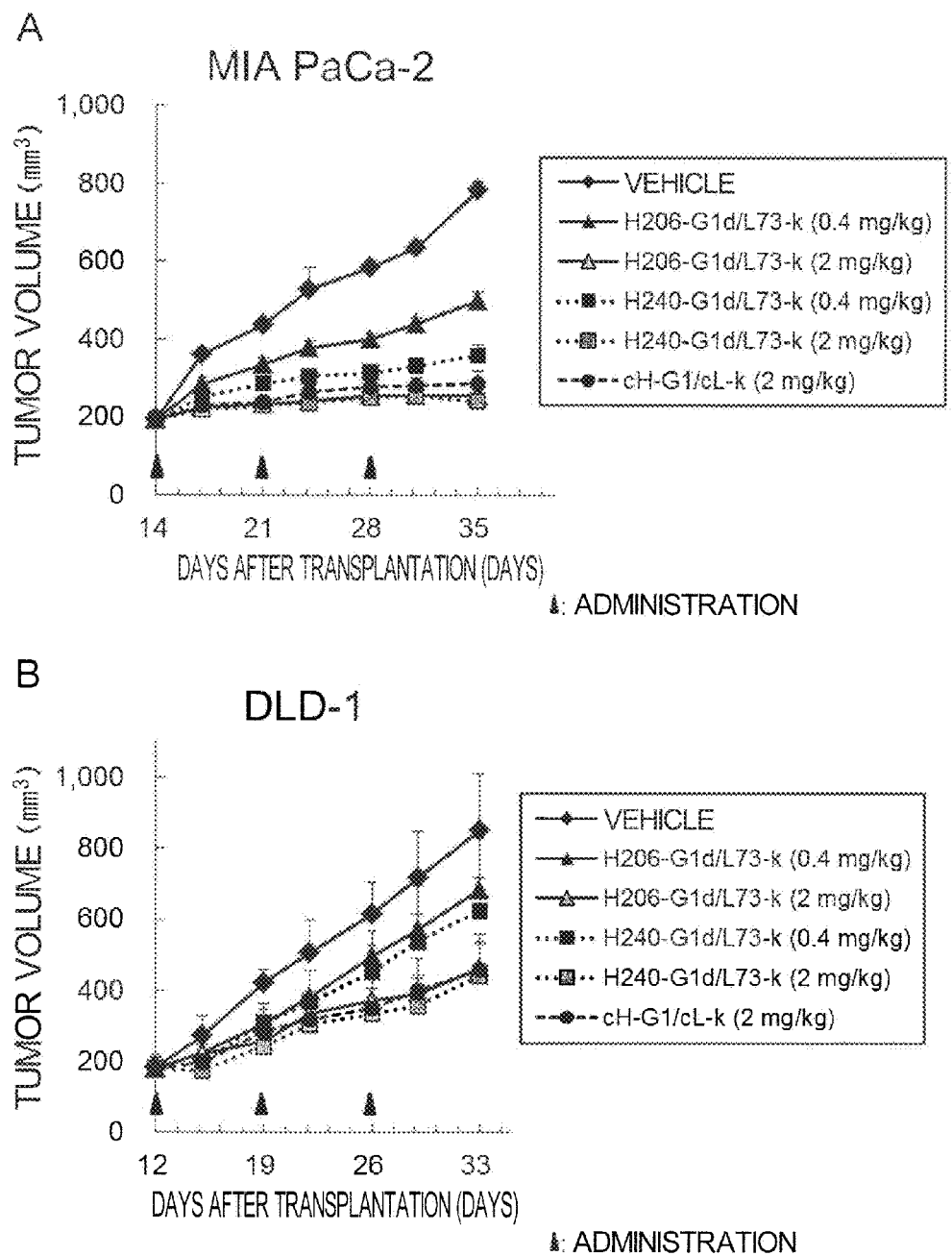
FIG. 8 depicts graphs showing the activity of each of the antibodies to suppress in vivo human tumor growth in terms of the antitumor activity in mouse models transplanted with human cancer cells.

The in vivo antitumor activity of the humanized EP27 antibodies, of which activity in in vitro cells had been confirmed in Examples 7 and 8, was evaluated using a human tumor-grafted mouse model (Reference Example 14). The anti-tumor effects of each test antibody evaluated in MIA PaCa-2 and DLD-1 human cancer cell-transplanted mouse models were evaluated by measuring the tumor volume on day 7 after the last day of sample administration. As a result, as shown in FIG. 8, when the cH-G1/cL-k antibody, H206-G1d/L73-k antibody, and H240-G1d/L73-k antibody were individually administered at both 0.4 mg/kg and 2 mg/kg, the excellent drug efficacy by the altered humanized EP27 antibodies was observed in the animal models as well.

Example 10

Immunohistochemical Staining Using an Anti-Epiregulin Antibody

Figure 10:
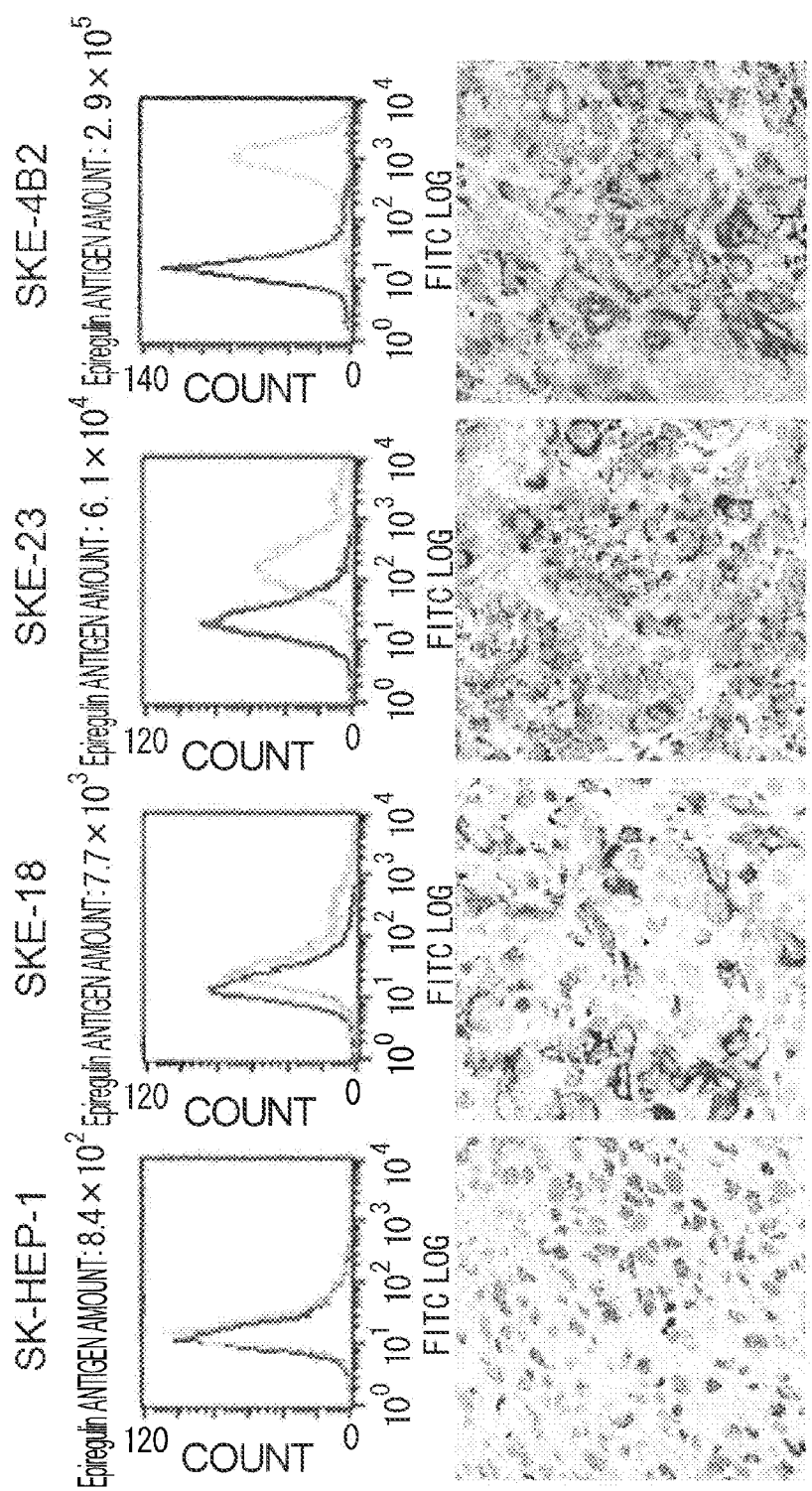
FIG. 10 shows the results of fluorescence staining of cells each expressing different amounts of the Epiregulin protein, and immunohistological staining of mice transplanted with these cells.
Figure 11:
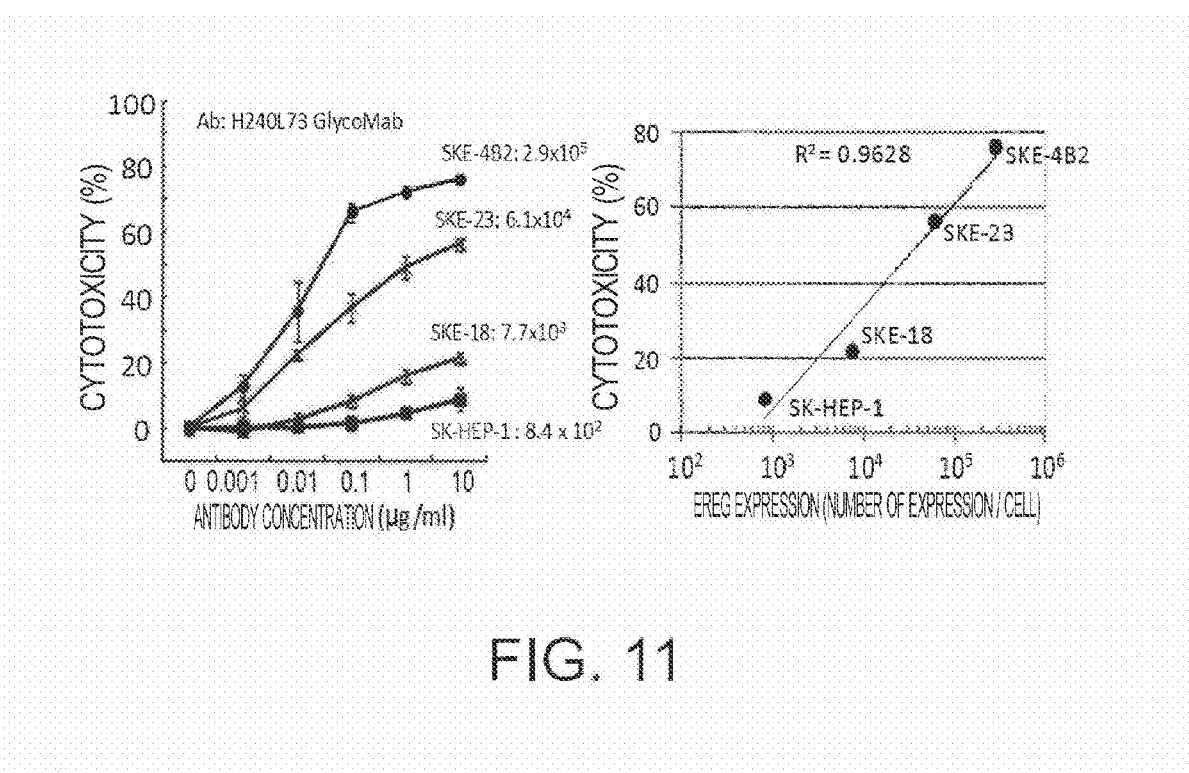
FIG. 11 depicts graphs showing the ADCC activity against cells each expressing different amounts of the Epiregulin protein.
Figure 12:
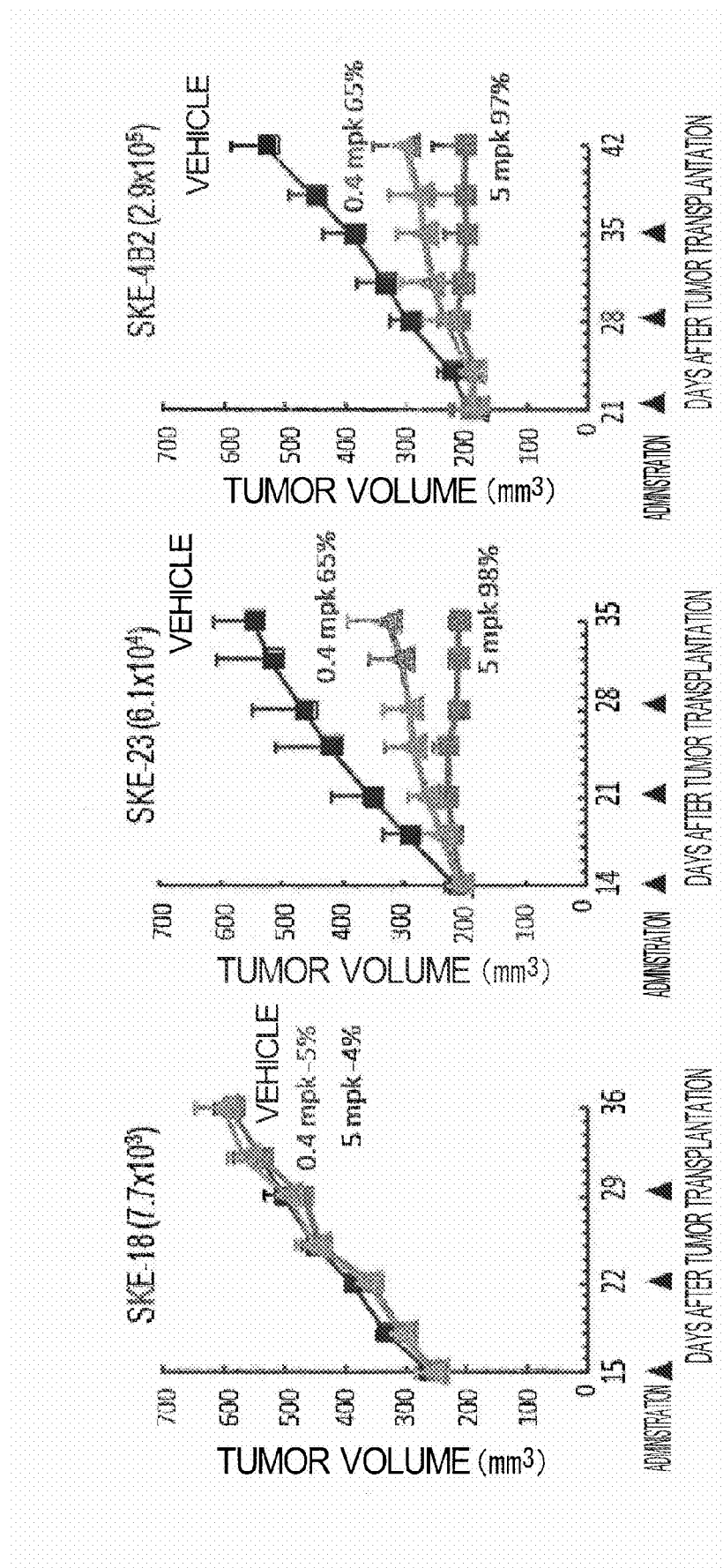
FIG. 12 depicts graphs showing the in vivo human tumor growth inhibition activity in terms of the antitumor activity in mouse models transplanted with cells each expressing different amounts of the Epiregulin protein.

An immunohistochemical staining method that reflects the antigen expression level was established using an EP27 antibody. Immunohistochemical staining was carried out using paraffin-embedded tissue blocks prepared with tissues of scid mice transplanted with cell lines that are forced to express EREG at different expression levels, which are SKE-18 (estimated amount of antigen was $7.7 \times 10^3$), SKE-23 (estimated amount of antigen was $6.1 \times 10^4$), and SKE-4B2 (estimated amount of antigen was $2.9 \times 10^5$), and the host cell SK-HEP-1 (amount of antigen was $8.4 \times 10^2$). The EREG expression in these thinly sliced tissue sections prepared from these paraffin blocks was visualized by incubation using an EP27 antibody as the primary antibody, followed by reacting a rabbit anti-mouse IgG polyclonal antibody (Jackson Immunoresearch Laboratories) as the secondary antibody, and a polymer-HRP (Dako cytomation)-bound goat anti-rabbit IgG antibody as the tertiary antibody, and using diaminobenzidine as substrate. As shown in FIG. 10, gradation of staining is observed in the stained cells/tissues depending on the amount of EREG expression. Furthermore, the in vitro ADCC activity of the H240-G1d/L73-k antibody was confirmed to depend on the expression level in these cells (FIG. 11). In the above-mentioned investigation, a low-fucose antibody was used for the H240-G1d/L73-k antibody. The low-fucose antibody was produced by the method described in WO2004/065540. Herein below, the low-fucose antibody is also referred to as the humanized EP27 antibody Glycomab. The in vitro ADCC activity of the H240-G1d/L73-k antibody (humanized EP27 antibody Glycomab) was confirmed in SKE-15 and SKE-10 which have an estimated antigen level of $2.8 \times 10^4$, in addition to in the above-mentioned four cell lines of forced EREG expression. In a similar manner to FIG. 11, the in vitro ADCC activity of the H240-G1d/L73-k antibody in accordance with the EREG expression level in these cells was confirmed (Table 20). Furthermore, the in vivo tumor growth inhibition activity of the H240-G1d/L73-k antibody (humanized EP27 antibody Glycomab) in accordance with the expression level in these cells was confirmed (FIG. 12). That is, assessment of the EREG expression level by immunohistochemical staining confirmed a correlation between the expression level and drug efficacy.

TABLE 20

| CLONE NAME | ANTIBODY CONCENTRATION (μg/mL) | ADCC (%) | EREG EXPRESSION LEVEL |
|---|---|---|---|
| SKE4B2 | 0.1 | 43.8 | 290000 |
| SKE23 | 0.1 | 32.6 | 61000 |
| SKE10 | 0.1 | 24.9 | 28000 |
| SKE15 | 0.1 | 17.4 | 28000 |
| SKE18 | 0.1 | 8.5 | 7700 |
| SKE1 | 0.1 | 4.4 | 5600 |
| SK-HEP1 | 0.1 | 9.1 | 840 |

Example 11

EREG Expression in Clinical Cases of Poorly Differentiated Colon Cancer

Figure 13:
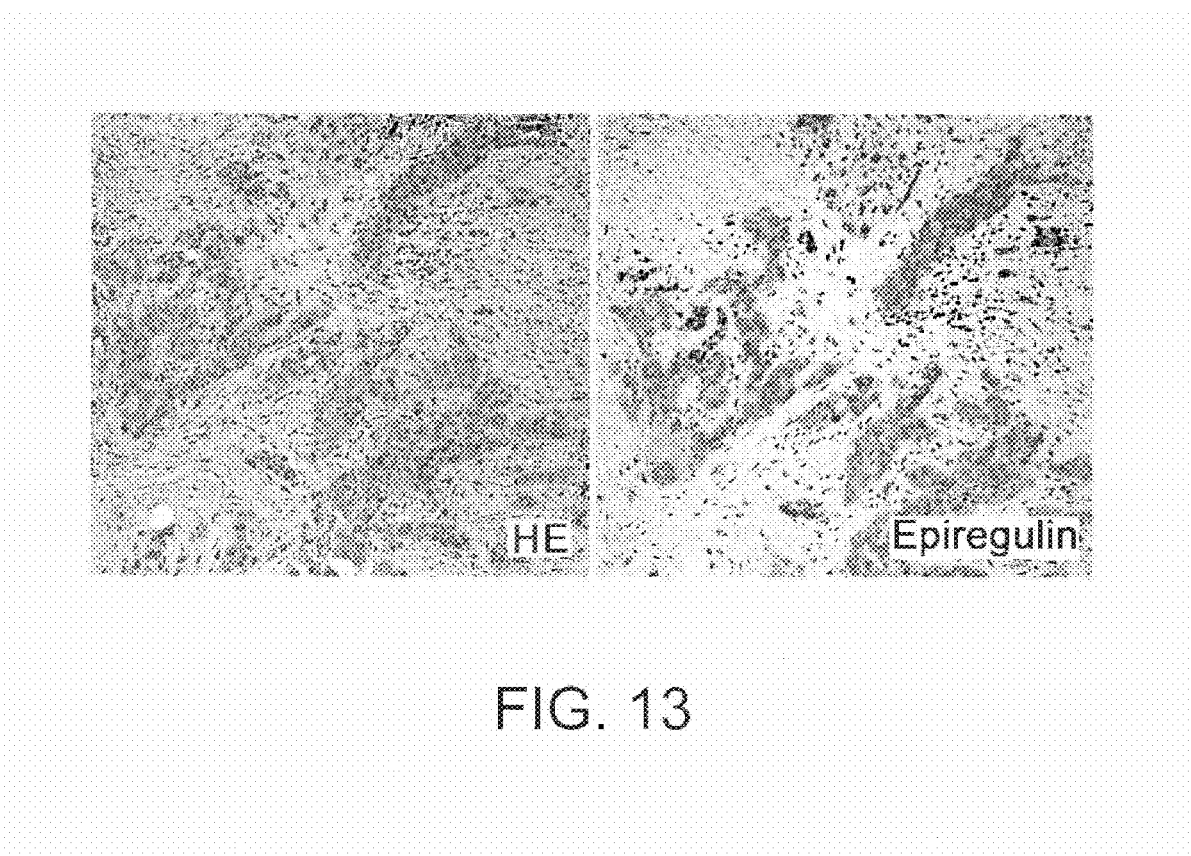
FIG. 13 presents photographs showing the Epiregulin expression in clinical cases of poorly-differentiated colon cancer.

To examine EREG expression in nine clinical cases of poorly differentiated colon cancer, thinly sliced paraffin-embedded specimens of the same cases were stained by the staining method described in Example 10. As a result, clearly positive images were confirmed in 7/9 cases (FIG. 13).

Example 12

Figure 14:
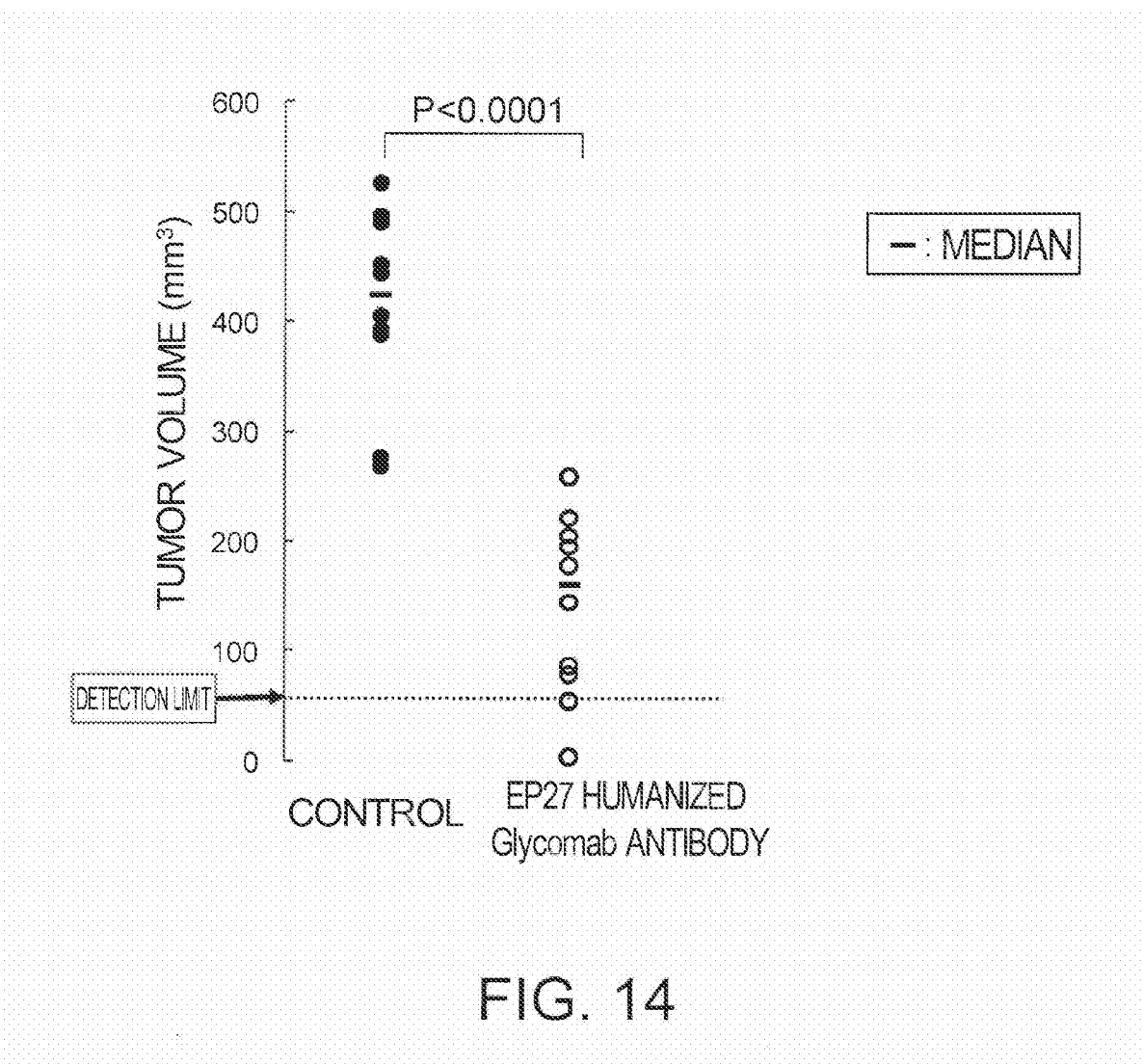
FIG. 14 is a diagram showing the drug efficacy of the humanized EP27 antibody Glycomab against tumorigenesis of PLR123 colon cancer stem cells, which shows drug efficacy against metastasis of colon cancer.

Drug Efficacy of the Humanized EP27 Antibody Glycomab Against Tumorigenesis of Colon Cancer Stems Cells Colon cancer stem cells ($1 \times 10^6$ cells) isolated from a human colon cancer tumor model PLR123 (WO02012/046797) were transplanted into the inguinal region of SCID mice. From the next day of administration of the stem cells to the SCID mice, the humanized EP27 antibody Glycomab was administered once a week at 10 mg/kg. As a result, the Wilcoxon's signed rank test (SAS system 8.02 TS level 02M0 and SAS preclinical package Version 5.00.010720) confirmed that on day 29 post-transplantation, the tumorigenicity was significantly suppressed in the antibody-administered group than in the control group as shown in FIG. 14.

Example 13

Figure 15:
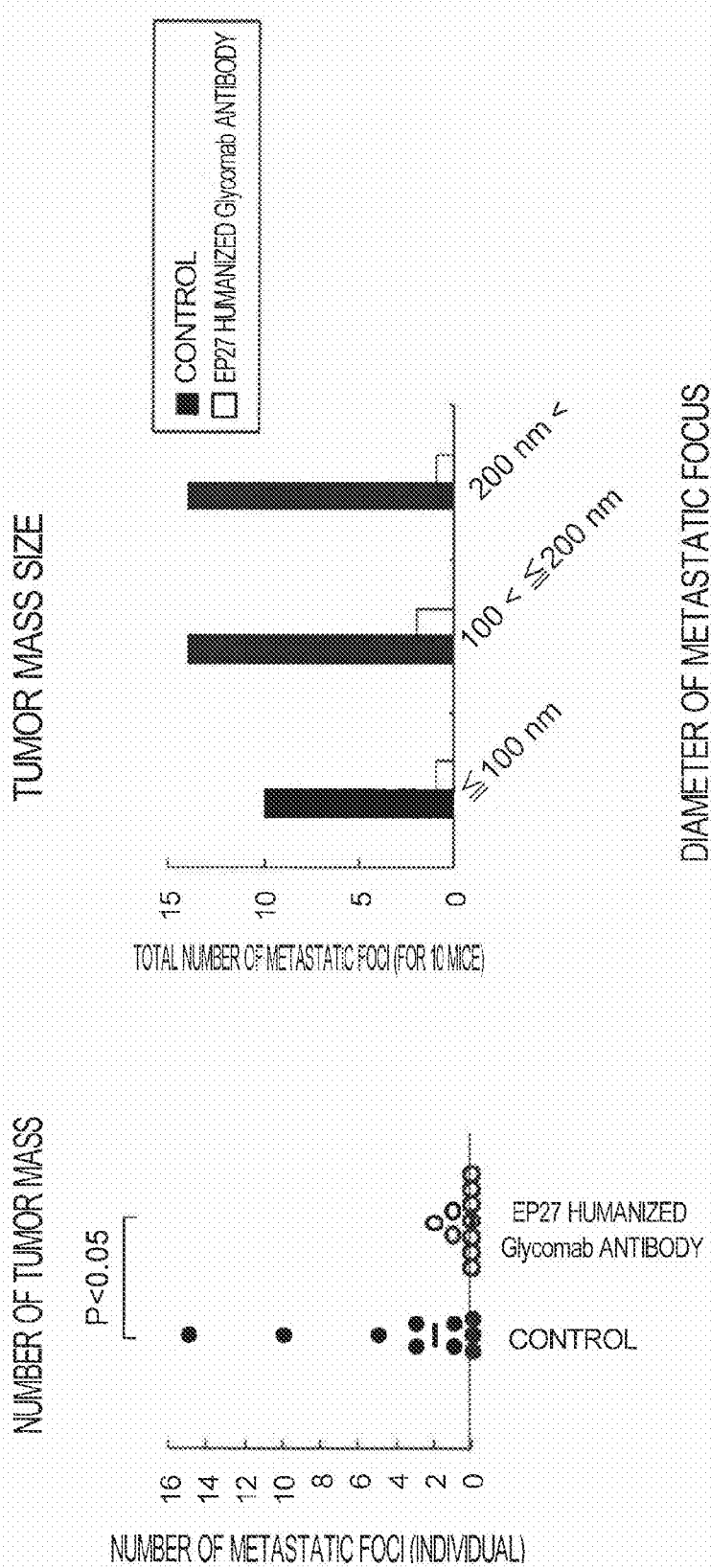
FIG. 15 shows the drug efficacy of the humanized EP27 antibody Glycomab against pulmonary metastasis of PLR123 colon cancer stem cells, which shows drug efficacy against metastasis of colon cancer stem cells.

Drug Efficacy of the Humanized EP27 Antibody Glycomab Against Metastasis of Colon Cancer Stem Cells Colon cancer stem cells ($2 \times 10^6$ cells) isolated from a human colon cancer tumor model PLR123 were transplanted into SCID-beige mice from the tail vein. Three days after administration of the stem cells to the mice, the humanized EP27 antibody Glycomab was administered once a week at 10 mg/kg. As a result, on day 52 post-transplantation, the number of tumor nodules in mouse lungs (number of metastatic lesions) and the size of the tumor nodule (diameter of the metastatic lesion) were confirmed to be significantly suppressed in the antibody-administered group than in the control group as shown in FIG. 15.

Example 14

Figure 16:
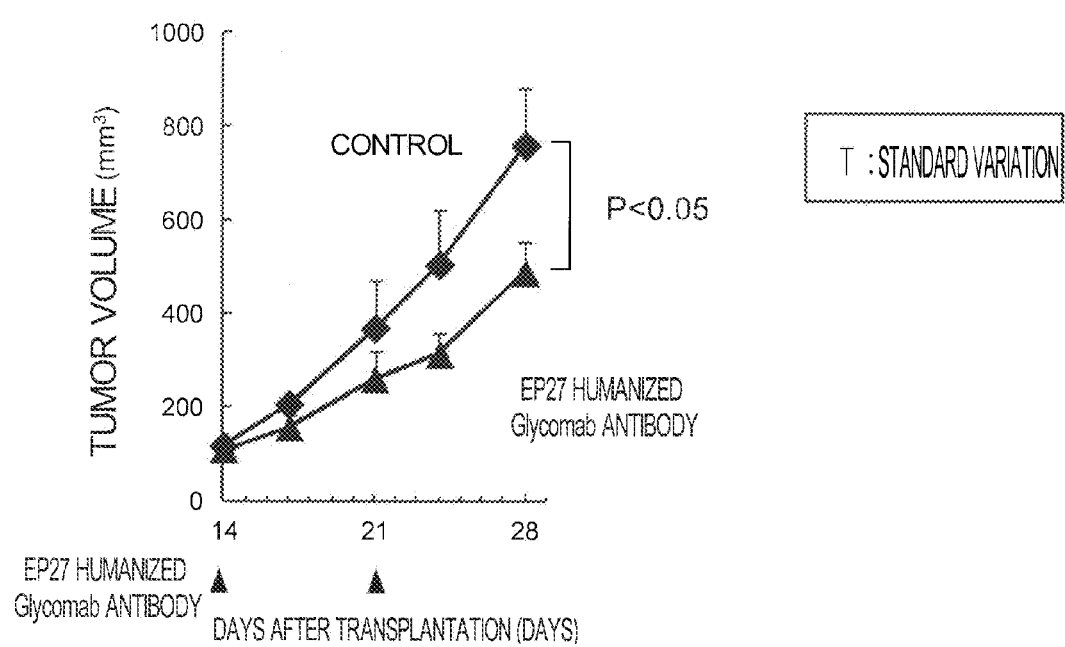
FIG. 16 is a graph showing the drug efficacy of the humanized EP27 antibody Glycomab against poorly-differentiated colon cancer using the poorly-differentiated colon cancer model COL-53-JCK.

Drug Efficacy of the Humanized EP27 Antibody Glycomab Against Poorly Differentiated Colon Cancer A tumor tissue section of poorly-differentiated human colon cancer tumor COL-53-JCK (Central Institute for Experimental Animals) was transplanted into SCID mice. From day 14 after transplanting the tumor tissue section, the humanized EP27 antibody Glycomab was administered once a week at 10 mg/kg. As a result, assessment of the tumor volume on day 14 after starting the antibody administration confirmed that tumor growth is significantly suppressed in the antibody-administered group as compared to the control group (FIG. 16).

Example 15

Figure 17:
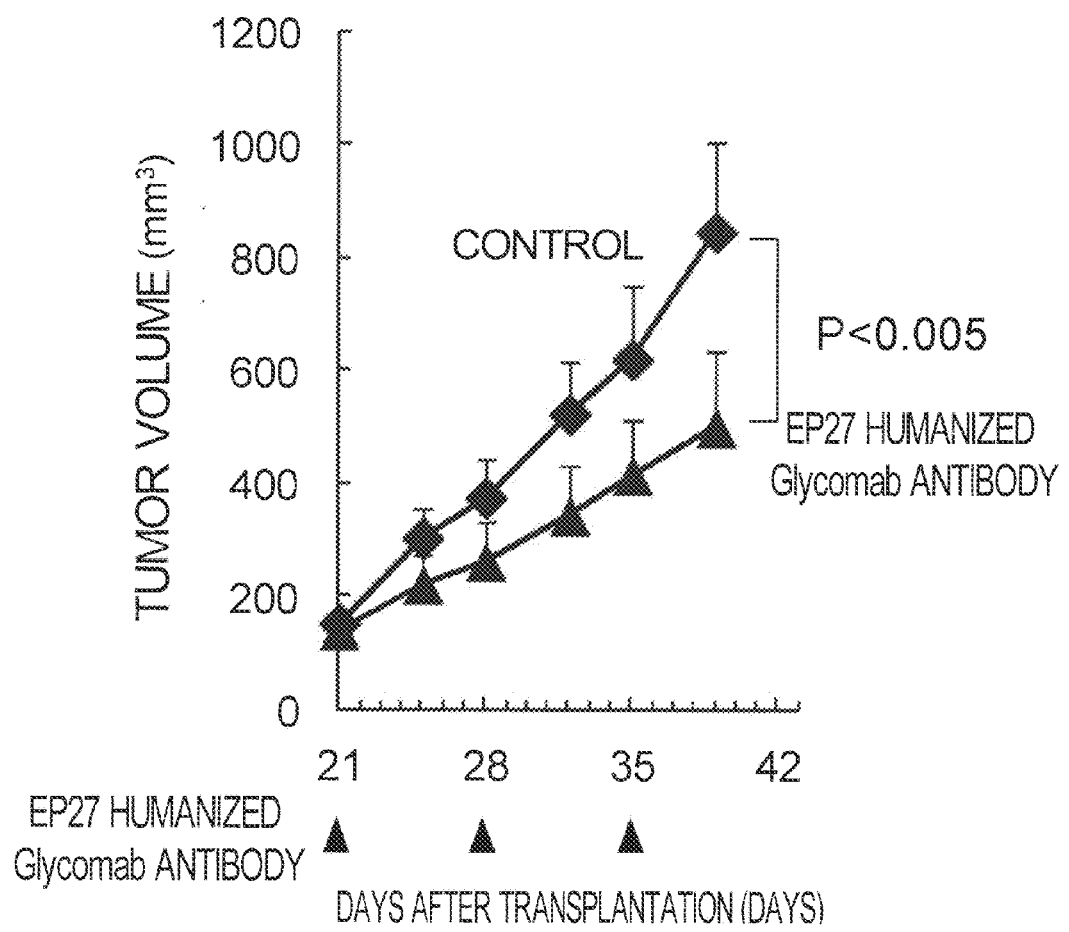
FIG. 17 is a graph showing the drug efficacy of the humanized EP27 antibody Glycomab against moderately-differentiated colon cancer using the moderately-differentiated colon cancer model PLR379.

Drug Efficacy of the Humanized EP27 Antibody Glycomab Against Moderately-Differentiated Colon Cancer Tumors in the moderately-differentiated human colon cancer tumor model PLR379 (PCT/JP2012/072852) have a feature of morphologically observed tumor budding, but epiregulin expression was detected regardless of the site of tumor budding. Tumor tissue section of this PLR379 was transplanted into SCID mice, and from day 21 after transplanting the tumor tissue section, the humanized EP27 antibody Glycomab was administered once a week at 10 mg/kg. Assessment of the tumor volume on day 18 after start of the antibody administration confirmed that tumor growth is significantly suppressed in the antibody-administered group as compared to the control group (FIG. 17).

Example 16

EREG Expression in Clinical Lung Adenocarcinoma

Figure 18:
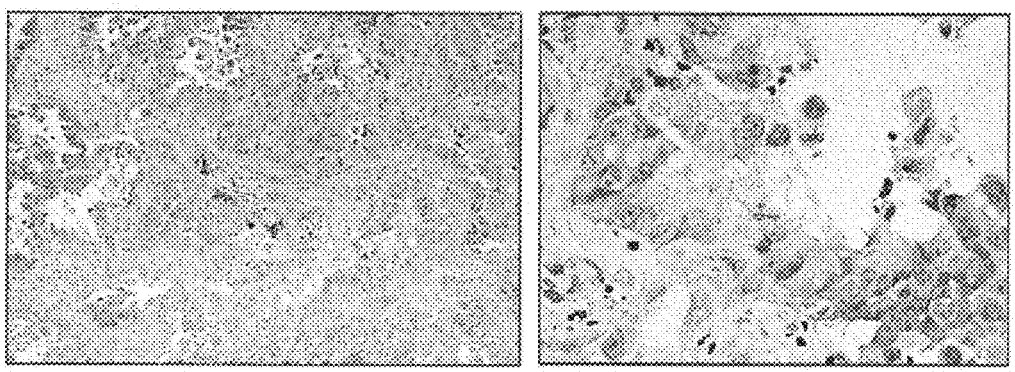
FIG. 18 presents photographs showing the Epiregulin expression in clinical cases of lung adenocarcinoma.

To examine EREG expression in seven clinical cases of lung adenocarcinoma, thinly sliced paraffin-embedded specimens of the cases were stained using the staining method described in Example 10. As a result, clear positive images were confirmed in four of the seven cases (FIG. 18).

Example 17

Figure 19:
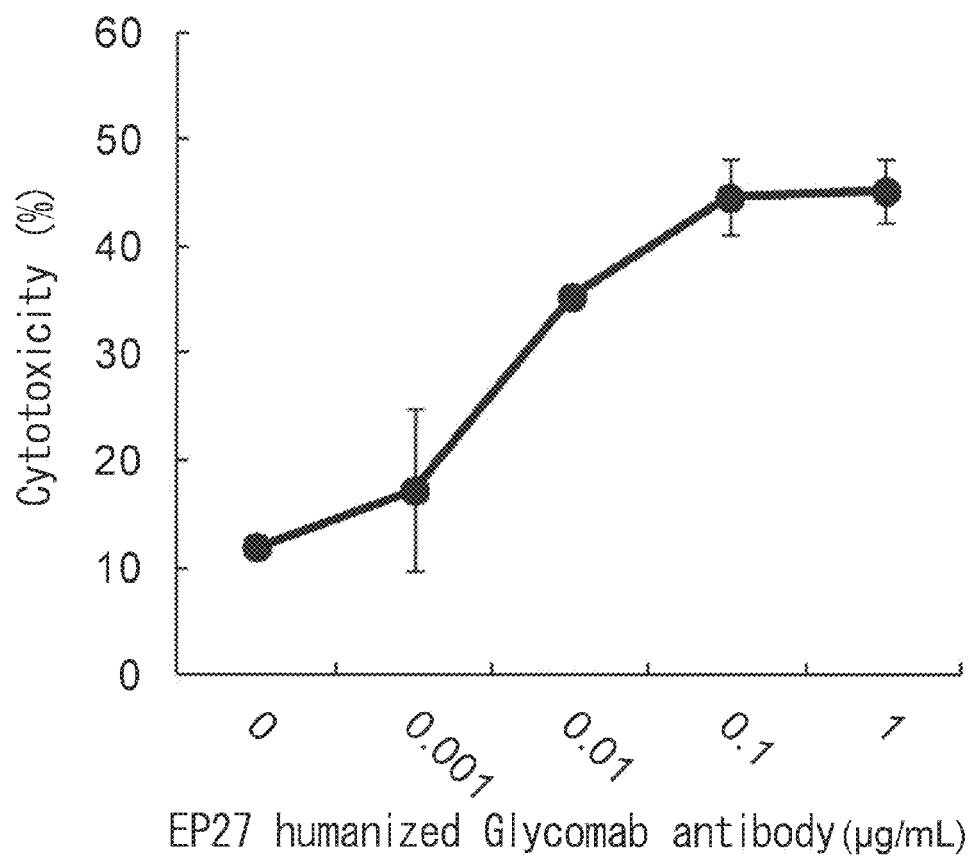
FIG. 19 is a graph showing the ADCC activity (specific calcein AM release rate) of the humanized EP27 antibody Glycomab against the human lung adenocarcinoma cell line Calu-3.

ADCC Activity of the Humanized EP27 Antibody Glycomab Using Human Peripheral Blood Mononuclear Cells as Effector Cells The ADCC activity was evaluated for the human lung adenocarcinoma line Calu-3 using human PBMC as effector cells. As a result, the humanized EP27 antibody Glycomab was confirmed to induce ADCC against Calu-3 cells (FIG. 19).

Example 18

Figure 20:
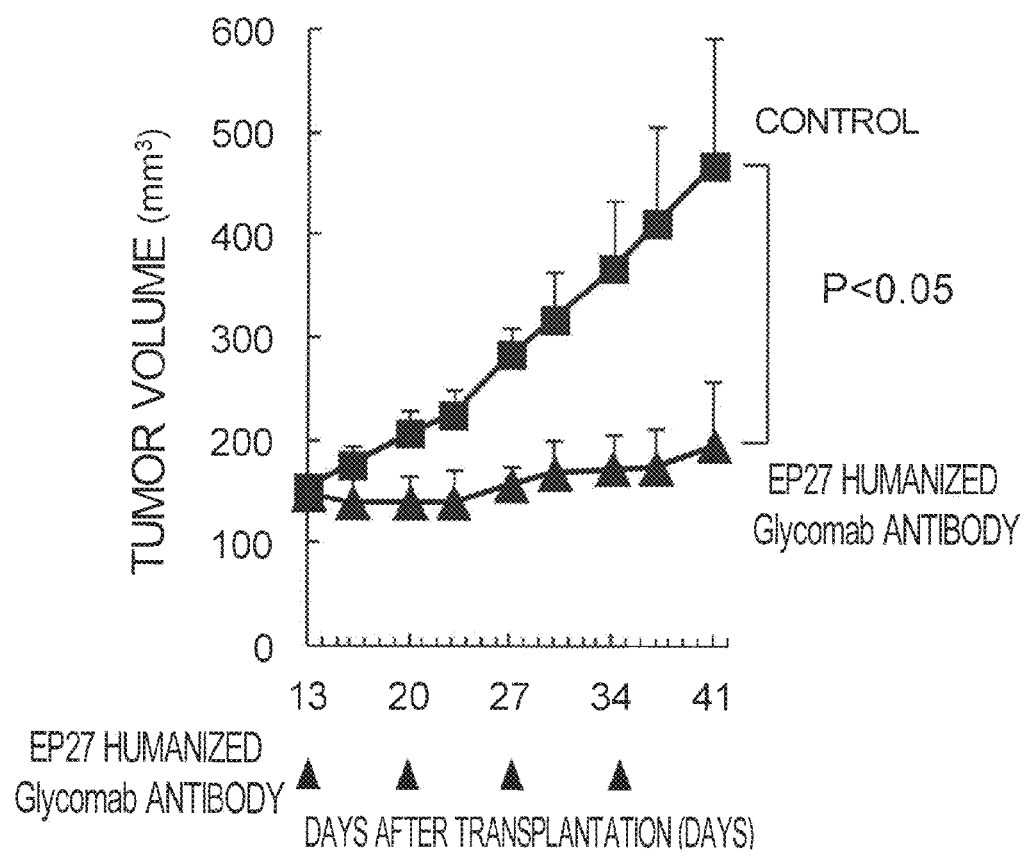
FIG. 20 is a graph showing the drug efficacy of the humanized EP27 antibody Glycomab against lung adenocarcinoma using the lung adenocarcinoma model Calu-3.

Drug Efficacy of the Humanized EP27 Antibody Glycomab Against Lung Adenocarcinoma The humanized EP27 antibody Glycomab was administered to SCID mice with an implanted tumor tissue fragment of the human lung adenocarcinoma model Calu-3, once a week at 10 mg/kg from day 13 after transplantation of the tumor tissue fragment. The tumor volume was measured on day 28 after initiation of the antibody administration. It was confirmed that tumor growth was significantly suppressed in the antibody administration group as compared with the control group (FIG. 20).

Example 19

Cellular Internalization of the Humanized EP27 Antibody

Figure 21:
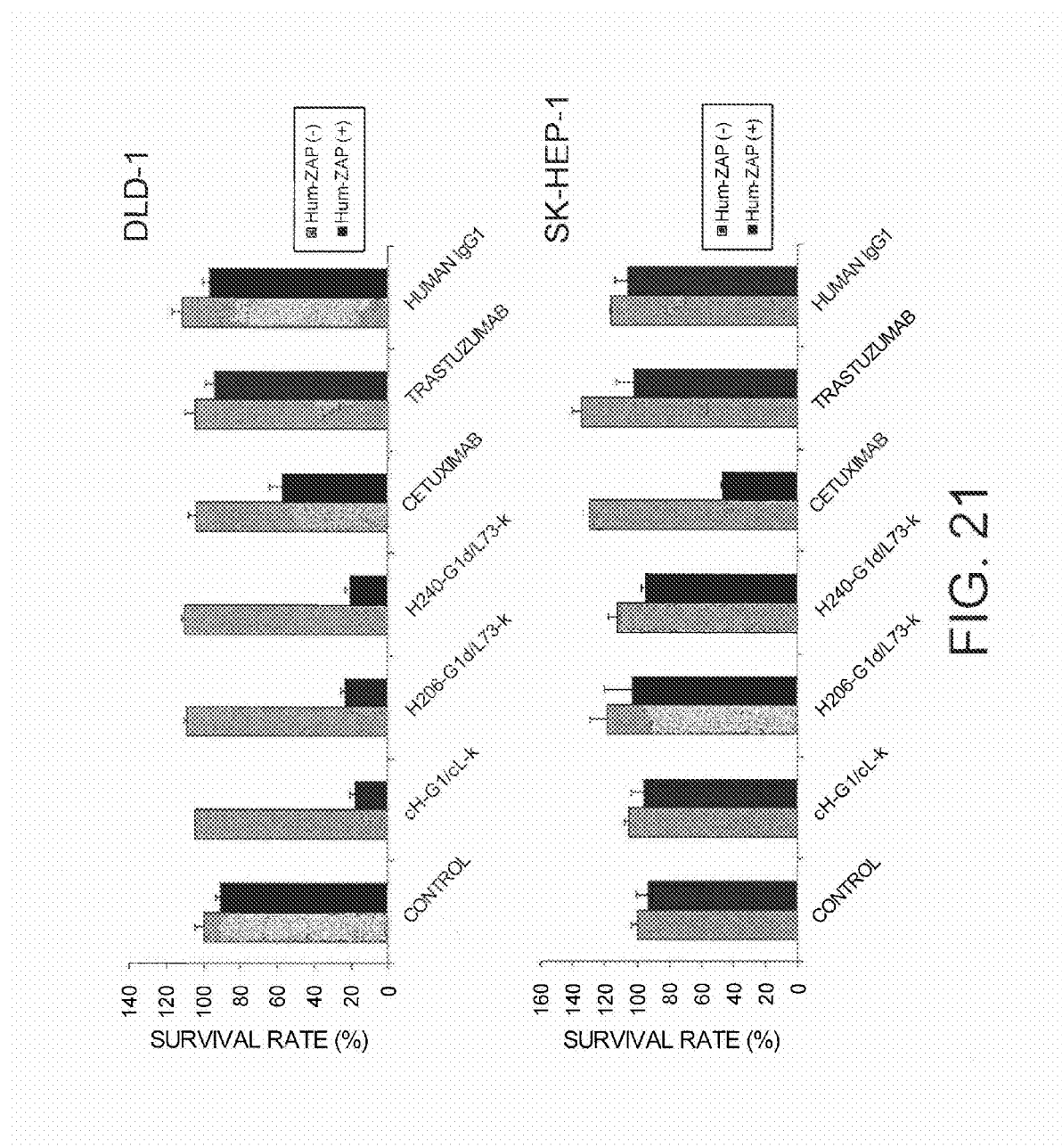
FIG. 21 shows that the antibody-drug conjugate comprising the humanized EP27 antibody Glycomab becomes internalized in the DLD-1 cell line cells which express Epiregulin, and cause cell damage against the DLD-1 cell line.

Cellular internalization of the humanized EP27 antibody was evaluated by the following method. When a primary antibody becomes internalized, saporin which is a ribosome-inactivating protein carried by the secondary antibody is transported into the cell via binding of the secondary antibody to the primary antibody. Once it is internalized, saporin dissociates from the IgG conjugate, inhibits protein synthesis, and then causes cell death. An EREG-expressing DLD-1 cell line or the control SK-HEP1 cell line was seeded at a cell density of 1×10³ cells to each well of 96-well microplates, and on the following day, the humanized EP27 antibody Glycornab was added as the primary antibody, and goat IgG recognizing the human monoclonal antibody bound to the ribosome-inactivating protein Hum-ZAP (Advanced Targeting Systems) was added as the secondary antibody. Four days after the addition, cell viability was evaluated by WST8 (Donjindo). As show in FIG. 21, the humanized EP27 antibody Glycomab induced cell death only against the EREG-expressing DLD-1 cell line. On the other hand, it did not induce cell death against the SK-HEP1 cell line which was used as the control.

Reference Example 1

Isolation of Human and Cynomolgus Monkey Eriregulin Genes

The full-length human EREG cDNA (CR541887, SEQ ID NO: 169) was isolated by a standard method, and a plasmid produced by cloning this gene fragment into a vector for expression in mammalian cells (pMCN) was named hEREG/pMCN. pMCN can induce expression of a foreign gene under the mouse CMV promoter (ACCESSION No. U 68299), and is a vector inserted with a neomycin-resistance gene. The full-length cynomolgus monkey EREG cDNA was isolated by a standard method from a cynomolgus monkey cDNA library based on the sequence information of rhesus monkey EREG cDNA (XM_001102069), and a plasmid produced by cloning this gene fragment (a gene fragment encoding the sequence of SEQ ID NO: 165) into a vector for expression in mammalian cells (pMCN) was named cyEREG/pMCN. hEREG/pMCN and cyEREG/pMCN were introduced into the CHO DG44 strain (Invitrogen) by electroporation, and selection with 500 µg/mL Geneticin established CHO cells that steadily express full-length human EREG and CHO cells that steadily express full-length cynomolgus monkey EREG, which were named hEREG_DG and cyEREG_DG, respectively.

Reference Example 2

Establishment of Methods for Expressing Mature Forms of Human and Cynomolgus Monkey Epiregulins A PCR method was used to amplify cDNAs for expressing the six-histidine-repeat sequence at the C termini of the extracellular regions of mature human EREGs of the human and cynomolgus monkey Epiregulin genes (polypeptides in which the sequence of SEQ ID NO: 171 has been fused to the N termini of the polypeptides of SEQ ID NOs: 170 and 34, respectively). Expression vectors for use in mammalian cells into which these cDNAs have been individually inserted were linearized by restriction enzymes; and then by introducing those into Freestyle 293 cells using 293 fectin, mature human and cynomolgus monkey Epiregulins were transiently expressed.

Reference Example 3

Preparation of Epiregulin

The mature human Epiregulin gene and the mature cynomolgus monkey Epiregulin gene were inserted individually into an expression vector for mammalian cells. Mature human EREG-6His and cynomolgus monkey EREG-6His fusion proteins isolated from the culture solutions of animal cells made to express each of the genes by the method below were purified.

The extracellular region of mature human EREG (a polypeptide in which the sequence of SEQ ID NO: 171 is fused to the N terminus of SEQ ID NO: 34) fused in-frame with a six-histidine region was inserted into an expression vector for mammalian animals to construct the hsEREG-6His expression vector (herein below, the expressed fusion polypeptide is called hsEREG-His). The extracellular region of mature cynomolgus monkey EREG (a polypeptide in which the sequence of SEQ ID NO: 171 is fused to the N terminus of SEQ ID NO: 170) fused in-frame with a six-histidine region was inserted into an expression vector for mammalian animals to construct the csEREG-6His expression vector (herein below, the expressed EREG is called cysEREG-His). The hs EREG-6His expression vector and the csEREG-6His expression vector were introduced into FreeStyle 293 cells (Invitrogen) using 293 fectin (Invitrogen), and the transduced cell lines were cultured under Zeocin (500 µg/mL) selection for six days at 37° C. in an 8% $CO_2$ incubator.

Next, hsEREG-His and cysEREG-His were purified from the culture supernatant. 4 M imidazole was added to the culture supernatant at a final concentration of 10 mM imidazole, and this liquid mixture was mixed with the Ni resin in the His MicroSpin Purification System (Amersham). The resin was washed with 20 mM imidazole and 50 mM imidazole, and then hsEREG-His or cysEREG-His was eluted using 200 mM imidazole (elution fraction 1), and then hsEREG-His or cysEREG-His was eluted using 400 mM imidazole (elution fraction 2). Next, the buffer containing eluted hsEREG-His or cysEREG-His was exchanged by dialysis to PBS using a Bio-tech dialysis cup MWCO8000. The purified protein was quantified using the PACE method at a wavelength of 280 nm, and this was converted to protein content.

Figure 9:
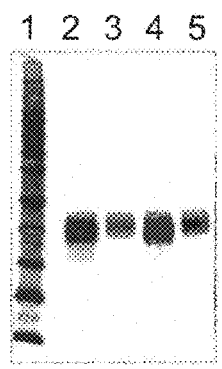
FIG. 9 is an image showing the electrophoretic patterns of human Epiregulin (hsEREG-His) and monkey Epiregulin (cysEREG-His).

The electrophoretic patterns of the purified proteins are shown in FIG. 9.

Reference Example 4

Establishment of an Epiregulin ELISA System

A soluble human EREG fragment having a mature EGF domain structure (the polypeptide of SEQ ID NO: 34 which corresponds to $^{63}$Val to $^{108}$Leu) was purchased from R&D Systems (cat. no. 1195-EP/CF). The soluble human EREG fragment was used to coat nunc immunoplates, and after blocking with a BSA-containing solution, the binding reactivity of purified anti-EREG antibodies was analyzed. Addition of the purified anti-EREG antibodies was followed by one hour of incubation, the plates were washed, and then an alkaline phosphatase-labeled anti-human IgG antibody (Zymed) was added to each well of the washed plates and then allowed to react. Each well was washed, and then the amount of bound antibody was determined by addition of a test reagent, Sigma p-Nitrophenyl phosphate Tablets.

Reference Example 5

Establishment of a System for Inhibiting Epiregulin Binding by Competitive ELISA The soluble human EREG fragment having a mature EGF domain structure (the polypeptide of SEQ ID NO: 34 which corresponds to $^{63}$Val to $^{108}$Leu) was purchased from R&D Systems (cat. no. 1195-EP/CF). The soluble human EREG fragment was used to coat nunc immunoplates, and after blocking with a BSA-containing solution, the competitive binding reactivity between mouse hybridoma-derived EP27 and the purified humanized anti-EREG antibody was analyzed. Mouse hybridoma-derived EP27 and a purified humanized anti-EREG antibody were added to the plates, and after two hours of incubation, the plates were washed; and an alkaline phosphatase-labeled anti-human IgG antibody (Zymed) was added to each well of the plates and then allowed to react. Each well was washed, and then the amount of bound antibody (A405/655 detection value) was determined by addition of a test reagent, Sigma p-Nitrophenyl phosphate Tablets.

switching to HBS-EP+ to measure the dissociation phase for 15 minutes. After completion of the dissociation phase measurement, the sensor chip was washed with 25 mM NaOH and regenerated. A data analysis software exclusively for Biacore, Biacore T100 Evaluation Software Version 2.0.1, was used to perform kinetic analyses to calculate the association rate constant ($k_a$), dissociation rate constant ($k_d$), and the rate constant ratio from the obtained sensorgrams. The results are shown in Table 21. To correct for the day-to-day differences in the measurement values, FIGS. 1 to 4 and Tables 16 and 19 show ratios based on taking the value of the control sample (cH-G1/cL-k) measured on the same day as 1.

TABLE 21

| ANTIBODY NAME | Affinity for human EREG | | | Affinity for cynomolgus monkey EREG | | |
|---|---|---|---|---|---|---|
| | KD (M) | $k_a$ (1/Ms) | $k_d$ (1/s) | KD (M) | $k_a$ (1/Ms) | $k_d$ (1/s) |
| cH-G1/cL-k | $2.0 \times 10^{-10}$ | $1.1 \times 10^{6}$ | $2.2 \times 10^{-4}$ | $5.2 \times 10^{-9}$ | $9.9 \times 10^{5}$ | $5.2 \times 10^{-3}$ |
| H205-G1d/L53-k | $2.2 \times 10^{-10}$ | $5.4 \times 10^{5}$ | $1.2 \times 10^{-4}$ | $1.2 \times 10^{-9}$ | $5.8 \times 10^{5}$ | $7.0 \times 10^{-4}$ |
| H205-G1d/L73 k | $1.9 \times 10^{-10}$ | $3.9 \times 10^{5}$ | $7.5 \times 10^{-5}$ | $6.9 \times 10^{-10}$ | $3.7 \times 10^{5}$ | $2.6 \times 10^{-4}$ |
| H206-G1d/L53 k | $1.7 \times 10^{-10}$ | $6.6 \times 10^{5}$ | $1.1 \times 10^{-4}$ | $9.4 \times 10^{-10}$ | $6.4 \times 10^{5}$ | $6.1 \times 10^{-4}$ |
| H206-G1d/L73-k | $1.3 \times 10^{-10}$ | $5.5 \times 10^{5}$ | $7.4 \times 10^{-5}$ | $4.5 \times 10^{-10}$ | $5.0 \times 10^{5}$ | $2.3 \times 10^{-4}$ |
| H231-G1d/L53 k | $2.3 \times 10^{-10}$ | $4.5 \times 10^{5}$ | $1.1 \times 10^{-4}$ | $1.4 \times 10^{-9}$ | $6.2 \times 10^{5}$ | $8.6 \times 10^{-4}$ |
| H231-G1d/L73-k | $1.4 \times 10^{-10}$ | $6.2 \times 10^{5}$ | $8.7 \times 10^{-5}$ | $6.6 \times 10^{-10}$ | $4.2 \times 10^{5}$ | $2.8 \times 10^{-4}$ |
| H240-G1d/L53-k | $2.7 \times 10^{-10}$ | $4.2 \times 10^{5}$ | $1.1 \times 10^{-4}$ | $1.5 \times 10^{-9}$ | $6.1 \times 10^{5}$ | $8.9 \times 10^{-4}$ |
| H240-G1d/L73-k | $2.2 \times 10^{-10}$ | $3.4 \times 10^{5}$ | $7.7 \times 10^{-5}$ | $8.7 \times 10^{-10}$ | $3.4 \times 10^{5}$ | $2.9 \times 10^{-4}$ |
| H87-G1d/LB-k | $1.5 \times 10^{-10}$ | $1.3 \times 10^{6}$ | $2.0 \times 10^{-4}$ | $5.2 \times 10^{-9}$ | $8.6 \times 10^{5}$ | $4.5 \times 10^{-3}$ |

Reference Example 6

Establishment of Antigen Binding Activity (A Method for Measuring Affinity)

The affinity and association rate constant of an anti-EREG antibody for an antigen were measured by the single-cycle kinetics method of surface plasmon resonance assay using Biacore™-T100 (GE Healthcare, Japan). HBS-EP+ (GE Healthcare Japan) was used for the running buffer, and an amine coupling kit (GE Healthcare Japan) was used to covalently bond Protein A to the CM5 chip (carboxymethyl dextran-coated chip). HBS-EP+ (GE Healthcare Japan) was used for the running buffer, and an amine coupling kit (GE Healthcare Japan) was used to covalently bond Protein A to the GM5 chip (carboxymethyl dextran-coated chip). Each anti-EREG antibody was prepared so that approximately 350 RU will be captured by Protein A. Human EREG or cynomolgus EREG used as the analyte was prepared at 0, 0.7, 1.4, 2.8, 5.6, and 11.2 nM using HBS-EP+. Measurement was carried out by first allowing Protein A to capture the antibody solution, and then at a flow rate of 30 μL/min, successively injecting each of the 0, 0.7, 1.4, 2.8, 5.6, and 11.2 nM human EREG or cynomolgus EREG solutions for three minutes to allow reaction to take place. Then, the solution was switched to HBS-EP+, and the dissociation phase was measured for 15 minutes. After completion of the dissociation phase measurement, the sensor chip was washed with 25 mM NaOH and regenerated. The measurement at zero concentration was similarly carried out by allowing Protein A to capture the antibody solution, and performing three-minute HBS-EP+ injections successively for five times to allow reaction to take place, and then Reference Example 7

Establishment of a Method for Measuring ADCC Activity

A mononuclear cell fraction collected from human peripheral blood was used for the human-derived effector cells. From a healthy volunteer (adult male), 50 mL of peripheral blood was collected using a syringe preloaded with 200 μL of a 1000 unit/mL heparin solution (Novo-Heparin Injection 5000 units, Novo Nordisk). The peripheral blood was diluted two-fold with PBS(-), and Ficoll-Paque PLUS was injected in advance to carry out centrifugation. This was added into a Leucosep lymphocyte separation tube (Greiner Bio-one), and centrifuged (at 2150 rpm for ten minutes at room temperature), followed by collection of the mononuclear cells fraction layer. The cells were washed once with 10% FBS/D-MEM and suspended in 10% FBS/D-MEM at a cell density of $5 \times 10^6$/mL to prepare an effector cell suspension solution. The cell suspension served as a human PBMC solution in subsequent experiment.

The target cell suspension solution was prepared for testing at the time of use. The MIA PaCa-2 human pancreatic cancer cell line (ATCC) was maintained by subculturing in Dulbecco's Modified Eagle Media (Invitrogen) containing 10% FBS, 2.5% Horse Serum, 4 mmol/L L-Glutamine (Invitrogen), 4.5 g/L glucose (Invitrogen), and 1.5 g/L Sodium bicarbonate (Invitrogen) (hereinafter referred to as the subculture medium). For the labeling reagent, 228 μL of 10% FBS/D-MEM was added to a tube containing 12 μL of a Calcein-AM/DMSO stock solution (nacalai) prepared at 4 mg/mL to produce a Calcein-AM solution by gentle suspension. To $1 \times 10^6$ cells of the MIA PaCa-2 cell line subjected to centrifugation (at 1200 rpm for five minutes at 4° C.), the Calcein-AM solution prepared as described above was added at 200 μL per cell pellet of $1 \times 10^6$ cells to prepare a cell suspension. The whole amount of this suspension solution was transferred to a plastic blood collection tube (Nihon Pharmaceutical), and this was incubated in a $CO_2$ incubator at 37° C. for two hours. The cells were washed three times with 10% FBS/D-MEM, and the target cell suspension solution was prepared by suspending the washed cells in 10% FBS/D-MEM to give $20×10^4$ cells/mL ($1×10^4$/50 μL).

For the target cell suspension solution, 100 μL of the medium was added to a 96-well flat-bottomed plate. Next, anti-Epiregulin monoclonal antibodies (H206-G1d/L73-k (SEQ ID NO: 142/141), H240-G1d/L73-k (SEQ ID NO: 150/141), and chimeric EP27 (SEQ ID NO: 32/33)) were diluted in a medium and then added to the plate at 50 μL per well. The antibodies were added at final concentrations of 0.0001 μg/mL to 10 μg/mL. Next, a PBMC solution ($1×10^7$ cells/mL) was added at 50 μL per well, the plate was left to stand in a 5% $CO_2$ gas incubator at 37° C. for four hours, and the specific Calcein-AM release rate was determined. The plate was subjected to centrifugation (at 1200 rpm for five minutes at room temperature), and fluorescence intensity ($\lambda_{ex}$=490 nm and $\lambda_{em}$=515 nm) of 100 μL of the supernatant collected from each well of the plate was measured using a fluorophotometer. The specific calcein release rate was determined from the formula below (Formula 3).

[Formula 3]

Specific calcein release rate (%)=(A−C)×100/(B−C)

A represents the fluorescence intensity in each well; B represents the average fluorescence intensity of wells to which 50 μL of 10% FBS/D-MEM, 50 μL of the target cell suspension solution, and 100 μL of an NP-40 solution have been added; and C represents the average fluorescence intensity of wells to which 50 μL of 10% FBS/D-MEM, 50 μL of the target cell suspension solution, and 100 μL of 10% FBS/D-MEM have been added. The test was performed at N=3, and the specific calcein release rate for each antibody concentration was determined using Microsoft Office Excel 2007.

Reference Example 8

Method for Measuring Neutralizing Activity (1) Establishment of a Ba/F3 Cell Line that Expresses a Human EGFR Chimeric Receptor (EGFR_BAF)

Using standard methods, a human EGF receptor having the sequence shown in SEQ ID NO: 166 (GenBank Acc. No. NM_005228) (hereinafter referred to as "hEGFR") was isolated, and then a vector that can express a human EGF receptor (pCXZD1/EGFR#3) was prepared.

Fifteen micrograms of the linearized hEGFR expression vector (pCXZD1/EGFR#3) obtained by PvuI digestion was transfected into Ba/F3 cells by electroporation (Gene Pulser; BioRad) under conditions of 0.33 kV and 950 μFD. Transfected cells were selected in an RPMI1640 medium containing 10% FBS, 300 μg/mL Zeocin, and recombinant human Epiregulin (R&D Systems, Cat: 1195-EP/CF, 200 ng/mL); and the EGFR_BAF cell line was isolated.

(2) Activity of Anti-Epiregulin Antibodies to Neutralize Human Epiregulin- or Monkey Epiregulin-Dependent Cell Proliferation of the EGFR_BAF Cell Line Experiments to measure the activity of anti-Epiregulin antibodies to neutralize human Epiregulin- or monkey Epiregulin-dependent cell proliferation were performed using the EGFR_BAF cell line isolated by the method described in (1). Cells were washed to remove human Epiregulin present at the time of culturing. Then the cells were re-suspended in an RPMI1640 medium containing 10% FBS as well as hsEREG-His or cysEREG-His (final concentration of 2.5 ng/mL), and the cells were seeded into a 96-well plate at a density of $2×10^4$ cells/100 μL/well. An anti-Epiregulin antibody diluted by the medium was added to the cells at various concentrations (0.014 μg/mL to 30 μg/mL), and then the cells were cultured in a 5% $CO_2$ incubator for three days at 37° C. After culturing, the measurement reagent of the Cell Counting Kit (Dojindo) was added, and color development was carried out for two hours. Then, absorbance of the reaction solution (450/655 nm) was measured using Benchmark Plus (Bio-Rad). The value for 0 μg/mL antibody concentration was used as the control value to calculate the cell growth suppression rate (OD value at each antibody concentration/OD value of the control×100 (%)).

Reference Example 9

Measurement of the Amount of Aggregate by Gel Filtration Chromatography

Using G3000SW$_{XL}$ (particle size of 5 μm, 7.8 mm I.D.×30 cm, manufactured by TOSOH) for the column, and using 50 mM sodium phosphate buffer (pH7.0) containing 300 mM NaCl as the mobile phase, the amount of aggregate was measured by gel filtration chromatography. A column connected to an Alliance system (manufactured by Waters) was equilibrated at a flow rate of 0.5 mL/min, and then 5-10 μg of antibody solution was injected into the column. Antibody elution was detected using an ultraviolet absorption detector (215 or 280 nm). From the obtained chromatogram, the proportion of aggregate peak area in the total peak area was calculated.

Reference Example 10

Measurement of the Thermal Denaturation Midpoint Temperature (Tm) by a Differential Scanning Caloimeter A 20 mmol/L sodium acetate buffer (pH 6.0) containing 150 mmol/L sodium chloride was prepared as the external solution for dialysis, and dialysis was carried out for one whole day by soaking in this external solution a dialysis membrane enclosing an antibody solution of an equivalent amount of 50 to 100 μg antibody. An antibody solution prepared at 50 μg/mL to 100 μg/mL antibody concentration using the external solution for dialysis was used as the sample solution for Tm value measurements.

A suitable DSC equipment, for example, DSC-II (manufactured by Calorimetry Sciences Corporation) or MicroCal VP-DSC (manufactured by GE healthcare) can be used for this experiment. A sufficiently degassed sample solution and a reference solution (external solution for dialysis) were individually enclosed in the calorimeter cells, and subjected to sufficient thermal equilibration at 40° C. Next, a DSC scan was run from 40° C. to 100° C. with a scanning rate of approximately 1K to 2.5 K/min. The results of this measurement are given as the top of the denaturation peak as a function of temperature. The thermal denaturation midpoint temperature of the sample was calculated bye assigning the peak of the Fab domain according to a non-patent document (Rodolfo et al., Immunology Letters (1999), p47-52).

Reference Example 11 pI Measurements by Isoelectric Focusing

Using Phastsystem Cassette (Amersham Bioscience), a Phast-Gel Dry IEF (Amersham Bioscience) gel was swollen for about 30 minutes in a swelling solution having the composition described below.

TABLE 22

| COMPOSITION | VOLUME |
| --- | --- |
| 20% Glycerol | 0.95 mL |
| Milli-Q WATER | 0.95 mL |
| Bio-Lyte 7/9 (BioRad) | 10 µL |
| Bio-Lyte3/10 (BioRad) | 10 µL |
| Pharmalyte 8-10.5 for IEF (AmerchamBioscience) | 80 µL |

The swollen gel was used to perform electrophoresis using the PhastSystem (Amersham Bioscience) controlled by the program described below. The sample was added to the gel in Step 2. A Calibration Kit for pI (Amersham Bioscience) was used for the pI markers.

TABLE 23

| STEP | CONDITION |
| --- | --- |
| STEP 1 | 2000 V, 2.5 mA, 3.5 W, 15° C., 75 Vh |
| STEP 2 | 200 V, 2.5 mA, 3.5 W, 15° C., 15 Vh |
| STEP 3 | 2000 V, 2.5 mA, 3.5 W, 15° C., 410 Vh |

After electrophoresis, the gel was fixed with 20% TCA and silver staining was then carried out using the Silver Staining Kit, Protein (Amersham Bioscience) according to the instructions provided with the kit. After staining, the isoelectric point of the sample was calculated based on the known isoelectric points of the pI markers.

Reference Example 12

Construction of a Strain Expressing Afucosyl Antibodies

In a cell where expression of both fucose transporter genes on homologous chromosomes is artificially inhibited, fucose transporter function is inhibited. By using this cell, a fucose-deficient antibody can be obtained (WO2006/067913, and such). Furthermore, fucose-deficient antibodies could also be obtained when antibodies are produced in cells with forced expression of beta 1,4-N-acetylglucosaminyl-transferase III and Golgi alpha-mannosidase II (Ferrara et al., Biotechnol. Bioeng. (2006) 93 (5), 851-861). Afucosylated EREG antibodies prepared by these techniques which are known to those skilled in the art were used for the investigation.

Reference Example 13

Immunogenicity Risk Assessment Using In Silico Immunogenicity Predication Tool, Epibase The clinical usefulness and efficacy of antibody pharmaceuticals are limited by anti-drug antibodies (ADAs). ADAs affect the drug efficacy and kinetics of antibody pharmaceuticals and sometimes cause serious side effects. Many immunogenicity-influencing factors have been reported, and in particular it is believed to be important that T cell epitopes are contained in antigens. In silico tools available for predicting such T cell epitopes include Epibase (Lonza), iTope/TCED (Antitope), and EpiMatrix (EpiVax). It has been reported that sequences containing T-cell epitopes present in proteins of interest could be predicted by using the tools described above (Expert Opin Biol Ther. 2007 March; 7(3): 405-18).

Epibase Light (Lonza) is an in silico tool for calculating the binding capacity between 9-mer peptide and major DRB1 allele using FASTER algorism (Expert Opin Biol Ther. 2007 March; 7(3): 405-18). This tool enables identification of T-cell epitopes that strongly or moderately bind to MHC class II.

An in silico immunogenicity score can be determined for each modified antibody according to the following formula (Formula 4) in the system of Epibase Light (Lonza).

[Formula 4]

$$\text{Immunogenicity score} = \text{Sum (each DRB1 allotype population frequency} \times \text{number of critical epitopes)}$$

The calculation reflects the abundance ratio of DRB1 allotypes. For this purpose, it is possible to use the following abundance ratio in Caucasian.

DRB1*1501(24.5%), DRB1*0301(23.7%), DRB1*0701 (23.3%), DRB1*0101(15.0%), DRB*1101(11.6%), DRB1*1302(8.2%), DRB1*1401/1454(4.9%), DRB1*0901 (2.3%), DRB1*1502(0.5%), DRB1*1202(0.1%)

All epitopes contained in each modified antibody sequence that exhibit strong or moderate binding are identified by FASTER algorism, and then epitopes after excluding human germline sequences and junction sequences between variable region and constant region are used as critical epitopes in immunogenicity score calculation. When the score is smaller, it means that a sequence has lower immunogenicity risk.

Reference Example 14

Drug Efficacy Tests on Anti-Epiregulin Antibodies Using In Vivo Models (1) Maintenance of Cell Lines Used for Transplantation into In Vivo Models MIA PaCa-2 cells (ATCC) and DLD-1 (ATCC) were used for the in vivo models. MIA PaCa-2 cells were maintained by subculturing in Dulbecco's Modified Eagle Media (Invitrogen) containing 10% FBS, 2.5% Horse Serum, 4 mmol/L L-Glutamine (Invitrogen), 4.5 g/L glucose (Invitrogen), and 1.5 g/L Sodium bicarbonate (Invitrogen) (hereinafter referred to as the subculture medium). DLD-1 cells were maintained by subculturing in an RPMI1640 medium (SIGMA) containing 10% FBS, 10 mmol/L HEPES (Invitrogen), 4.5 g/L glucose (Invitrogen), 1 mmol/L Sodium Pyruvate (Invitrogen) (hereinafter referred to as the subculture medium).

(2) Production of Mouse Models Transplanted with MIA PaCa-2 and DLD-1 Cells

Using a solution containing a subculture medium and MATRIGEL Matrix (BD Bioscience) at 1:1 ratio, suspensions of MIA PaCa-2 and DLD-1 cells were prepared at $5 \times 10^7$ cells/mL. 100 µL of the cell suspension ($5 \times 10^6$ cells/mouse) was transplanted subcutaneously in the abdominal region of SCID mice (female, 5 week old, CLEA Japan, Inc.). The tumor volume was calculated using Formula 5, and when the average tumor volume reached 130-330 mm³, the mouse model was determined to be established.

[Formula 5]

Tumor volume=long diameter×short diameter×short diameter/2

(3) Preparation of Administration Samples Containing Each Test Antibody

Administration samples each containing the cH-G1/cL-k antibody, H206-G1d/L7-3k antibody, or H240-G1d/L73-k antibody at 0.04 mg/mL (0.4 mg/kg administration group) or 0.2 mg/mL (2 mg/kg administration group) were prepared with physiological saline on the day of administration.

(4) Administration of the Antibody-Containing Administration Samples

The administration samples prepared in (3) was administered through the tail vein to the mouse models prepared in (2) once per week for 14 days starting from day 14 post-MIA PaCa-2 cell transplantation, and once per week for 14 days starting from day 12 post-DLD cell transplantation. As a negative control, physiological saline was similarly administered at a dose of 10 mL/kg through the tail vein once per week for the respective durations. All groups had five animals in each group, and to each group, the respective test antibody-containing administration sample was administered.

(5) Evaluation of the Antitumor Effect of Each Test Antibody

The antitumor effect of each test antibody was evaluated in the mouse model transplanted with human cancer cells. The tumor volume was measured on day 3 or day 7 after the last day of sample administration.

The invention claimed is:

1. An anti-Epiregulin antibody which is an antibody that binds to an epitope bound by an anti-Epiregulin antibody comprising heavy-chain variable region CDRs of SEQ ID NOs: 9, 10, and 11 and light chain variable region CDRs of SEQ ID NO: 12, 13, and 14, wherein the antibody is characterized in having a smaller ratio of the KD value for monkey Epiregulin of SEQ ID NO: 170 (cEREG KD) to the KD value for human Epiregulin of SEQ ID NO: 34 (hEREG KD) (cEREG KD/hEREG KD) than the cEREG KD/hEREG KD ratio of the anti-Epiregulin antibody comprising heavy-chain variable region CDRs of SEQ ID NOs: 9, 10, and 11 and light-chain variable region CDRs of SEQ ID NO: 12, 13, and 14, which is selected from any one of (1) to (8) below:
(1) an anti-Epiregulin antibody which comprises a heavy-chain variable region comprising a heavy-chain CDR1 of SEQ ID NO: 9, a heavy-chain CDR2 of SEQ ID NO: 153, and a heavy-chain CDR 3 of SEQ ID NO: 158; and a light-chain variable region comprising a light-chain CDR1 of SEQ ID NO: 163, a light-chain CDR2 of SEQ ID NO: 13, and a light- chain CDR 3 of SEQ ID NO: 14;
(2) an anti-Epiregulin antibody which comprises a heavy-chain variable region comprising a heavy-chain CDR1 of SEQ ID NO: 9, a heavy-chain CDR2 of SEQ ID NO: 153, and a heavy-chain CDR 3 of SEQ ID NO: 152; and a light-chain variable region comprising a light-chain CDR1 of SEQ ID NO: 163, a light-chain CDR2 of SEQ ID NO: 13, and a light-chain CDR3 of SEQ ID NO: 14;
(3) an anti-Epiregulin antibody which comprises a heavy-chain variable region comprising a heavy-chain CDR1 of SEQ ID NO: 9, a heavy-chain CDR2 of SEQ ID NO: 153, and a heavy-chain CDR3 of SEQ ID NO: 158; and a light-chain variable region comprising a light-chain CDR1 of SEQ ID NO: 163, a light-chain CDR2 of SEQ ID NO: 13, and a light-chain CDR3 of SEQ ID NO: 14;
(4) an anti-Epiregulin antibody which comprises a heavy-chain variable region comprising a heavy-chain CDR1 of SEQ ID NO: 9, a heavy-chain CDR2 of SEQ ID NO: 160, and a heavy-chain CDR3 of SEQ ID NO: 158; and a light-chain variable region comprising a light-chain CDR1 of SEQ ID NO: 163, a light-chain CDR2 of SEQ ID NO: 13, and a light-chain CDR3 of SEQ ID NO: 14;
(5) an anti-Epiregulin antibody which comprises a heavy-chain variable region comprising a heavy-chain CDR1 of SEQ ID NO: 9, a heavy-chain CDR2 of SEQ ID NO: 153, and a heavy-chain CDR3 of SEQ ID NO: 158; and a light-chain variable region comprising a light-chain CDR1 of SEQ ID NO: 163, a light-chain CDR2 of SEQ ID NO: 13, and a light-chain CDR3 of SEQ ID NO: 164;
(6) an anti-Epiregulin antibody which comprises a heavy-chain variable region comprising a heavy-chain CDR1 of SEQ ID NO: 9, a heavy-chain CDR2 of SEQ ID NO: 153, and a heavy-chain CDR3 of SEQ ID NO: 152; and a light-chain variable region comprising a light-chain CDR1 of SEQ ID NO: 163, a light-chain CDR2 of SEQ ID NO: 13, and a light-chain CDR3 of SEQ ID NO: 164;
(7) an anti-Epiregulin antibody which comprises a heavy-chain variable region comprising a heavy-chain CDR1 of SEQ ID NO: 9, a heavy-chain CDR2 of SEQ ID NO: 153, and a heavy-chain CDR3 of SEQ ID NO: 158; and a light-chain variable region comprising a light-chain CDR1 of SEQ ID NO: 163, a light-chain CDR2 of SEQ ID NO: 13, and a light-chain CDR3 of SEQ ID NO: 164; and
(8) an anti-Epiregulin antibody which comprises a heavy-chain variable region comprising a heavy-chain CDR1 of SEQ ID NO: 9, a heavy-chain CDR2 of SEQ ID NO: 160, and a heavy-chain CDR3 of SEQ ID NO: 158; and a light-chain variable region comprising a light-chain CDR1 of SEQ ID NO: 163, a light-chain CDR2 of SEQ ID NO: 13, and a light-chain CDR3 of SEQ ID NO: 164.

2. The antibody of claim 1, which comprises the heavy-chain constant region of SEQ ID NO: 26.

3. The antibody of claim 2, wherein the heavy-chain constant region of SEQ ID NO: 26 comprises at least one substitution of amino acid at a position selected from the group consisting of 230, 240, 244, 245, 247, 262, 263, 266, 273, 275, 299, 302, 313, 323, 325, 328, and 332 as indicated by EU numbering.

4. The antibody of claim 1, which comprises the light-chain constant region of SEQ ID NO: 27.

5. The antibody of claim 1, which has a neutralizing activity.

6. The antibody of claim 1, which has cytotoxicity.

7. The antibody of claim 6, wherein the cytotoxicity is CDC and/or ADCC.

8. The antibody of claim 1, wherein a growth inhibitor or a cytotoxic substance is linked to the antibody.

9. A pharmaceutical composition comprising the antibody of claim 1 as an active ingredient.

10. An anti-Epiregulin antibody which is an antibody that binds to an epitope bound by an anti-Epiregulin antibody comprising heavy-chain variable region CDRs of SEQ ID NOs: 9, 10, and 11 and light chain variable region CDRs of SEQ ID NO: 12, 13, and 14, wherein the antibody is characterized in having a smaller ratio of the KD value for monkey Epiregulin of SEQ ID NO: 170 (cEREG KD) to the KD value for human Epiregulin of SEQ ID NO: 34 (hEREG KD) (cEREG KD/hEREG KD) than the cEREG KD/hEREG KD ratio of the anti-Epiregulin antibody comprising heavy-chain variable region CDRs of SEQ ID NOs: 9, 10, and 11 and light-chain variable region CDRs of SEQ ID NO: 12, 13, and 14, which is selected from any one of (1) to (8) below:
(1) an anti-Epiregulin antibody which comprises a heavy-chain variable region corresponding to the heavy-chain variable region in SEQ ID NO: 140 and a light-chain variable region corresponding to the light-chain variable region in SEQ ID NO: 136;
(2) an anti-Epiregulin antibody which comprises a heavy-chain variable region corresponding to the heavy-chain variable region in SEQ ID NO: 142 and a light-chain variable region corresponding to the light-chain variable region in SEQ ID NO: 136;
(3) an anti-Epiregulin antibody which comprises a heavy-chain variable region corresponding to the heavy-chain variable region in SEQ ID NO: 149 and a light-chain variable region corresponding to the light-chain variable region in SEQ ID NO: 136;
(4) an anti-Epiregulin antibody which comprises a heavy-chain variable region corresponding to the heavy-chain variable region in SEQ ID NO: 150 and a light-chain variable region corresponding to the light-chain variable region in SEQ ID NO: 136;
(5) an anti-Epiregulin antibody which comprises a heavy-chain variable region corresponding to the heavy-chain variable region in SEQ ID NO: 140 and a light-chain variable region corresponding to the light-chain variable region in SEQ ID NO: 141;
(6) an anti-Epiregulin antibody which comprises a heavy-chain variable region corresponding to the heavy-chain variable region in SEQ ID NO: 142 and a light-chain variable region corresponding to the light-chain variable region in SEQ ID NO: 141;

(7) an anti-Epiregulin antibody which comprises a heavy-chain variable region corresponding to the heavy-chain variable region in SEQ ID NO: t49 and a light-chain variable region corresponding to the light-chain variable region in SEQ ID NO: 141; and (8) an anti-Epiregulin antibody which comprises a heavy-chain variable region corresponding to the heavy-chain variable region in SEQ ID NO: 150 and a light-chain variable region corresponding to the light-chain variable region in SEQ ID NO: 141.

11. An anti-Epiregulin antibody which comprises a heavy-chain variable region comprising a heavy-chain CDR1 of SEQ ID NO: 9, a heavy-chain CDR2 of SEQ ID NO: 160, and a heavy-chain CDR 3 of SEQ ID NO: 158; and a light-chain variable region comprising a light-chain CDR1 of SEQ ID NO: 163, a light-chain CDR2 of SEQ ID NO: 13, and a light-chain CDR 3 of SEQ ID NO: 164.

12. The antibody of claim 11, which comprises the heavy-chain constant region of SEQ ID NO: 30.

13. The antibody of claim 11, which comprises the light-chain constant region of SEQ ID NO: 27.

14. The antibody of claim 11, which has a neutralizing activity.

15. The antibody of claim 11, which has cytotoxicity.

16. The antibody of claim 15, wherein the cytotoxicity is CDC and/or ADCC.

17. The antibody of claim 11, wherein a growth inhibitor or a cytotoxic substance is linked to the antibody.

18. An anti-Epiregulin antibody which comprises a heavy-chain variable region corresponding to the heavy-chain variable region in SEQ ID NO: 150 and a light-chain variable region corresponding to the light-chain variable region in SEQ ID NO: 141.

19. The antibody of claim 18, which comprises the heavy-chain constant region of SEQ ID NO: 30.

20. The antibody of claim 18, which comprises the light-chain constant region of SEQ ID NO: 27.

21. The antibody of claim 18, which has a neutralizing activity.

22. The antibody of claim 18, which has cytotoxicity.

23. The antibody of claim 22, wherein the cytotoxicity is CDC and/or ADCC.

24. The antibody of claim 18, wherein a growth inhibitor or a cytotoxic substance is linked to the antibody.

25. A method for producing the antibody of claim 1, which comprises collecting a host cell comprising a vector comprising a polynucleotide encoding a heavy-chain variable region that comprises a heavy-chain CDR1 of SEQ ID NO: 9, a heavy-chain CDR2 selected from the group consisting of SEQ ID NOs: 161, 160, 159, 157, 156, 155, 153, 108, 107, 106, 105, 104, 103, 102, 101, and 100, and a heavy-chain CDR3 selected from the group consisting of SEQ ID NOs: 158, 154, 152, 151, 112, 111, 110, and 11 from a culture solution.

* * * * *

UNITED STATES PATENT AND TRADEMARK OFFICE
CERTIFICATE OF CORRECTION

| | | |
|---|---|---|
| PATENT NO. | : 9,556,264 B2 | |
| APPLICATION NO. | : 14/369539 | |
| DATED | : January 31, 2017 | |
| INVENTOR(S) | : H. Shiraiwa et al. | |

It is certified that error appears in the above-identified patent and that said Letters Patent is hereby corrected as shown below:

In the Specification

Column 24
Line 35 please replace "Rankpep bio.dfci.harvard.edu/Tools/rankpep.html.)" with --Rankpep (bio.dfci.harvard.edu/Tools/rankpep.html.)--

In the Claims

Column 297
Line 6 please replace "SEQ ID NO: t49" with --SEQ ID NO: 149--

Signed and Sealed this
Second Day of May, 2017

Michelle K. Lee
*Director of the United States Patent and Trademark Office*